United States Patent
Titz et al.

(10) Patent No.: US 10,407,398 B2
(45) Date of Patent: Sep. 10, 2019

(54) **INHIBITORS OF *PSEUDOMONAS AERUGINOSA* LECB**

(71) Applicant: HELMHOLTZ-ZENTRUM FÜR INFEKTIONSFORSCHUNG GMBH, Braunschweig (DE)

(72) Inventors: Alexander Titz, Mandelbachtal (DE); Roman Sommer, Saarbrücken (DE)

(73) Assignee: HELMHOLTZ-ZENTRUM FÜR INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 15/560,784

(22) PCT Filed: Mar. 24, 2016

(86) PCT No.: PCT/EP2016/056486
§ 371 (c)(1),
(2) Date: Sep. 22, 2017

(87) PCT Pub. No.: WO2016/151066
PCT Pub. Date: Sep. 29, 2016

(65) Prior Publication Data
US 2018/0155310 A1    Jun. 7, 2018

(30) Foreign Application Priority Data
Mar. 24, 2015 (EP) .................... 15160612

(51) Int. Cl.
| | | |
|---|---|---|
| C07D 309/10 | (2006.01) | |
| C07D 405/12 | (2006.01) | |
| C07D 409/12 | (2006.01) | |
| C07D 413/12 | (2006.01) | |
| A61P 31/04 | (2006.01) | |

(52) U.S. Cl.
CPC ............ *C07D 309/10* (2013.01); *A61P 31/04* (2018.01); *C07D 405/12* (2013.01); *C07D 409/12* (2013.01); *C07D 413/12* (2013.01)

(58) Field of Classification Search
CPC .. C07D 309/10; C07D 405/12; C07D 409/12; C07D 413/12
See application file for complete search history.

(56) References Cited

FOREIGN PATENT DOCUMENTS

| | | |
|---|---|---|
| EP | 2650289 A1 | 10/2013 |
| WO | 2013/152848 A1 | 10/2013 |

OTHER PUBLICATIONS

Testa, B., Biochem. Pharmacol., 2004, 68, p. 2097-2106. (Year: 2004).*
Carchon, et al., "Synthesis of a non-charged analogue of guanosyldiphophofucose," Tetrahedron Letters, vol. 42, No. 50, Dec. 2001, pp. 8821-8824.
Hauck, et al., "Dicovery of Two Classes of Potent Glycomimetic Inhibitors of *Pseudomonas aeruginose* LecB with Distinct Binding Modes," ACS Chemical Biology, vol. 8, No. 8, Aug. 16, 2013, pp. 1775-1784.
Wen Lai, et al., "Synthesis and inhibition studies of C-(d-glycopyranosyl)methylamines," Carbohydrate Research, vol. 250, No. 1, Dec. 1993, pp. 185-193.
International Search Report for PCT/EP2016/056486, dated May 30, 2016.

* cited by examiner

*Primary Examiner* — Jonathan S Lau
(74) *Attorney, Agent, or Firm* — McDonnell Boehnen Hulbert & Berghoff LLP

(57) ABSTRACT

The present invention relates to compounds derived from deoxy fucose. These compounds are useful as lectin inhibitors, especially as inhibitors of LecB. The invention also relates to pharmaceutical compositions comprising these compounds. The invention further relates to therapeutic uses of these compounds, especially to the prophylaxis or treatment of infections involving *Pseudomonas aeruginosa*.

27 Claims, 2 Drawing Sheets
Specification includes a Sequence Listing.

INHIBITORS OF *PSEUDOMONAS AERUGINOSA* LECB

CROSS-REFERENCE TO RELATED APPLICATION

This application is a U.S. national phase of International Application No. PCT/EP2016/056486, filed on Mar. 24, 2016, which claims priority to European Patent Application No. 15160612.6, filed Mar. 24, 2015, both of which are incorporated by reference herein in their entirety.

The present invention relates to compounds derived from deoxy fucose. These compounds are useful as lectin inhibitors, especially as inhibitors of LecB. The invention also relates to pharmaceutical compositions comprising these compounds. The invention further relates to therapeutic uses of these compounds, especially to the prophylaxis or treatment of infections involving *Pseudomonas aeruginosa*.

BACKGROUND OF THE INVENTION

*Pseudomonas aeruginosa* is an opportunistic, ubiquitous gram-negative bacterium accounting for a large number of nosocomial infections in immunocompromised hosts. Additionally, it colonizes the lungs of patients suffering from cystic fibrosis, which can ultimately lead to lung failure. Based on the bacterium's high resistance towards antibiotics and the ability to form biofilms, these infections result in a high mortality of the patients. *P. aeruginosa* can switch to the biofilm mode of life, which serves as a physical barrier to survive antibiotic treatment and host immune defense. It is thereby able to maintain chronic infections. In a biofilm, bacteria are embedded in the extracellular matrix. This matrix is very complex and consists mainly of extracellular DNA, polysaccharides (pel, psl and alginate) and proteins. *P. aeruginosa* produces two soluble lectins under quorum-sensing control: LecA (or PA-IL) and LecB (or PA-IIL). These tetrameric carbohydrate binding proteins recognize specific monosaccharide residues in a calcium-dependent manner (C-type lectins). Whereas LecA is specific for D-galactose, LecB can bind L-fucosides and D-mannosides. These saccharide moieties are frequently found on the cell surface of the host and the bacterium and they are subunits of the polysaccharides of the extracellular matrix in the biofilm. Both lectins, LecA and LecB, were shown to be necessary for *P. aeruginosa* biofilm formation, suggesting a structural role for maintenance of the biofilm architecture. Since both lectins are virulence factors and necessary for biofilm formation, their inhibition is considered a promising approach for antipseudomonadal treatment. It has been shown that the inhibition of these lectins with multivalent carbohydrate-based ligands resulted in reduced biofilm formation of *P. aeruginosa* in vitro. Furthermore, inhalation of an aqueous galactose and fucose containing aerosol resulted in a reduction of respiratory tract infections with *P. aeruginosa*.

The treatment of infections with *P. aeruginosa* has been a long-standing problem since antibiotics cannot reach all the bacteria embedded within the biofilm. Therefore, there is a need for therapeutic agents that can inhibit the formation of biofilm or disintegrate the biofilm.

LecB has an unusually high affinity for fucose residues. This has been explained by the crystal structure of the complex: two calcium ions in the binding site mediate the binding of one saccharide ligand to the protein.

Lewis$^a$ trisaccharide (α-Fuc1-4((βGal1-3)-GlcNAc) is the best known monovalent ligand of LecB with a $K_d$ value of 210 nM and the crystal structure of the complex revealed an additional hydrogen bond of the GlcNAc-6-OH with the receptor. The remaining part of GlcNAc and the galactose moiety are, however, not in contact with the protein surface. Consequently, known synthetic inhibitors were simplified and based on the Fuc-α-1,4-GlcNAc disaccharide or on fucose alone. The anomeric centers of GlcNAc in Fuc-GlcNAc and of fucose were substituted with functional groups allowing facile conjugation to dendrimers, but also with small substituents to mimic the GlcNAc-6-OH in order to establish the known hydrogen bond with the receptor. This, however, did not lead to an increase in affinity of the resulting molecules when compared to the parent saccharide Lewis$^a$: the disaccharide derivatives had lower dissociation constants than Lewis$^a$ and one monosaccharide derivative an equal dissociation constant to Lewis$^a$. In another example, fucosylamides have been designed for binding to the fucose binding site and for establishing an additional hydrogen bond with LecB, but the affinity was threefold lower than methyl fucoside (Me-α-Fuc: $K_d$=430 nM).

The success of monovalent fucose-based ligands was limited. First, in all known LecB ligands, fucose glycoconjugates are α-linked and, consequently, all synthetic conjugates designed as inhibitors of LecB are terminal α-fucosides without modification of the terminal fucose. This may lead to unwanted, nonspecific binding of these molecules to various fucose-binding receptors in the host, e.g., the selectins, DC-SIGN and the mannose binding lectin. Second, the modifications introduced at the anomeric center failed to increase the binding affinity compared to the parent molecules methyl fucoside or Lewis$^a$. Methyl and p-nitrophenyl β-fucosides have also been investigated and showed strongly reduced affinity for LecB as compared to their alpha-anomers.

LecB also binds mannosides via the 2, 3 and 4 hydroxyl groups that have the same relative orientation of the hydroxyl groups in fucose. Interestingly, the additional 6-OH of mannose is involved in a hydrogen bond to the side chain of Ser23 of LecB.

However, mannose lacks the lipophilic methyl group of fucose, which establishes a contact with LecB in the crystal structure. This served as an explanation for the increased affinity of fucose over mannose (Me-α-Man: $K_d$=71 μM) towards LecB.

In EP 2 650 289 A1, the synthesis of modified mannose derivatives is described. In addition, these derivatives are tested for the activity as inhibitors of LecB. The compounds synthesized in EP 2 650 289 A1 already exhibited LecB inhibitory activity with $IC_{50}$ values in the micromolar range.

However, there remained a need in the prior art for additional and more potent *P. aeruginosa* lectin inhibitors that do not block related lectins of the host's immune system. Such lectin inhibitors are preferably small molecules that can be used as orally administered therapeutic agents.

Technical Problems Underlying the Present Invention and their Solution

Thus, one aim of the present invention was to provide novel LecB inhibitors that are useful in prophylaxis and treatment of infections, such as nosocomial infections, of *Pseudomonas aeruginosa* in a patient and respiratory tract infections of a patient suffering from cystic fibrosis. Such novel LecB inhibitors can preferably be administered orally and are selective *P. aeruginosa* lectin inhibitors that should reduce unwanted nonspecific binding of the known *P. aeruginosa* lectin inhibitors.

The present inventors surprisingly found that derivatives of 1-deoxy fucose are potent LecB inhibitors. Particularly suitable are 1-deoxy fucose with sub stituents replacing the hydrogen atom at the 3-C atom or the 4-C atom.

The above-described objects are solved and the advantages are achieved by the subject-matter of the enclosed independent claims. Preferred embodiments of the invention are included in the dependent claims as well as in the following description, examples and figures.

The above overview does not necessarily describe all advantages and all problems solved by the present invention.

SUMMARY OF THE INVENTION

In a first aspect the present invention relates to a compound of the general formula (I):

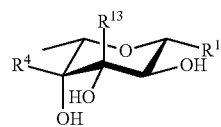

(I)

wherein
$R^4$ is selected from the group consisting of
(a) hydrogen;
(b) a $C_1$-$C_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(c) a $C_3$ to $C_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H,
(d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group; and
(g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;

$R^1$ is selected from the group consisting of
hydrogen,
—$(CH_2)_n$—$NR^2$—X—$R^3$, wherein n is 1, 2 or 3;
—$(CH_2)_n$—$NH_2$, wherein n is 2 or 3; and
—$(CH_2)_n$—O—$R^5$, wherein $R^5$ is a hydrogen atom and n is 2 or 3, or $R^5$ is a $C_1$-$C_4$ alkyl group and n is 1, 2 or 3;
wherein
$R^2$ is hydrogen or a $C_1$ to $C_3$ alkyl group;
X is $SO_2$ or CO;
$R^3$ is selected from the group consisting of:
(i) an aralkyl group, the alkyl moiety having 1 to 6 carbon atoms, and the aryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
(ii) an aralkenyl group, the alkenyl moiety having 2 to 6 carbon atoms, and the aryl moiety being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
(iii) an aryl group, optionally being substituted by one or more substituents selected from the group consisting of a halogen atom, —$NH_2$, —$NO_2$, —CN, —OH, a $C_1$-$C_4$ alkoxy group and —$COOR^5$, wherein $R^5$ is a hydrogen atom or a $C_1$-$C_4$ alkyl group, and wherein two adjacent substituents of the aryl group may be connected to form a methylenedioxy group or an ethylenedioxy group;
(iv) a heteroaryl group, optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl group may be connected to form a methylenedioxy group or an ethylenedioxy group;
(v) a heteroaralkyl group, the alkyl moiety having 1 to 6 carbon atoms and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group; and
(vi) a heteroaralkenyl group, the alkenyl moiety having 2 to 6 carbon atoms, and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group;

and
$R^{13}$ is selected from the group consisting of
(a) hydrogen;
(b) a $C_1$-$C_6$ alkyl group, optionally substituted by one or more substituents selected from the group consisting of halogen, —CN, —$NH_2$, —$NR^{11}R^{12}$, —NH—CO—$R^{11}$, —NH—$SO_2$—$R_{11}$, —$OR^{11}$, —$SR^{11}$, —$SO_2R^{11}$, —$COOR^{11}$, —$NO_2$, -triazole-$R^{11}$, and —$CH_2$—$R^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$;
(c) a $C_3$ to $C_7$ cycloalkyl group, optionally substituted by one or more substituents selected from the group consisting of halogen, —CN, —$NH_2$, —$NR^{11}R^{12}$, —NH—CO—RH, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$,
(d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

with the proviso that at least one of $R^1$, $R^4$ or $R^{13}$ is not hydrogen;

or a salt thereof or a solvate thereof or a prodrug thereof.

In a second aspect the present invention relates to a compound having a structure according to general formula (V) or general formula (VI)

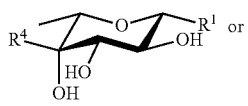
(V)

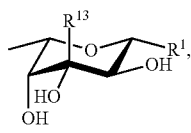
(VI)

wherein $R^4$ is selected from the group consisting of (b) a $C_1$-$C_6$ alkyl group, optionally substituted by one or more substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;

wherein $R^{12}$ is a $C_1$-$C_4$ alkyl group; and wherein $R^{11}$ is selected from the group consisting of hydrogen, a $C_1$-$C_4$ alkyl group, an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$;

(c) a $C_3$ to $C_7$ cycloalkyl group, optionally substituted by one or more substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;

wherein $R^{12}$ is a $C_1$-$C_4$ alkyl group; and wherein $R^{11}$ is selected from the group consisting of hydrogen, a $C_1$-$C_4$ alkyl group, an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, (d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(f) a heteroaryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

R$^1$ is selected from the group consisting of hydrogen, —(CH$_2$)$_n$—NR$^2$—X—R$^3$, —(CH$_2$)$_n$—NH$_2$, and —(CH$_2$)$_n$—O—R$^5$, wherein R$^5$ is a hydrogen atom or a C$_1$-C$_4$ alkyl group;

n is 1, 2 or 3;

R$^2$ is hydrogen or a C$_1$ to C$_3$ alkyl group;

X is SO$_2$ or CO;

R$^3$ is selected from the group consisting of:

(i) an aralkyl group, the alkyl moiety having 1 to 6 carbon atoms, and the aryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl moiety may be connected to form a methylenedioxy group or an ethylenedioxy group;

(ii) an aralkenyl group, the alkenyl moiety having 2 to 6 carbon atoms, and the aryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl moiety may be connected to form a methylenedioxy group or an ethylenedioxy group;

(iii) an aryl group, optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl group may be connected to form a methylenedioxy group or an ethylenedioxy group;

(iv) a heteroaryl group, optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the heteroaryl group may be connected to form a methylenedioxy group or an ethylenedioxy group;

(v) a heteroaralkyl group, the alkyl moiety having 1 to 6 carbon atoms and the heteroaryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; and (vi) a heteroaralkenyl group, the alkenyl moiety having 2 to 6 carbon atoms, and the heteroaryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group;

and

R$^{13}$ is selected from the group consisting of (b) a C$_1$-C$_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;

wherein R$^{12}$ is a C$_1$-C$_4$ alkyl group; and wherein R$^{11}$ is selected from the group consisting of hydrogen, a C$_1$-C$_4$ alkyl group, an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;

(c) a C$_3$ to C$_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;

wherein R$^{12}$ is a C$_1$-C$_4$ alkyl group; and wherein R$^{11}$ is selected from the group consisting of hydrogen, a C$_1$-C$_4$ alkyl group, an aryl group that is optionally substituted by one, two or three substituents that are independently from each other selected from the group consisting of a C$_1$-C$_4$ alkyl group, halogen, a C$_1$-C$_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$,
(d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;
(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;
(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group; and
(g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;
or a salt thereof or a solvate thereof or a prodrug thereof.

In a third aspect the present invention relates to a pharmaceutical composition comprising the compound according to the first aspect or the second aspect, and optionally comprising one or more constituents selected from the group consisting of a pharmaceutically acceptable carrier, a diluent, an excipient and an anti-bacterial therapeutic agent.

In a fourth aspect the present invention relates to the compound according to the first aspect or the second aspect for use in medicine.

In a fifth aspect the present invention relates to the compound according to the first aspect or the second aspect, optionally in combination with one or more anti-bacterial therapeutic agent(s), for use in prophylaxis or treatment of *Pseudomonas aeruginosa* infections in a patient.

In a sixth aspect the present invention relates to the compound according to the first aspect or the second aspect, optionally in combination with one or more anti-bacterial therapeutic agent(s), for use in prophylaxis or treatment of *Pseudomonas aeruginosa*-associated respiratory tract infections in a patient suffering from cystic fibrosis.

This summary of the invention does not necessarily describe all features of the invention. Other embodiments will become apparent from a review of the ensuing detailed description.

DETAILED DESCRIPTION OF THE INVENTION

Definitions

Figure 1A:
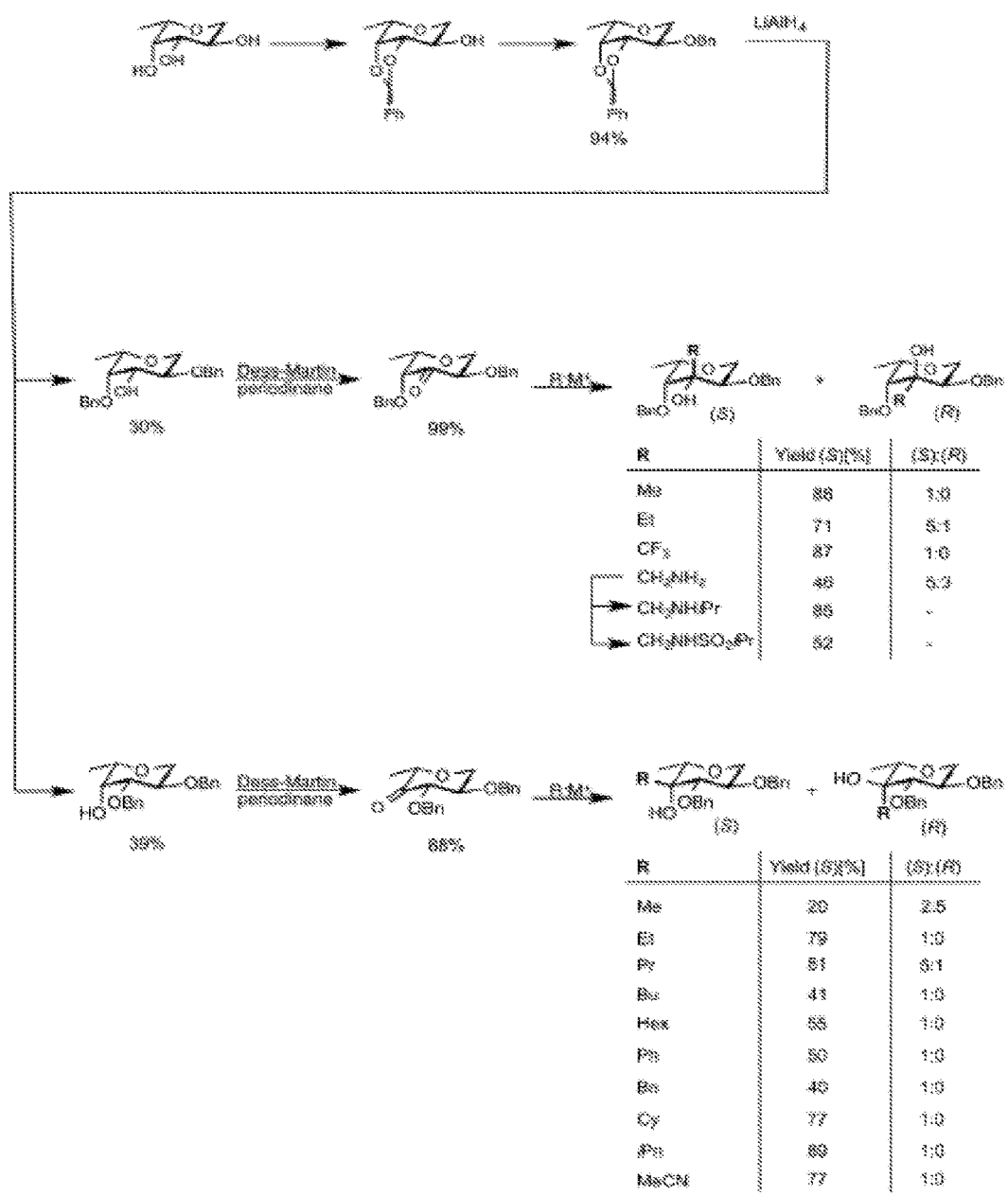
FIG. 1A-1B show the synthetic route to 3C- and 4C-modified 1-deoxy fucose derivatives of the invention.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following paragraphs, definitions of the terms: alkyl, heteroalkyl, haloalkyl, cycloalkyl, heterocycloalkyl, alicyclic system, aryl, aralkyl, heteroaryl, heteroaralkyl, alkenyl, cycloalkenyl, heteroalkenyl, heterocycloalkenyl, and alkynyl are provided. These terms will in each instance of its use in the remainder of the specification have the respectively defined meaning and preferred meanings. Nevertheless, in some instances of their use throughout the specification preferred meanings of these terms are indicated.

The term "alkyl" refers to a saturated straight or branched carbon chain. Preferably, the chain comprises from 1 to 10 carbon atoms, i.e. 1, 2, 3, 4, 5, 6, 7, 8, 9 or 10, e.g. methyl, ethyl propyl (n-propyl or iso-propyl), butyl (n-butyl, iso-butyl, sec-butyl, tert-butyl), pentyl, hexyl, heptyl, octyl, nonyl, decyl. Alkyl groups are optionally substituted.

The term "heteroalkyl" refers to a saturated straight or branched carbon chain. Preferably, the chain comprises from 1 to 9 carbon atoms, i.e. 1, 2, 3, 4, 5, 6, 7, 8, or 9, e.g. methyl, ethyl, propyl, iso-propyl, butyl, iso-butyl, sec-butyl, tert-butyl, pentyl, hexyl, heptyl, octyl, nonyl, which is interrupted one or more times, e.g. 1, 2, 3, 4, 5, with the same or different heteroatoms. Preferably, the heteroatoms are selected from O, S, and N, e.g. —$(CH_2)_n$—X—$(CH_2)_m CH_3$, with n=0, 1, 2, 3, 4, 5, 6, 7, 8, or 9, m=0, 1, 2, 3, 4, 5, 6, 7, 8, or 9 and X=S, O or NR' with R'=H or hydrocarbon (e.g. $C_1$ to $C_6$ alkyl). In particular, "heteroalkyl" refers to —O—$CH_3$, —$OC_2H_5$, —$CH_2$—O—$CH_3$, —$CH_2$—O—$C_2H_5$, —$CH_2$—O—$C_3H_7$, —$CH_2$—O—$C_4H_9$, —$CH_2$—O—$C_5H_{11}$, —$C_2H_4$—O—$CH_3$, —$C_2H_4$—O—$C_2H_5$, —$C_2H_4$—O—$C_3H_7$, —$C_2H_4$—O—$C_4H_9$ etc. Heteroalkyl groups are optionally substituted.

The term "haloalkyl" refers to a saturated straight or branched carbon chain in which one or more hydrogen atoms are replaced by halogen atoms, e.g. by fluorine, chlorine, bromine or iodine. Preferably, the chain comprises from 1 to 10 carbon atoms, i.e. 1, 2, 3, 4, 5, 6, 7, 8, 9 or 10. In particular, "haloalkyl" refers to —$CH_2F$, —$CHF_2$, —$CF_3$, —$C_2H_4F$, —$C_2H_3F_2$, —$C_2H_2F_3$, —$C_2HF_4$, —$C_2F_5$, —$C_3H_6F$, —$C_3H_5F_2$, —$C_3H_4F_3$, —$C_3H_3F_4$, —$C_3H_2F_5$, —$C_3HF_6$, —$C_3F_7$, —$CH_2Cl$, —$CHCl_2$, —$CCl_3$, —$C_2H_4Cl$, —$C_2H_3Cl_2$, —$C_2H_2Cl_3$, —$C_2HCl_4$, —$C_2Cl_5$, —$C_3H_6Cl$, —$C_3H_5Cl_2$, —$C_3H_4Cl_3$, —$C_3H_3Cl_4$, —$C_3H_2Cl_5$, —$C_3HCl_6$, and —$C_3Cl_7$. Haloalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl etc. The terms "cycloalkyl" and "heterocycloalkyl" are also meant to include bicyclic, tricyclic and polycyclic versions thereof. If bicyclic, tricyclic or polycyclic rings are formed, it is preferred that the respective rings are connected to each other at two adjacent carbon atoms, however, alternatively the two rings are connected via the same carbon atom, i.e. they form a spiro ring system or they form "bridged" ring systems, preferably tricycle[$3.3.1.1^{3,7}$]decan. The term "heterocycloalkyl" preferably refers to a saturated ring having five members of which at least one member is an N, O or S atom and which optionally contains one additional O or one additional N; a saturated ring having six members of which at least one member is an N, O or S atom and which optionally contains one additional O or one additional N or two additional N atoms; or a saturated bicyclic ring having nine or ten members of which at least one member is an N, O or S atom and which optionally contains one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Examples of cycloalkyl include cyclopropyl, cyclobutyl, cyclopentyl, cyclohexyl, cycloheptyl, spiro[3,3]heptyl, spiro [3,4]octyl, spiro[4,3]octyl, spiro[3,5]nonyl, spiro[5,3]nonyl, spiro[3,6]decyl, spiro[6,3]decyl, spiro[4,5]decyl, spiro[5,4] decyl, bicyclo[2.2.1]heptyl, bicyclo[2.2.2]octyl, adamantyl, and the like. Examples of heterocycloalkyl include 1-(1,2, 5,6-tetrahydropyridyl), 1-piperidinyl, 2-piperidinyl, 3-piperidinyl, 4-morpholinyl, 3-morpholinyl, 1,8-diazo-spiro[4,5] decyl, 1,7-diazo-spiro[4,5]decyl, 1,6-diazo-spiro[4,5]decyl, 2,8-diazo-spiro[4,5]decyl, 2,7-diazo-spiro[4,5]decyl, 2,6-diazo-spiro[4,5]decyl, 1,8-diazo-spiro[5,4]decyl, 1,7 diazo-spiro[5,4]decyl, 2,8-diazo-spiro[5,4]decyl, 2,7-diazo-spiro [5,4]decyl, 3,8-diazo-spiro[5,4]decyl, 3,7-diazo-spiro[5,4] decyl, 1,4-diazabicyclo[2.2.2]oct-2-yl, tetrahydro furan-2-yl, tetrahydrofuran-3-yl, tetrahydrothien-2-yl, tetrahydrothien-3-yl, 1-piperazinyl, 2-piperazinyl, and the like.

The term "alicyclic system" refers to mono, bicyclic, tricyclic or polycyclic version of a cycloalkyl or heterocycloalkyl comprising at least one double and/or triple bond. However, an alicyclic system is not aromatic or heteroaromatic, i.e. does not have a system of conjugated double bonds/free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Thus, the "cycloalkenyl" as defined below is a preferred embodiment of an alicyclic ring system. Alicyclic systems are optionally substituted.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl. The aryl group is optionally substituted.

The term "aralkyl" refers to an alkyl moiety, which is substituted by aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl, propyl, iso-propyl, butyl, iso-butyl, sec-butyl, tert-butyl, pentyl, hexyl, heptyl, octyl. The aralkyl group is optionally substituted at the alkyl and/or aryl part of the group. Preferably the aryl attached to the alkyl has the meaning phenyl, naphthyl or anthracenyl.

The term "heteroaryl" preferably refers to a five or six-membered aromatic monocyclic ring wherein at least one of the carbon atoms is replaced by 1, 2, 3, or 4 (for the five membered ring) or 1, 2, 3, 4, or 5 (for the six membered ring) of the same or different heteroatoms, preferably selected from O, N and S; an aromatic bicyclic ring system with 8 to 12 members wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system with 13 to 16 members wherein 1, 2, 3, 4, 5, or 6 carbon atoms of the 13, 14, 15, or 16 carbon atoms have been replaced with the same or different heteroatoms, preferably selected from O, N and S. Examples are furanyl, thiophenyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indoyl, isoindoyl, benzothiophenyl, 2-benzothiophenyl, 1H-indazolyl, benzimidazolyl, benzoxazolyl, indoxazinyl, 2,1-benzosoxazoyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, quinolinyl, 1,2,3-benzotriazinyl, or 1,2,4-benzotriazinyl.

The term "heteroaralkyl" refers to an alkyl moiety, which is substituted by heteroaryl, wherein alkyl and heteroaryl have the meaning as outlined above. An example is the 2-alkylpyridinyl, 3-alkylpyridinyl, or 2-methylpyridinyl radical. Preferably, in this context the alkyl chain comprises from 1 to 8 carbon atoms, i.e. 1, 2, 3, 4, 5, 6, 7, or 8, e.g. methyl, ethyl, propyl, iso-propyl, butyl, iso-butyl, sec-butyl, tert-butyl, pentyl, hexyl, heptyl, octyl. The heteroaralkyl group is optionally substituted at the alkyl and/or heteroaryl part of the group. Preferably the heteroaryl attached to the alkyl has the meaning oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indoyl, isoindoyl, benzothiophenyl, 2-benzothiophenyl, 1H-indazolyl, benzimidazolyl, benzoxazolyl, indoxazinyl, 2,1-benzosoxazoyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, or 1,2,4-benzotriazinyl.

The terms "alkenyl" and "cycloalkenyl" refer to olefinic unsaturated carbon atoms containing chains or rings with one or more double bonds. Examples are propenyl and cyclohexenyl. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, heptenyl, octenyl. Preferably the cycloalkenyl ring comprises from 3 to 8 carbon atoms, i.e. 3, 4, 5, 6, 7, or 8, e.g. 1-cyclopropenyl, 2-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl, cycloheptenyl, cyclooctenyl.

The terms "heteroalkenyl" and "heterocycloalkenyl" refer to unsaturated versions of "heteroalkyl" and "heterocycloalkyl", respectively. Thus, the term "heteroalkenyl" refers to an unsaturated straight or branched carbon chain. Preferably, the chain comprises from 1 to 9 carbon atoms, i.e. 1, 2, 3, 4, 5, 6, 7, 8, 9, which is interrupted one or more times, e.g. 1, 2, 3, 4, 5, with the same or different heteroatoms. Preferably, the heteroatoms are selected from O, S, and N. In case that one or more of the interrupting heteroatoms is N, the N may be present as an —NR'— moiety, wherein R' is hydrogen or hydrocarbon (e.g. $C_1$ to $C_6$ alkyl), or it may be present as an =N— or —N= group, i.e. the nitrogen atom can form a double bond to an adjacent C atom or to an adjacent, further N atom. "Heteroalkenyl" groups are optionally substituted. The term "heterocycloalkenyl" represents a cyclic version of "heteroalkenyl" with preferably 3, 4, 5, 6, 7, 8, 9 or 10 atoms forming a ring. The term "heterocycloalkenyl" is also meant to include bicyclic, tricyclic and polycyclic versions thereof. If bicyclic, tricyclic or polycyclic rings are formed, it is preferred that the respective rings are connected to each other at two adjacent atoms. These two adjacent atoms can both be carbon atoms; or one atom can be a carbon atom and the other one can be a heteroatom; or the two adjacent atoms can both be heteroatoms. However, alternatively the two rings are connected via the same carbon atom, i.e. they form a spiro ring system or they form "bridged" ring systems. The term "heterocycloalkenyl" preferably refers to an unsaturated ring having five members of which at least one member is an N, O or S atom and which optionally contains one additional O or one additional N; an unsaturated ring having six members of which at least one member is an N, O or S atom and which optionally contains one additional O or one additional N or two additional N atoms; or an unsaturated bicyclic ring having nine or ten members of which at least one member is an N, O or S atom and which optionally contains one, two or three additional N atoms. "Heterocycloalkenyl" groups are optionally substituted. Additionally, for heteroalkenyl and heterocycloalkenyl, a heteroatom can occupy the position at which the heterocycle is attached to the remainder of the molecule.

The term "aralkenyl" refers to an alkenyl moiety, which is substituted by aryl, wherein alkenyl and aryl have the meaning as outlined above.

The term "heteroaralkenyl" refers to an alkenyl moiety, which is substituted by heteroaryl, wherein alkenyl and heteroaryl have the meaning as outlined above.

The term "alkynyl" refers to unsaturated carbon atoms containing chains or rings with one or more triple bonds. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, heptynyl, octynyl.

The terms "heteroalkynyl", "cycloalkynyl", and "heterocycloalkynyl" refer to moieties that basically correspond to "heteroalkenyl", "cycloalkenyl", and "heterocycloalkenyl", respectively, as defined above but differ from "heteroalkenyl", "cycloalkenyl", and "heterocycloalkenyl" in that at least one double bond is replaced by a triple bond.

In one embodiment, carbon atoms or hydrogen atoms in alkyl, cycloalkyl, aryl, aralkyl, alkenyl, cycloalkenyl, alkynyl radicals may be substituted independently from each other with one or more elements selected from the group consisting of O, S, N or with groups containing one or more elements, i.e. 1, 2, 3, 4, 5, 6, or more selected from the group consisting of O, S, and N.

Embodiments include alkoxy, cycloalkoxy, aryloxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, alkynylamino radicals.

Other embodiments include hydroxyalkyl, hydroxycycloalkyl, hydroxyaryl, hydroxyaralkyl, hydroxyalkenyl, hydroxycycloalkenyl, hydroxyalkynyl, mercaptoalkyl, mercaptocycloalkyl, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, aminoalkynyl radicals.

In another embodiment, one or more hydrogen atoms, e.g. 1, 2, 3, 4, 5, 6, 7, or 8 hydrogen atoms in alkyl, heteroalkyl, cycloalkyl, heterocycloalkyl, alicyclic system, aryl, aralkyl, heteroaryl, heteroaralkyl, alkenyl, cycloalkenyl, heteroalkenyl, heterocycloalkenyl, alkynyl radicals may be substituted independently from each other with one or more halogen atoms, e.g. Cl, F, or Br. One preferred radical is the trifluoromethyl radical.

If two or more radicals can be selected independently from each other, then the term "independently" means that the radicals may be the same or may be different.

The term "optionally substituted" in each instance if not further specified refers to halogen (in particular F, Cl, Br, or I), —NO$_2$, —CN, —OR'", —NR'R", —COOR'", —CONR'R", —NR'COR", —NR"COR'", —NR'CONR'R", —NR'SO$_2$E, —COR'"; —SO$_2$NR'R", —OOCR'", —CR'"R""OH, —R'"OH, and -E;

R' and R" is each independently selected from the group consisting of hydrogen, alkyl, alkenyl, alkynyl, cycloalkyl, heterocycloalkyl, aryl, aralkyl, and heteroaryl or together form a heteroaryl, or heterocycloalkyl;

R'" and R"" is each independently selected from the group consisting of hydrogen, alkyl, alkenyl, alkynyl, cycloalkyl, heterocycloalkyl, alkoxy, aryl, aralkyl, heteroaryl, and —NR'R";

E is selected from the group consisting of alkyl, alkenyl, alkynyl, cycloalkyl, alkoxy, alkoxyalkyl, heterocycloalkyl, an alicyclic system, aryl and heteroaryl; optionally substituted.

"r.t." is an abbreviation for room temperature.

"iPr" is an abbreviation for an isopropyl group, i.e. for —CH(CH$_3$)$_2$.

"Pharmaceutically acceptable" means approved by a regulatory agency of the Federal or a state government or listed in the U.S. Pharmacopeia (United States Pharmacopeia-33/National Formulary-28 Reissue, published by the United States Pharmacopeial Convention, Inc., Rockville Md., publication date: April 2010) or other generally recognized pharmacopeia for use in animals, and more particularly in humans.

The term "pharmaceutically acceptable salt" refers to a salt of a compound of the present invention. Suitable pharmaceutically acceptable salts of the compound of the present invention include acid addition salts which may, for example, be formed by mixing a solution of a compound described herein or a derivative thereof with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxyethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I, II, III, IV, V, or VI. A prodrug is an active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art. For a general discussion of prodrugs involving esters, see Svensson L. A. and Tunek A. (1988) Drug Metabolism Reviews 19(2): 165-194 and Bundgaard H. "Design of Prodrugs", Elsevier Science Ltd. (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard H. et al. (1989) J. Med. Chem. 32(12): 2503-2507). Also, drugs containing an acidic NH group, such as imidazole, imide, indole and the like, have been masked with N-acyloxymethyl groups (Bundgaard H. "Design of Prodrugs", Elsevier Science Ltd. (1985)). Hydroxy groups have been masked as esters and ethers. EP 0 039 051 A2 discloses Mannich-base hydroxamic acid prodrugs, their preparation and use.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, a "patient" means any mammal or bird that may benefit from a treatment with the compounds described herein. Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in a subject for a certain amount of time. For example, if a compound described herein is administered to a subject with the aim of preventing a disease or disorder, said disease or disorder is prevented from occurring at least on the day of administration and preferably also on one or more days (e.g. on 1 to 30 days; or on 2 to 28 days; or on 3 to 21 days; or on 4 to 14 days; or on 5 to 10 days) following the day of administration.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The term "carrier", as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice flour, chalk, silica gel, sodium stearate, glycerol mono stearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous, unless clearly indicated to the contrary.

In a first aspect the present invention is directed to a compound of the general formula (I):

(I)

wherein
$R^4$ is selected from the group consisting of
(a) hydrogen;
(b) a $C_1$-$C_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(c) a $C_3$ to $C_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen, a $C_1$-$C_4$ alkyl group,
   an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
   a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, (d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

$R^1$ is selected from the group consisting of
hydrogen,
—$(CH_2)_n$—$NR^2$—X—$R^3$, wherein n is 1, 2 or 3;
—$(CH_2)_n$—$NH_2$, wherein n is 2 or 3; and
—$(CH_2)_n$—O—$R^5$, wherein $R^5$ is a hydrogen atom and n is 2 or 3, or $R^5$ is a $C_1$-$C_4$ alkyl group and n is 1, 2 or 3;
wherein
$R^2$ is hydrogen or a $C_1$ to $C_3$ alkyl group;
X is $SO_2$ or CO;
$R^3$ is selected from the group consisting of:
  (i) an aralkyl group, the alkyl moiety having 1 to 6 carbon atoms, and the aryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
  (ii) an aralkenyl group, the alkenyl moiety having 2 to 6 carbon atoms, and the aryl moiety being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
  (iii) an aryl group, optionally being substituted by one or more substituents selected from the group consisting of a halogen atom, —$NH_2$, —$NO_2$, —CN, —OH, a $C_1$-$C_4$ alkoxy group and —$COOR^5$, wherein $R^5$ is a hydrogen atom or a $C_1$-$C_4$ alkyl group, and wherein two adjacent substituents of the aryl group may be connected to form a methylenedioxy group or an ethylenedioxy group;
  (iv) a heteroaryl group, optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl group may be connected to form a methylenedioxy group or an ethylenedioxy group;
  (v) a heteroaralkyl group, the alkyl moiety having 1 to 6 carbon atoms and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group; and
  (vi) a heteroaralkenyl group, the alkenyl moiety having 2 to 6 carbon atoms, and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group;
and
$R^{13}$ is selected from the group consisting of
(a) hydrogen;
(b) a $C_1$-$C_6$ alkyl group, optionally substituted by one or more substituents selected from the group consisting of halogen, —CN, —$NH_2$, —$NR^{11}R^{12}$, —NH—CO—$R^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein R$^{12}$ is a C$_1$-C$_4$ alkyl group; and
wherein R$^{11}$ is selected from the group consisting of
  hydrogen,
  a C$_1$-C$_4$ alkyl group,
    an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and
    a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;

(c) a C$_3$ to C$_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein R$^{12}$ is a C$_1$-C$_4$ alkyl group; and
wherein R$^{11}$ is selected from the group consisting of
  hydrogen,
  a C$_1$-C$_4$ alkyl group,
    an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and
    a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, (d) an aryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(f) a heteroaryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

with the proviso that at least one of R$^1$, R$^4$ or R$^{13}$ is not hydrogen;

or a salt thereof or a solvate thereof or a prodrug thereof.

As indicated above, the first aspect of the present invention is directed to compounds according to general formula (I) with the proviso that at least one of R$^1$, R$^4$ or R$^{13}$ is not hydrogen. This proviso means that at least one of the C-1 atom, the C-3 atom or the C-4 atom of the 1-deoxy fucose derivative carries a substituent different from hydrogen.

In preferred embodiments, the first aspect of the present invention is directed to compounds according to general formula (I) as defined above with the proviso that at least one of R$^4$ or R$^{13}$ is not hydrogen. This proviso means that at least one of the C-3 atom or the C-4 atom of the 1-deoxy fucose derivative carries a substituent different from hydrogen.

In one embodiment of the first aspect, the compound has a structure according to general formula (II)

In another embodiment of the first aspect, the compound has a structure according to general formula (III)

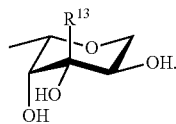
(III)

In yet another embodiment of the first aspect, the compound has a structure according to general formula (IV)

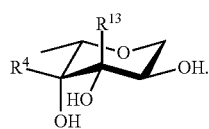
(IV)

In a second aspect the present invention is directed to a compound having a structure according to general formula (V) or general formula (VI)

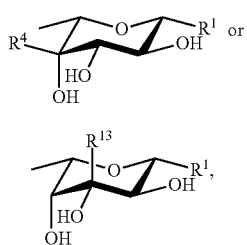
(V)

(VI)

wherein
$R^4$ is selected from the group consisting of
(b) a $C_1$-$C_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
  hydrogen,
  a $C_1$-$C_4$ alkyl group,
  an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
  a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(c) a $C_3$ to $C_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
  hydrogen,
  a $C_1$-$C_4$ alkyl group,
  an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
  a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H,
(d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

$R^1$ is selected from the group consisting of hydrogen, —$(CH_2)_n$—$NR^2$—X—$R^3$, —$(CH_2)_n$—$NH_2$, and —$(CH_2)_n$—O—$R^5$, wherein $R^5$ is a hydrogen atom or a $C_1$-$C_4$ alkyl group;

n is 1, 2 or 3;

$R^2$ is hydrogen or a $C_1$ to $C_3$ alkyl group;

X is $SO_2$ or CO;

$R^3$ is selected from the group consisting of:
  (i) an aralkyl group, the alkyl moiety having 1 to 6 carbon atoms, and the aryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
  (ii) an aralkenyl group, the alkenyl moiety having 2 to 6 carbon atoms, and the aryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group;
  (iii) an aryl group, optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl group may be connected to form a methylenedioxy group or an ethylenedioxy group;
  (iv) a heteroaryl group, optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the heteroaryl group may be connected to form a methylenedioxy group or an ethylenedioxy group;
  (v) a heteroaralkyl group, the alkyl moiety having 1 to 6 carbon atoms and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group; and
  (vi) a heteroaralkenyl group, the alkenyl moiety having 2 to 6 carbon atoms, and the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$ wherein $R^5$ is a hydrogen atom or a $C_1$-$C_4$ alkyl group;

and $R^{13}$ is selected from the group consisting of (b) a $C_1$-$C_6$ alkyl group, optionally substituted by one or more substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;
  wherein $R^{12}$ is a $C_1$-$C_4$ alkyl group; and
  wherein $R^{11}$ is selected from the group consisting of
    hydrogen,
    a $C_1$-$C_4$ alkyl group,
    an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
    a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$;

(c) a $C_3$ to $C_7$ cycloalkyl group, optionally substituted by one or more substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;
  wherein $R^{12}$ is a $C_1$-$C_4$ alkyl group; and
  wherein $R^{11}$ is selected from the group consisting of
    hydrogen,
    a $C_1$-$C_4$ alkyl group,
    an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
    a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, (d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

or a salt thereof or a solvate thereof or a prodrug thereof.

In some embodiments of the first or second aspect, $R^4$ is selected from the group consisting of (b) a $C_1$-$C_6$ alkyl group (e.g. methyl, ethyl, propyl, butyl, pentyl, or hexyl), optionally substituted by one, two or three substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;

wherein $R^{12}$ is a $C_1$-$C_4$ alkyl group (e.g. methyl, ethyl, propyl, butyl); and wherein $R^{11}$ is selected from the group consisting of
hydrogen,
a $C_1$-$C_4$ alkyl group (e.g. methyl, ethyl, propyl, or butyl),
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$;

(c) a $C_3$ to $C_7$ cycloalkyl group, optionally substituted by one, two or three substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, —$NO_2$, -triazole-$R^{11}$, and —$CH_2$—$R^{11}$;

wherein $R^{12}$ is a $C_1$-$C_4$ alkyl group (e.g. methyl, ethyl, propyl, butyl); and wherein $R^{11}$ is selected from the group consisting of
hydrogen,
a $C_1$-$C_4$ alkyl group (e.g. methyl, ethyl, propyl, butyl),
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$;

(d) an aryl group, optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(e) an aralkyl group, the alkyl moiety having 1 to 6 carbon atoms (e.g. 1, 2, 3, 4, 5 or 6 carbon atoms), and the aryl moiety optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group;

(f) a heteroaryl group, optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group; and (g) a heteroaralkyl group, the alkyl moiety having 1 to 6 carbon atoms (e.g. 1, 2, 3, 4, 5 or 6 carbon atoms), and the heteroaryl moiety optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —$NH_2$, —$NHR^{13}$ with $R^{13}$ being a $C_1$-$C_4$ alkyl group, —$NR^{13}R^{14}$ with $R^{13}$ and $R^{14}$ each being independently from each other a $C_1$-$C_4$ alkyl group, —$NO_2$, —CN, —COOH, —$COOR^{13}$ with $R^{13}$ being a $C_1$-$C_4$ alkyl group, and —$SO_3H$; and wherein two adjacent substituents of the aryl group may be connected to form a methylenedioxy group or an ethylenedioxy group.

In some embodiments of the first or second aspect, the aryl moiety or the aryl group of $R^4$ is a phenyl group or a naphthyl group.

In some embodiments of the first or second aspect, the heteroaryl moiety or the heteroaryl group of $R^4$ is selected from the group consisting of
(i) a five-membered aromatic monocyclic ring, wherein 1, 2, 3, or 4 of the ring atoms are the same or different heteroatoms, said heteroatoms being selected from O, N, or S;
(ii) a six-membered aromatic monocyclic ring, wherein 1, 2, 3, 4, or 5 of the ring atoms are the same or different heteroatoms, said heteroatoms being selected from O, N, or S; and
(iii) an aromatic bicyclic ring system with 8 to 12 members, wherein 1, 2, 3, 4, 5, or 6 of the ring atoms are the same or different heteroatoms, said heteroatoms being selected from O, N, or S.

In some embodiments of the first or second aspect, $R^4$ is selected from the group consisting of methyl, ethyl, propyl, butyl, 2-isopentyl, hexyl, phenyl, benzyl, cyclohexyl, —$CH_2$—CN, —$CH_2$—$CH_2$—$NH_2$, —$CH_2$—$CH_2$—N($CH_3$)$_2$, —$CH_2$—$CH_2$—NH—CO—$CH_3$, —$CH_2$—$CH_2$—NH—$SO_2$—$CH_3$, and —$CH_2$—$CH_2$—O—$CH_3$.

In some embodiments of the first or second aspect, $R^{13}$ is a $C_1$-$C_6$ alkyl group, optionally substituted by one, two or three substituents selected from the group consisting of halogen, —CN, —$NH_2$, —$NR^{11}R^{12}$, —NH—CO—$R^{11}$, —NH—$SO_2$—$R^{11}$, —$OR^{11}$, —$SR^{11}$, —$SO_2R^{11}$, —$COOR^{11}$, and —$NO_2$; wherein $R^{11}$ is selected from the group consisting of hydrogen and a $C_1$-$C_4$ alkyl group, and wherein $R^{12}$ is a $C_1$-$C_4$ alkyl group.

In some embodiments of the first or second aspect, $R^{13}$ is selected from the group consisting of methyl, ethyl, —$CF_3$, —$CH_2$—$NH_2$, —$CH_2$—NH—CO-iPr, and —$CH_2$—NH—$SO_2$-iPr.

In some embodiments of the first or second aspect, n is 1 and/or $R^2$ is a hydrogen atom.

In some embodiments of the first or second aspect, the aryl moiety, the heteroaryl moiety, the aryl group or the heteroaryl group of $R^3$ may have one or more substituents selected from the group consisting of a halogen atom, —$NH_2$, —$NO_2$ and a methoxy group, or two adjacent substituents of the aryl moiety or the aryl group may be connected to form a methylenedioxy group or an ethylenedioxy group.

In some embodiments of the first or second aspect, the aryl moiety or the aryl group of $R^3$ is a phenyl group or a naphthyl group.

In some embodiments of the first or second aspect, the X is $SO_2$.

In some embodiments of the first or second aspect, the X is C=O.

In some embodiments of the first or second aspect, X is $SO_2$ and $R^3$ is an aryl or heteroaryl group, optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl group or the heteroaryl group may be connected to form a methylenedioxy group or an ethylenedioxy group;
wherein the aryl group is preferably phenyl, naphthyl or anthracenyl; and
wherein the heteroaryl group is preferably a five or six-membered aromatic monocyclic ring, wherein at least one of the carbon atoms is replaced by 1, 2, 3, or 4 (for the five membered ring) or 1, 2, 3, 4, or 5 (for the six membered ring) of the same or different heteroatoms, preferably selected from O, N and S.

In some embodiments of the first or second aspect, X is C=O and $R^3$ is
an aralkenyl group, the alkenyl moiety having 2 carbon atoms, the aryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group, wherein the aryl group is preferably phenyl, naphthyl or anthracenyl; or
a heteroaralkenyl group, the alkenyl moiety having 2 carbon atoms, the heteroaryl moiety optionally being substituted by one or more substituents selected from the group consisting of a halogen atom, —$NH_2$, —$NO_2$, —CN, —OH, a $C_1$-$C_4$ alkyl group, a $C_1$-$C_4$ alkoxy group and —$COOR^5$, wherein $R^5$ is a hydrogen atom or a $C_1$-$C_4$ alkyl group, and wherein two adjacent substituents of the heteroaryl moiety may be connected to form a methylenedioxy group or an ethylenedioxy group, wherein the heteroaryl group is preferably a five or six-membered aromatic monocyclic ring, wherein at least one of the carbon atoms is replaced by 1, 2, 3, or 4 (for the five membered ring) or 1, 2, 3, 4, or 5 (for the six membered ring) of the same or different heteroatoms, preferably selected from O, N and S.

In some embodiments of the first or second aspect, n is 1.

In some embodiments of the first or second aspect, the heteroaryl group of $R^{11}$ is selected from the group consisting of
(i) a five-membered aromatic monocyclic ring, wherein 1, 2, 3, or 4 of the ring atoms are the same or different heteroatoms, said heteroatoms being selected from O, N, or S;
(ii) a six-membered aromatic monocyclic ring, wherein 1, 2, 3, 4, or 5 of the ring atoms are the same or different heteroatoms, said heteroatoms being selected from O, N, or S; and
(iii) an aromatic bicyclic ring system with 8 to 12 members, wherein 1, 2, 3, 4, 5, or 6 of the ring atoms are the same or different heteroatoms, said heteroatoms being selected from O, N, or S.

In a third aspect the present invention is directed to a pharmaceutical composition comprising the compound according to the first aspect or the second aspect, and optionally comprising one or more constituents selected from the group consisting of a pharmaceutically acceptable carrier, a diluent, an excipient and an anti-bacterial therapeutic agent.

In a fourth aspect the present invention is directed to the compound according to the first aspect or the second aspect for use in medicine.

In a fifth aspect the present invention is directed to the compound according to the first aspect or the second aspect, optionally in combination with one or more anti-bacterial therapeutic agent(s), for use in prophylaxis or treatment of *Pseudomonas aeruginosa* infections in a patient.

In a sixth aspect the present invention is directed to the compound according to the first aspect or the second aspect, optionally in combination with one or more anti-bacterial therapeutic agent(s), for use in prophylaxis or treatment of *Pseudomonas aeruginosa*-associated respiratory tract infections in a patient suffering from cystic fibrosis.

The following examples and figures are merely illustrative of the present invention and should not be construed to limit the scope of the invention as indicated by the appended claims in any way.

EXAMPLES

1. Chemical Synthesis 1.1 Materials and Methods

Thin layer chromatography (TLC) was performed using silica gel 60 coated aluminum sheets containing fluorescence indicator (Merck KGaA, Darmstadt, Germany) using UV light (254 nm) and by charring either in anisaldehyde solution (1% v/v 4-methoxybenzaldehyde, 2% v/v concentrated $H_2SO_4$ in EtOH), in aqueous KMnO4 solution or in a molybdate solution (a 0.02 M solution of ammonium cerium sulfate dihydrate and ammonium molybdate tetrahydrate in aqueous 10% $H_2SO_4$) with heating. Medium pressure liquid chromatography (MPLC) was performed on a Teledyne Isco Combiflash Rf200 system using pre-packed silica gel 60 columns from Teledyne Isco, SiliCycle or Macherey-Nagel. Commercial chemicals and solvents were used without further purification. Deuterated solvents were purchased from Eurisotop (Saarbrucken, Germany). Nuclear magnetic resonance (NMR) spectroscopy was performed on a Bruker Avance III 400 (or 500) UltraShield spectrometer at 400 (or 500) MHz ($^1H$) and 101 (or 126) MHz ($^{13}C$). Chemical shifts are given in ppm and were calibrated on residual solvent peaks as internal standard (see: H. E. Gottlieb, V. Kotlyar, A. Nudelman, *J Org Chem* 1997, 62, 7512-7515). Multiplicities were specified as s (singlet), d (doublet), t (triplet) or m (multiplet). The signals were assigned with the help of $^1H$, $^1H$-COSY, DEPT-135-edited $^1H$, $^{13}C$-HSQC and $^1H$, $^{13}C$-HMBC and $^1H$, $^1H$-NOESY experiments. Mass spectra were obtained on a Bruker amaZon SL spectrometer and high resolution mass spectra on a Bruker micrOTOF II ESI spectrometer and the data were analyzed using Data-Analysis from Bruker. 1-deoxy-L-fucose was synthesized as reported previously by Sommer et al. (R. Sommer, T. E. Exner, A. Titz, *PloS ONE* 2014, 9, e112822).

Figure 1B:
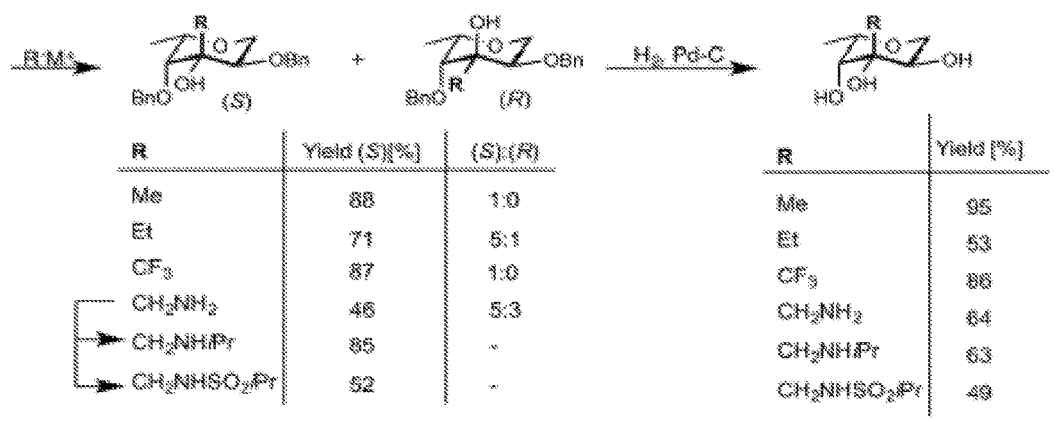
Figure 1B:
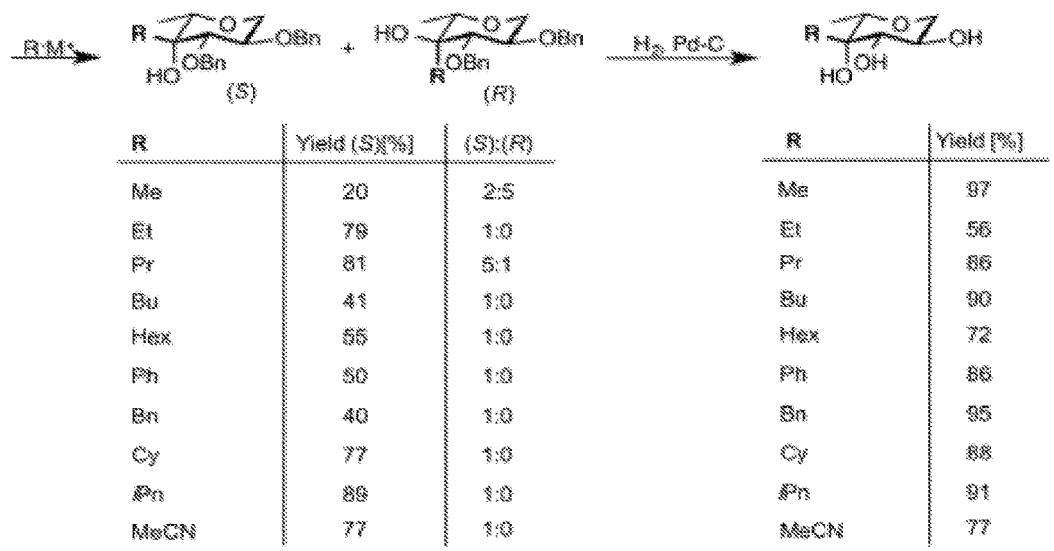

3C- and 4C-modified 1-deoxy fucose derivatives were synthetized according to the general scheme shown in FIG. 1. Details of the synthesis are as follows:

1.2 Chemical Synthesis of 1-deoxy-2,3-di-O-benzyl-L-fuco-3-ulose and 1-deoxy-2,3-di-O-benzyl-L-fuco-4-ulose 1.2.1 1-deoxy-3,4-O-benzylidene-L-fucose

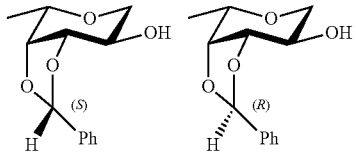

1-deoxy-L-fucose (315 mg, 2.13 mmol) was dissolved in DMF (14 mL) and to the solution were added camphorsulfonic acid (50 mg, 0.21 mmol) and benzaldehyde dimethyl acetal (1 mL, 6.38 mmol). The mixture was stirred at r.t. for 19 h. After triethylamin (30 μL) was added, the solvent was removed in vacuo and purified by MPLC (PE to PE/EtOAc=2:1) to give (S/R)-3,4-O-benzylidene-1-deoxy-L-fucose (442 mg, 1.87 mmol, 88%) as colorless solids (S-isomer/R-isomer=1/1.5). $^1H$ NMR (400 MHz, Methanol-$d_4$) S-isomer: δ 7.59-7.29 (m, 5H, C$\underline{H}_{benzylidene}$), 5.91 (s, 1H, OOC$\underline{H}_{benzylidene}$), 4.15 (dd, J=6.1, 2.3 Hz, 1H, H-4), 4.08 (t, J=6.5 Hz, 1H), 3.94-3.68 (m, 3H), 3.23-3.10 (m, 1H, CH$_2$), 1.36 (d, J=6.6 Hz, 3H, CH$_3$); R-isomer: δ 7.59-7.29 (m, 5H, H-Ph), 6.10 (s, 1H, H-benzylidene), 4.24 (dd, J=6.9, 5.2 Hz, 1H, H-3), 4.05 (dd, J=5.4, 2.0 Hz, 1H, H-4), 3.94-3.68 (m, 3H, H-2, H-5, H-1$_{equatorial}$), 3.23-3.10 (m, 1H, H-1$_{axial}$), 1.32 (d, J=6.6 Hz, 3H, H-6). $^{13}C$ NMR (101 MHz, Methanol-$d_4$) δ 140.9 ($\underline{C}_{benzylidene}$), 139.4 ($\underline{C}H_{benzylidene}$), 130.2 ($\underline{C}H_{benzylidene}$), 129.9 ($\underline{C}H_{benzylidene}$), 129.3 (2×$\underline{C}H_{benzylidene}$), 129.2 ($\underline{C}H_{benzylidene}$), 127.8 ($\underline{C}H_{benzylidene}$), 127.3 ($\underline{C}H_{benzylidene}$), 105.3 (OO$\underline{C}H_{benzylidene}$ (S-isomer)), 104.2 (OO$\underline{C}H_{benzylidene}$ (R-isomer)), 81.8 (C-3(R-isomer)), 80.0 (C-4(S-isomer)), 80.0, 77.6 (C-4(R-isomer)), 73.9, 73.2, 70.4, 69.6, 69.5, 67.2, 17.3 (C-6(R-isomer)), 17.1 (C-6$_3$(S-isomer)). HR-MS calcd. for $C_{13}H_{16}NaO_4^+$: 259.0941; found: 259.0933.

1.2.2
1-deoxy-2-O-benzyl-3,4-O-benzylidene-L-fucose

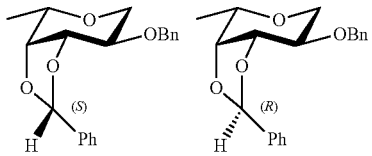

NaH (400 mg, 16.6 mmol) was suspended in DMF (5 mL) and 1-deoxy-3,4-O-benzylidene-L-fucose (1.31 g, 5.53 mmol) in DMF (10 ml) was added at 0° C. After 30 min at 0° C., benzylbromide (2.58 mL, 16.6 mmol) was added and the reaction mixture was stirred at r.t. for 2 h. The mixture was diluted with $H_2O$ (5 mL) and EtOAc (5 mL). The aqueous layer was extracted with EtOAc (3×20 mL). The combined organic phases were dried over $Na_2SO_4$, filtered and the solvent was removed in vacuo. Purification by MPLC (PE to PE/EtOAc=8:1) gave (S/R)-2-O-benzyl-3,4-O-benzylidene-1-deoxy-L-fucose (1.69 g, 5.20 mmol, 94%) as a colorless oil (S-isomer/R-isomer=1.75/1). $^1H$ NMR (400 MHz, Methanol-d₄) S-isomer: δ 7.53-7.22 (m, 10H, CH$_{benzylidene}$, CH$_{benzyl}$), 6.01 (s, 1H, OOCH$_{benzylidene}$), 4.82 (d, J=11.9 Hz, 1H, CH$_2$ $_{benzyl}$), 4.73 (d, J=12.0 Hz, 1H, CH$_2$ $_{benzyl}$), 4.44 (dd, J=7.2, 5.4 Hz, 1H, H-3), 4.07 (dd, J=5.4, 2.0 Hz, 1H, H-4), 4.00 (dd, J=11.4, 5.6 Hz, 1H, H-1$_{equatorial}$), 3.77 (m, 1H, H-5), 3.73 (m, 1H, H-2), 3.21 (dd, J=11.4, 10.3 Hz, H-1$_{axial}$), 1.32 (d, J=6.6 Hz, 3H, H-3); ¹³C NMR (101 MHz, Methanol-d₄) S-isomer: δ 140.7 (C$_{benzylidene}$), 139.7 (C$_{benzyl}$), 130.2 (CH$_{benzylidene}$), 129.3 (CH$_{benzylidene}$), 129.3 (2×CH$_{benzyl}$), 129.0 (CH$_{benzyl}$), 128.7 (CH$_{benzyl}$), 127.4 (CH$_{benzyl}$), 104.3 (OOCH$_{benzylidene}$), 80.9 (C-3), 77.8 (C-4), 74.0 (C-5), 73.9 (C-2), 73.1 (CH$_2$ $_{benzyl}$), 67.5 (C-1), 17.2 (C-6). ¹H NMR (400 MHz, Methanol-d₄) R-isomer: δ 7.53-7.22 (m, 10H, CH$_{benzylidene}$, CH$_{benzyl}$), 5.91 (s, 1H, OOCH$_{benzyl}$), 4.69 (d, J=12.1 Hz, 1H, CH$_2$ $_{benzyl}$), 4.60 (d, J=12.0 Hz, 1H, CH$_2$ $_{benzyl}$), 4.28 (t, J=6.4, 1H, H-3), 4.16 (dd, J=6.2, 2.3 Hz, 1H, H-4), 3.94 (dd, J=11.5, 5.4 Hz, 1H, H-1$_{equatorial}$) 3.89 (td, J=6.6, 2.3 Hz, 1H, H-5), 3.61 (ddd, J=10.2, 6.7, 5.3 Hz, 1H, H-2), 3.20 (dd, J=11.5, 10.3 Hz, 1H, H-1$_{axial}$), 1.37 (d, J=6.6 Hz, 3H, H-6); ¹³C NMR (101 MHz, Methanol-d₄) R-isomer: δ 139.5 (C$_{benzyl}$), 139.2 (C$_{benzylidene}$), 130.0 (CH$_{benzylidene}$), 129.3 (CH$_{benzylidene}$, CH$_{benzyl}$), 129.0 (CH$_{benzyl}$), 128.6 (CH$_{benzyl}$), 127.9 (CH$_{benzylidene}$), 105.3 (OOCH$_{benzylidene}$), 79.2 (C-3), 80.1 (C-4), 73.3 (C-5), 76.9 (C-2), 72.6 (CH$_2$ $_{benzyl}$), 67.4 (C-1), 17.0 (C-6). HR-MS calcd. for C$_{20}$H$_{22}$NaO$_4^+$: 349.1416; found: 349.1357.

1.2.3 1-deoxy-2,3-di-O-benzyl-L-fucose/1-deoxy-2,4-di-O-benzyl-L-fucose

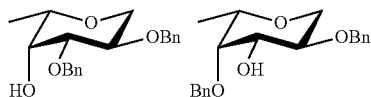

To a solution of 1-deoxy-2-O-benzyl-3,4-O-benzylidene-L-fucose (775 mg, 2.38 mmol) in CH$_2$Cl$_2$/Et$_2$O (8.5 mL/8.5 mL) were added LiAlH$_4$ (379 mg, 9.98 mmol) and AlCl$_3$ (1.18 g, 8.79 mmol) and the mixture was stirred for 3 h at 40° C. The mixture was cooled to r.t. and diluted with EtOAc (20 mL) and H$_2$O (60 mL). The mixture was filtered and the residue washed with (10 mL). The organic layers were washed with H$_2$O (20 mL), dried over Na$_2$SO$_4$, filtered and Et$_2$O the solvent was removed in vacuo. The residue was purified by MPLC (PE to PE/EtOAc=4:1) to give 2,3-di-O-benzyl-1-deoxy-L-fucose (300 mg, 0.914 mmol, 39%) and 1-deoxy-2,4-di-O-benzyl-L-fucose (237 mg, 0.72 mmol, 30%) as colorless solid.

1-deoxy-2,3-di-O-benzyl-L-fucose

¹H NMR (400 MHz, Methanol-d₄) δ 7.48-7.24 (m, 10H, CH$_{benzyl}$), 4.80 (d, J=11.9 Hz, 1H, CH$_2$ $_{benzyl}$), 4.75 (d, J=11.6 Hz, 1H, CH$_2$ $_{benzyl}$), 4.65 (d, J=5.7 Hz, 1H, CH$_2$ $_{benzyl}$), 4.68 (s, 1H, CH$_2$ $_{benzyl}$), 3.96 (dd, J=11.0, 5.6 Hz, 1H, H-1$_{equatorial}$), 3.86 (m, 1H, H-2), 3.86 (m, 1H, H-4), 3.49 (dd, J=9.3, 3.3 Hz, 1H, H-3), 3.46 (dd, J=6.5, 1.1 Hz, 1H, H-5), 3.13 (t, J=10.7 Hz, 1H, H-1$_{axial}$), 1.23 (d, J=6.5 Hz, 3H, H-6); ¹³C NMR (101 MHz, Methanol-d₄) 2,3-derivate: δ 140.0 (C$_{benzyl}$), 140.0 (C$_{benzyl}$), 129.2 (CH$_{benzyl}$), 128.9 (CH$_{benzyl}$), 128.9 (CH$_{benzyl}$), 128.6 (CH$_{benzyl}$), 128.5 (CH$_{benzyl}$), 83.8 (C-3), 76.2 (C-5), 75.3 (C-4), 74.3 (CH$_2$ $_{benzyl}$), 72.2 (CH$_2$ $_{benzyl}$), 70.4 (C-2), 69.2 (C-1), 17.1 (C-6). HR-MS calcd. C$_{20}$H$_{24}$NaO$_4^+$: 351.1567; found: 351.1367.

1-deoxy-2,4-di-O-benzyl-L-fucose

¹H NMR (400 MHz, Methanol-d₄) δ 7.47-7.26 (m, 10H, H-Ph), 4.98 (d, J=11.3 Hz, 1H, CH$_2$ $_{benzyl}$), 4.76 (d, J=11.7 Hz, 1H, CH$_2$ $_{benzyl}$), 4.66 (d, J=3.3 Hz, 1H, CH$_2$ $_{benzyl}$), 4.63 (d, J=3.0 Hz, 1H, CH$_2$ $_{benzyl}$), 3.94 (dd, J=11.1, 5.1 Hz, 1H, H-1$_{equatorial}$), 3.77 (dt, J=9.7, 5.1 Hz, 1H, H-2), 3.70 (dd, J=9.4, 3.2 Hz, 1H, H-3), 3.63 (dd, J=3.2, 1.2 Hz, 1H, H-4), 3.51 (qd, J=6.4, 1.2 Hz, 1H, H-5), 3.10 (dd, J=11.1, 10.0 Hz, 1H, H-1$_{axial}$), 1.14 (d, J=6.4 Hz, 3H, H-3); ¹³C NMR (101 MHz, Methanol-d₄) 2,4-derivate: δ 140.1 (C$_{benzyl}$), 140.0 (C$_{benzyl}$), 129.4 (CH$_{benzyl}$), 129.3 (CH$_{benzyl}$), 129.2 (CH$_{benzyl}$), 129.0 (CH$_{benzyl}$), 128.6 (CH$_{benzyl}$), 128.6 (CH$_{benzyl}$), 81.7 (C-4), 76.8 (C-3), 76.8 (CH$_2$ $_{benzyl}$), 76.7 (C-2), 76.3 (C-5), 74.0 (CH$_2$ $_{benzyl}$), 69.1 (C-1), 17.3 (C-6). HR-MS calcd. C$_{20}$H$_{24}$NaO$_4^+$: 351.1567; found: 351.1551.

1.2.4 1-deoxy-2,3-di-O-benzyl-L-fuco-3-ulose

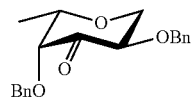

To a solution of 1-deoxy-2,4-di-O-benzyl-L-fucose (1.00 g, 3.04 mmol) in dry CH$_2$Cl$_2$ (60 mL) Dess-Martin periodinane (1.68 g, 3.95 mmol) was added and the reaction mixture was stirred for 2 h at r.t. Sat. NaHCO$_3$ solution (20 mL) and sat. Na$_2$S$_2$O$_3$ solution (20 mL) were added and stirred for 10 min. The aqueous phase was extracted with CH$_2$Cl$_2$ (3×100 mL). The combined organic layers were dried over Na$_2$SO$_4$ and the solvent was removed under reduced pressure to give 980 mg (3.00 mmol, 99%) 1-deoxy-2,4-di-O-benzyl-L-fuco-3-ulose as colorless oil. ¹H NMR (400 MHz, Chloroform-d) δ 7.31-7.16 (m, 10H, CH$_{benzyl}$), 4.62 (d, J=11.8 Hz, 1H, CH$_2$ $_{benzyl}$), 4.50-4.42 (m, 2H, H-2, CH$_2$ $_{benzyl}$), 4.36 (dd, J=15.6, 11.9 Hz, 2H, CH$_2$ $_{benzyl}$), 4.15 (dd, J=10.9, 7.0 Hz, 1H, H-1$_{equatorial}$) 3.68-3.58 (m, 2H, H-5, H-4), 3.36 (dd, J=10.9, 10.0 Hz 1H, H-1$_{axial}$), 1.23 (d, J=6.4 Hz, 3H, H-6); ¹³C NMR (101 MHz, Chloroform-d) δ 206.8 (C-3), 137.2 (C$_{benzyl}$) 136.7 (CH$_{benzyl}$) 128.6 (CH$_{benzyl}$), 128.5 (CH$_{benzyl}$), 128.4 (CH$_{benzyl}$), 128.3 (CH$_{benzyl}$), 128.2 (CH$_{benzyl}$), 128.1 (CH$_{benzyl}$), 84.9 (C-4), 78.1 (C-5), 77.7 (C-2), 72.6 (CH$_2$ $_{benzyl}$), 72.5 (CH$_2$ $_{benzyl}$), 70.7 (C-1), 15.9 (C-6). HR-MS calcd. for C$_{20}$H$_{22}$NaO$_4^+$: 349.1410; found: 349.1413.

1.2.5 1-deoxy-2,3-di-O-benzyl-L-fuco-4-ulose

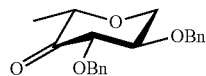

To a solution of 1-deoxy-2,3-di-O-benzyl-L-fucose (100 mg, 0.30 mmol) in dry CH$_2$Cl$_2$ (6 mL) Dess-Martin periodinane (168 mg, 2.35 mmol) was added and the reaction mixture was stirred for 2 h at r.t. Sat. NaHCO$_3$ solution (5 mL) and sat. Na$_2$S$_2$O$_3$ solution (5 mL) were added and stirred for 10 min. The aqueous phase was extracted with CH$_2$Cl$_2$ (3×10 mL). The combined organic layers were dried over Na$_2$SO$_4$ and the solvent was removed in vacuo. The residue was purified by MPLC (PE to PE/EtOAC=5:1) to give 1-deoxy-2,3-di-O-benzyl-L-fuco-4-ulose (84 mg, 0.25 mmol, 86%) as colorless solid. $^1$H NMR (500 MHz, Chloroform-d) δ 7.47-7.42 (m, 2H, C$\underline{H}_{benzyl}$), 7.39-7.28 (m, 8H, C$\underline{H}_{benzyl}$), 5.00 (d, J=11.5 Hz, 1H, C$\underline{H}_{2\ benzyl}$), 4.85-4.79 (m, 1H, C$\underline{H}_{2\ benzyl}$), 4.66 (dd, J=11.5, 2.2 Hz, 2H, C$\underline{H}_{2\ benzyl}$), 4.14 (dd, J=9.0, 0.9 Hz, 1H, H-1$_{equatorial}$), 4.11 (dd, J=11.7, 5.5 Hz, 1H, H-3), 3.89 (ddd, J=10.1, 9.0, 5.5 Hz, 1H, H-2), 3.84 (qd, J=6.5, 1.0 Hz, 1H, H-5), 3.58 (dd, J=11.7, 10.1 Hz, 1H, H-1$_{axial}$), 1.30 (d, J=6.4 Hz, 3H, H-6). $^{13}$C NMR (126 MHz, Chloroform-d) δ 203.06 (C-4), 138.01 ($\underline{C}_{benzyl}$), 137.77 ($\underline{C}_{benzyl}$), 128.57 (C$\underline{H}_{benzyl}$), 128.53 (C$\underline{H}_{benzyl}$), 128.49 (C$\underline{H}_{benzyl}$), 128.17 (C$\underline{H}_{benzyl}$), 128.02 (C$\underline{H}_{benzyl}$), 127.99 (C$\underline{H}_{benzyl}$), 127.96 (C$\underline{H}_{benzyl}$), 86.43 (C-3), 80.08 (C-2), 77.86 (C-5), 73.83 ($\underline{C}H_{2\ benzyl}$), 73.80 ($\underline{C}H_{2\ benzyl}$), 68.33 (C-1), 14.17 (C-6). HR-MS calcd. C$_{20}$H$_{22}$NaO$_4^+$: 349.1410; found: 349.1405.

1.3 General Procedure for Nucleophile Addition

To 1-deoxy-2,3-di-O-benzyl-L-fuco-4-ulose (100 mg, 0.30 mmol) in dry THF (6 mL) the corresponding Grignard or lithium nucleophile (1.5 eq.) was added dropwise at −78° C. under nitrogen atmosphere. The reaction mixture was stirred for 1 h at −78° C. and sat. NH$_4$Cl solution was added. The aqueous phase was extracted with EtOAc, the combined organic layers were dried over Na$_2$SO$_4$ and the solvent removed in vacuo. The residue was purified by MPLC (PE to PE/EtOAc=5:1).

1.3.1 1-deoxy-2,4-di-O-benzyl-3(S)—C-(methyl)-L-fucose

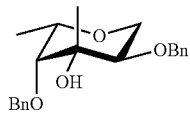

Methyllithium solution (140 μL, 0.225 mmol, 1.6 M in Et$_2$O) was used as nucleophile. Purification of the reaction mixture yielded 1-deoxy-2,4-di-O-benzyl-3(S)—C-(methyl)-L-fucose (45 mg, 0.013 mmol, 88%) as colorless oil. $^1$H NMR (500 MHz, Methanol-d$_4$) δ 7.53-7.15 (m, 10H, C$\underline{H}_{benzyl}$), 4.92 (d, J=11.3 Hz, 1H, C$\underline{H}_{2\ benzyl}$), 4.76 (d, J=11.7 Hz, 1H, C$\underline{H}_{2\ benzyl}$), 4.60 (dd, J=11.5, 3.9 Hz, 2H, C$\underline{H}_{2\ benzyl}$), 3.82-3.75 (m, 2H, H-1$_{equatorial}$, H-2), 3.72 (qd, J=6.4, 1.4 Hz, 1H, H-5), 3.26 (d, J=1.3 Hz, 1H, H-4), 3.23-3.15 (m, 1H, H-1$_{axial}$), 1.30 (s, 3H, H-6), 1.12 (d, J=6.4 Hz, 3H, C$\underline{H}_3$). $^{13}$C NMR (126 MHz, Methanol-d$_4$) δ 140.3 ($\underline{C}_{benzyl}$), 139.9 ($\underline{C}_{benzyl}$), 129.4 (C$\underline{H}_{benzyl}$), 129.3 (C$\underline{H}_{benzyl}$), 128.8 (C$\underline{H}_{benzyl}$), 128.7 (C$\underline{H}_{benzyl}$), 128.6 (C$\underline{H}_{benzyl}$), 86.7 (C-4), 79.2 (C-2), 77.3 ($\underline{C}H_{2\ benzyl}$), 76.0 (C-3), 74.5 (2C, C-5, $\underline{C}H_{2\ benzyl}$), 67.4 (C-1), 19.2 ($\underline{C}H_3$), 17.5 (C-6). ESI-MS calcd. C$_{21}$H$_{26}$NNaO$_4^+$: 365.2; found: 365.2.

1.3.2 1-deoxy-2,4-di-O-benzyl-3(S)—C-(vinyl)-L-fucose and 1-deoxy-2,4-di-O-benzyl-3(R)—C-(vinyl)-6-deoxy-L-gulose

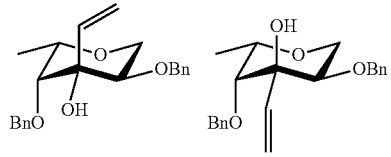

Vinylmagnesium bromide solution (642 μL, 0.45 mmol, 0.7 M in THF) was used as nucleophile. Purification of the reaction mixture yielded 1-deoxy-2,4-di-O-benzyl-3(S)—C-(vinyl)-L-fucose (76 mg, 0.214 mmol, 71%) as colorless oil and 1-deoxy-2,4-di-O-benzyl-3(R)—C-(vinyl)-6-deoxy-L-gulose (17 mg, 0.048 mmol, 16%) as colorless oil.

1-deoxy-2,4-di-O-benzyl-3(S)—C-(vinyl)-L-fucose $^1$H NMR (500 MHz, Methanol-d$_4$) δ 7.49-7.23 (m, 10H, C$\underline{H}_{benzyl}$), 6.37 (dd, J=17.4, 11.1 Hz, 1H, C$\underline{H}_{vinyl}$), 5.63 (dd, J=17.4, 1.6 Hz, 1H, C$\underline{H}_{2\ vinyl}$), 5.41 (dd, J=11.1, 1.7 Hz, 1H, C$\underline{H}_{2\ vinyl}$), 4.99 (d, J=11.3 Hz, 1H, C$\underline{H}_{2\ benzyl}$), 4.77 (d, J=11.7 Hz, 1H, C$\underline{H}_{2\ benzyl}$), 4.63 (t, J=11.9 Hz, 2H, C$\underline{H}_{2\ benzyl}$), 3.91-3.81 (m, 2H, H-1$_{equatorial}$, H-2), 3.75 (qd, J=6.4, 1.5 Hz, 1H, H-5), 3.40-3.39 (m, 1H, H-4), 3.38-3.35 (m, 1H, H-1$_{axial}$), 1.14 (d, J=6.4 Hz, 3H, H-6). $^{13}$C NMR (126 MHz, Methanol-d$_4$) δ 140.2 ($\underline{C}_{benzyl}$), 139.9 ($\underline{C}_{benzyl}$), 138.5 (C$\underline{H}_{vinyl}$), 129.4 (C$\underline{H}_{benzyl}$), 129.2 (C$\underline{H}_{benzyl}$), 128.9 (C$\underline{H}_{benzyl}$), 128.7 (C$\underline{H}_{benzyl}$), 128.6 (C$\underline{H}_{benzyl}$), 117.8 (C$\underline{H}_{2\ vinyl}$), 85.6 (C-4), 79.3 (C-2), 78.0 (C-3), 77.1 ($\underline{C}H_{2\ benzyl}$), 74.3 ($\underline{C}H_{2\ benzyl}$), 74.2 (C-5), 66.7 (C-1), 17.3 (C-6). ESI-MS calcd. C$_{22}$H$_{27}$NNaO$_4^+$: 377.2; found: 377.2.

1-deoxy-2,4-di-O-benzyl-3(R)—C-(vinyl)-6-deoxy-L-gulose $^1$H NMR (500 MHz, Methanol-d$_4$) δ 7.42-7.21 (m, 10H, C$\underline{H}_{benzyl}$), 6.21 (dd, J=17.4, 10.8 Hz, 1H, C$\underline{H}_{vinyl}$), 5.53 (dd, J=17.4, 1.7 Hz, 1H, C$\underline{H}_{2\ vinyl}$), 5.30 (dd, J=10.8, 1.7 Hz, 1H, C$\underline{H}_{2\ vinyl}$), 4.62 (d, J=11.0 Hz, 1H, C$\underline{H}_{2\ benzyl}$), 4.54 (s, 2H, C$\underline{H}_{2\ benzyl}$), 4.50 (d, J=11.0 Hz, 1H, C$\underline{H}_{2\ benzyl}$), 3.99 (qd, J=6.6, 1.3 Hz, 1H, H-5), 3.80-3.71 (m, 2H, H-1$_{equatorial}$, H-2), 3.57 (t, J=10.4 Hz, 1H, H-1$_{axial}$), 3.10 (d, J=1.2 Hz, 1H, H-4), 1.11 (d, J=6.5 Hz, 3H, H-6). $^{13}$C NMR (126 MHz, Methanol-d$_4$) δ 143.0 (C$\underline{H}_{vinyl}$), 139.7 ($\underline{C}_{benzyl}$), 139.4 ($\underline{C}_{benzyl}$), 129.3 (C$\underline{H}_{benzyl}$), 129.3 (C$\underline{H}_{benzyl}$), 129.3 (C$\underline{H}_{benzyl}$), 129.1 (C$\underline{H}_{benzyl}$), 128.8 (C$\underline{H}_{benzyl}$), 128.8 (C$\underline{H}_{benzyl}$), 115.7 (C$\underline{H}_{2\ vinyl}$), 85.8 (C-4), 77.0 ($\underline{C}H_{2\ benzyl}$), 75.9 (C-3), 75.8 (C-2), 74.1 ($\underline{C}H_{2\ benzyl}$), 72.7 (C-5), 65.6 (C-1), 16.9 (C-6). ESI-MS calcd. C$_{22}$H$_{27}$NNaO$_4^+$: 377.2; found: 377.2.

1.3.3 1-deoxy-2,4-di-O-benzyl-3(S)—C-(trifluoromethyl)-L-fucose

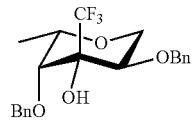

Trifluoromethyltrimethylsilane (225 μL, 2M in THF) were dissolved in dry THF (1 mL) and cooled to 0° C. Tetrabutylammonium fluorine (450 μL, 1M in THF) was added dropwise. This solution was transferred via syringe to a solution of 1-deoxy-2,3-di-O-benzyl-L-fuco-3-ulose (100 mg, 0.30 mmol) in dry THF (3 mL) at 0° C. and stirred to r.t over 20 h. Purification of the reaction mixture yielded 1-deoxy-2,4-di-O-benzyl-3(S)—C-(trifluoromethyl)-L-fucose (103 mg, 0.259 mmol, 87%) as colorless oil.

1-deoxy-2,4-di-O-benzyl-3(S)—C-(trifluoromethyl)-L-fucose $^1$H NMR (500 MHz, Chloroform-d) δ 7.40-7.27 (m, 10H, C$\underline{H}_{benzyl}$), 4.68-4.57 (m, 4H, C$\underline{H}_2$ $_{benzyl}$), 4.18-4.10 (m, 1H, H-5), 4.06 (d, J=4.9 Hz, 1H, H-4), 3.93 (dd, J=12.6, 2.7 Hz, 1H, H-1$_{equatorial}$), 3.75 (t, J=3.4 Hz, 1H, H-2), 3.70-3.65 (m, 1H, H-1$_{axial}$), 1.34 (d, J=6.8 Hz, 3H, H-6). $^{13}$C NMR (126 MHz, Chloroform-d) δ 137.6 ($\underline{C}_{benzyl}$), 137.2 ($\underline{C}_{benzyl}$), 128.7 (C$\underline{H}_{benzyl}$), 128.6 (C$\underline{H}_{benzyl}$), 128.4 (C$\underline{H}_{benzyl}$), 128.4 (C$\underline{H}_{benzyl}$), 128.0 (C$\underline{H}_{benzyl}$), 125.2 (d, J$_{CF}$=287.7 Hz, $\underline{C}$F$_3$), 76.3 (C-2), 75.2 (q, J=26.3 Hz), 74.4 ($\underline{C}$H$_2$ $_{benzyl}$), 74.0 (C-5), 72.5 ($\underline{C}$H$_2$ $_{benzyl}$), 70.1 (C-5), 59.8 (C-1), 14.0 (C-6).

1.3.4 1-deoxy-2,4-di-O-benzyl-3(S)—C-(aminomethyl)-L-fucose and 1-deoxy-2,4-di-O-benzyl-3(R)—C-(aminomethyl)-6-deoxy-L-gulose

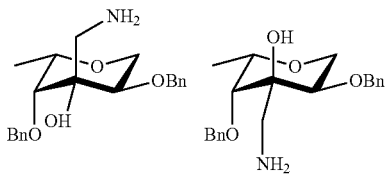

1-deoxy-2,4-di-O-benzyl-L-fuco-3-ulose (120 mg, 0.367 mmol) was dissolved in 2 mL MeOH, 0.6 mL sat. NH$_4$Cl solution and KCN (215 mg, 3.31 mmol) were added at 0° C. and stirred for 10 min. Additional 10 mL sat. NH$_4$Cl solution were added and the aqueous phase was extracted with EtOAc (3×15 mL). The combined organic layers were dried over Na$_2$SO$_4$ and the solvent was removed under reduced pressure. The residue was purified by FC (PE to PE/EtOAc=6:1) to give 0.034 g (0.096 mmol, 26%) 1-deoxy-2,4-di-O-benzyl-3(S)—C-(cyano)-L-fucose as colorless solid ESI-MS calcd. C$_{21}$H$_{23}$NaNO$_4^+$: 376.2; found: 376.2 and 0.074 g (0.210 mmol, 57%) 1-deoxy-2,4-di-O-benzyl-3(R)—C-(cyano)-6-deoxy-L-gulose as colorless oil ESI-MS calcd. C$_{21}$H$_{23}$NaNO$_4^+$: 376.2; found: 376.2. These two compounds were added as a solution in Et$_2$O (0.1 M) in separated approaches to a suspension of LiAH$_4$ (4.5 equiv) in Et$_2$O (1 M) and stirred at r.t. for 1 h. Saturated NaHCO$_3$ solution was added and the aqueous phase was extracted with EtOAc. The combined organic layers were dried over Na$_2$SO$_4$ and solvent was removed under reduced pressure. The residue was purified by MPLC (CH$_2$Cl$_2$/EtOAc=1:1 to CH$_2$Cl$_2$/EtOAc/MeOH=1:1:0.5) to give 0.012 g (0.035 mmol, 35%) 1-deoxy-2,4-di-O-benzyl-3(S)—C-(aminomethyl)-L-fucose as colorless oil and 0.041 g (0.114 mmol, 55%) 1-deoxy-2,4-di-O-benzyl-3(R)—C-(aminomethyl)-6-deoxy-L-gulose as colorless oil.

1-deoxy-2,4-di-O-benzyl-3(S)—C-(aminomethyl)-L-fucose $^1$H NMR (400 MHz, Methanol-d$_4$) δ 7.46-7.20 (m, 10H, C$\underline{H}_{benzyl}$), 4.87 (d, J=11.3 Hz, 1H, C$\underline{H}_2$ $_{benzyl}$), 4.74-4.55 (m, 3H, C$\underline{H}_2$ $_{benzyl}$), 3.89-3.79 (m, H-1, 2H, H-2, H-1$_{equatorial}$), 3.73 (qd, J=6.4, 1.9 Hz, 1H, H-5), 3.48 (d, J=1.9 Hz, 1H, H-4), 3.39-3.32 (m, 1H, H-1$_{axial}$), 3.20 (d, J=13.8 Hz, 1H, C$\underline{H}_2$NH$_2$), 2.80 (d, J=13.8 Hz, 1H, C$\underline{H}_2$NH$_2$), 1.17 (d, J=6.4 Hz, 3H, H-6); $^{13}$C NMR (101 MHz, Methanol-d$_4$) δ 139.8 ($\underline{C}_{benzyl}$), 139.7 (C$\underline{H}_{benzyl}$), 129.4 (C$\underline{H}_{benzyl}$), 129.4 (C$\underline{H}_{benzyl}$), 129.3 (C$\underline{H}_{benzyl}$), 128.9 (C$\underline{H}_{benzyl}$), 128.8 (C$\underline{H}_{benzyl}$), 82.2 (C-4), 79.3 (C-2), 76.8 ($\underline{C}$H$_2$ $_{benzyl}$), 75.7 (C-3), 74.2 ($\underline{C}$H$_2$ $_{benzyl}$), 73.7 (C-5), 65.7 (C-1), 43.3 ($\underline{C}$H$_2$NH$_2$), 16.8 (C-6); HR-MS calcd. for C$_{21}$H$_{28}$NO$_4^+$: 358.2013; found: 358.2004.

1-deoxy-2,4-di-O-benzyl-3(R)—C-(aminomethyl)-6-deoxy-L-gulose $^1$H NMR (400 MHz, Methanol-d$_4$) δ 7.39-7.25 (m, 10H, C$\underline{H}_{benzyl}$), 4.72-4.41 (m, 4H, C$\underline{H}_2$ $_{benzyl}$), 4.00 (qd, J=6.6, 1.2 Hz, 1H, H-5), 3.81 (dd, J=8.9, 3.7 Hz, 1H, H-1$_{equatorial}$), 3.66-3.52 (m, 2H, H-2, H-1$_{axial}$), 3.34 (d, J=1.1 Hz, 1H, H-4), 2.95 (d, J=13.6 Hz, 1H, C$\underline{H}_2$NH$_2$), 2.70 (d, J=13.6 Hz, 1H, C$\underline{H}_2$NH$_2$), 1.23 (d, J=6.6 Hz, 3H, H-6); $^{13}$C NMR (101 MHz, Methanol-d4) δ 139.4 ($\underline{C}_{benzyl}$), 129.4 (C$\underline{H}_{benzyl}$), 129.4 (C$\underline{H}_{benzyl}$), 129.0 (C$\underline{H}_{benzyl}$), 128.9 (C$\underline{H}_{benzyl}$), 128.8 (C$\underline{H}_{benzyl}$), 81.4 (C-4), 76.8 ($\underline{C}$H$_2$ $_{benzyl}$), 75.6 (C-2), 74.6 (C-3), 73.5 ($\underline{C}$H$_2$ $_{benzyl}$), 72.9 (C-5), 64.9 (C-1), 45.7 ($\underline{C}$H$_2$NH$_2$), 17.5 (C-6); HR-MS calcd. for C$_{21}$H$_{28}$NO$_4^+$: 358.2013; found: 258.2000.

1.3.5 1-deoxy-2,3-di-O-benzyl-4(S)—C-(methyl) L-fucose and 1-deoxy-2,3-di-O-benzyl-4(R)—C-(methyl)-6-deoxy-L-glucose

Methyllithium solution (281 μL 0.45 mmol, 1.6 M in Et$_2$O) was used as nucleophile. Purification of the reaction mixture yielded 1-deoxy-2,3-di-O-benzyl-4(S)—C-(methyl) L-fucose (21 mg, 0.061 mmol, 20%) as colorless oil and 1-deoxy-2,3-di-O-benzyl-4(R)—C-(methyl)-6-deoxy-L-glucose (50 mg, 0.145 mmol, 49%) as colorless oil.

1-deoxy-2,3-di-O-benzyl-4(S)—C-(methyl) L-fucose $^1$H NMR (500 MHz, Chloroform-d) δ 7.39-7.27 (m, 10H, C$\underline{H}_{benzyl}$), 5.03 (d, J=11.0 Hz, 1H, C$\underline{H}_2$ $_{benzyl}$), 4.72 (d, J=11.1 Hz, 1H, C$\underline{H}_2$ $_{benzyl}$), 4.70-4.54 (m, 2H, C$\underline{H}_2$ $_{benzyl}$), 4.05 (dd, J=11.1, 5.4 Hz, 1H, H-1$_{equatorial}$) 3.93-3.84 (m, 1H, H-2), 3.27 (q, J=6.4 Hz, 1H, H-5), 3.23 (d, J=9.0 Hz, 1H, H-3), 3.19 (t, J=10.9 Hz, 1H, H-1$_{axial}$), 1.23 (d, J=6.4 Hz, 3H, H-6), 1.14 (s, 3H, CH$_3$). $^{13}$C NMR (126 MHz, Chloroform-d) δ 138.4 ($\underline{C}_{benzyl}$), 138.4 ($\underline{C}_{benzyl}$), 128.6 (C$\underline{H}_{benzyl}$), 128.5 (C$\underline{H}_{benzyl}$), 128.3 (C$\underline{H}_{benzyl}$), 128.0 (C$\underline{H}_{benzyl}$), 128.0 (C$\underline{H}_{benzyl}$), 128.0 (C$\underline{H}_{benzyl}$), 85.1 (C-3), 78.9 (C-5), 77.3 (C-2), 76.1 ($\underline{C}$H$_2$ $_{benzyl}$), 73.9 (C-4), 73.2 ($\underline{C}$H$_2$ $_{benzyl}$), 68.3 (C-1), 22.2 (CH$_3$), 14.1 (C-6). HR-MS calcd. C$_{21}$H$_{26}$NaO$_4^+$: 365.1723; found: 365.1713.

1-deoxy-2,3-di-O-benzyl-4(R)—C-(methyl)-6-deoxy-L-glucose $^1$H NMR (500 MHz, Chloroform-d) δ 7.41-7.28 (m, 10H, C$\underline{H}_{benzyl}$), 5.03 (d, J=11.8 Hz, 1H), 4.77 (d, J=11.8 Hz, 1H, $CH_2$ $_{benzyl}$), 4.73-4.56 (m, 2H, $CH_2$ $_{benzyl}$), 4.01 (dd, J=11.2, 5.4 Hz, 1H, H-1$_{equatorial}$), 3.57 (ddd, J=10.3, 9.2, 5.4 Hz, 1H, H-2), 3.40 (d, J=9.1 Hz, 1H, H-3), 3.34-3.21 (m, 2H, H-1$_{axial}$, H-5), 1.17 (s, 3H, $CH_3$), 1.17 (d, J=6.4 Hz, 3H, H-6). $^{13}$C NMR (126 MHz, Chloroform-d) δ 139.1 ($C_{benzyl}$), 138.4 ($C_{benzyl}$), 128.7 ($CH_{benzyl}$), 128.6 ($CH_{benzyl}$), 127.9 ($CH_{benzyl}$), 127.9 ($CH_{benzyl}$), 127.8 ($CH_{benzyl}$), 127.8 ($CH_{benzyl}$), 88.1 (C-3), 78.8 (C-5), 77.9 (C-2), 75.5 ($CH_2$ $_{benzyl}$), 74.2 (C-4), 73.3 ($CH_2$ $_{benzyl}$), 68.6 (C-1), 15.9 ($CH_3$), 13.9 (C-6). HR-MS calcd. $C_{21}H_{26}NaO_4^+$: 365.1723; found: 365.1715.

1.3.6 1-deoxy-2,3-di-O-benzyl-4(S)—C-(vinyl) L-Fucose

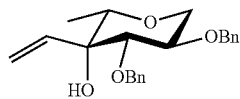

Vinylmagnesium bromide solution (642 µL, 0.45 mmol, 0.7 M in THF) was used as nucleophile. Purification of the reaction mixture yielded 1-deoxy-2,3-di-O-benzyl-4(S)—C-(vinyl) L-fucose (84 mg, 0.24 mmol, 79%) as colorless solid. $^1$H NMR (500 MHz, Chloroform-d) δ 7.46-7.28 (m, 10H, $CH_{benzyl}$), 5.72 (dd, J=17.1, 10.7 Hz, 1H, $CH_{vinyl}$), 5.50 (dd, J=17.1, 1.4 Hz, 1H, $CH_2$ $_{vinyl}$), 5.33 (dd, J=10.7, 1.4 Hz, 1H, $CH_2$ $_{vinyl}$), 4.84 (d, J=10.7 Hz, 1H, $CH_2$ $_{benzyl}$), 4.75-4.62 (m, 3H, $CH_2$ $_{benzyl}$), 4.08 (dd, J=11.2, 5.5 Hz, 1H, H-1$_{equatorial}$) 3.88 (ddd, J=10.7, 8.9, 5.5 Hz, 1H, H-2), 3.46 (d, J=8.9 Hz, 1H, H-3), 3.40 (q, J=6.4 Hz, 1H, H-5), 3.24 (t, J=11.0 Hz, 1H, H-1$_{axial}$), 1.17 (d, J=6.4 Hz, 3H, H-6). $^{13}$C NMR (126 MHz, Chloroform-d) δ 139.8 ($CH_{vinyl}$), 138.4 ($C_{benzyl}$), 138.2 ($C_{benzyl}$), 128.5 ($CH_{benzyl}$), 128.4 ($CH_{benzyl}$), 128.3 ($CH_{benzyl}$), 127.9 ($CH_{benzyl}$), 127.9 ($CH_{benzyl}$), 127.9 ($CH_{benzyl}$), 116.4 ($CH_2$ $_{vinyl}$), 84.4 (C-3), 77.3 (C-4), 77.3 (C-5), 76.3 (C-2), 75.8 ($CH_2$ $_{benzyl}$), 73.4 ($CH_2$ $_{benzyl}$), 68.2 (C-1), 14.0 (C-6). HR-MS calcd. $C_{22}H_{26}NaO_4^+$: 377.1723; found: 377.1715.

1.3.7 1-deoxy-2,3-di-O-benzyl-4(S)—C-(allyl) L-fucose and 1-deoxy-2,3-di-O-benzyl-4(R)—C-(allyl)-6-deoxy-L-glucose

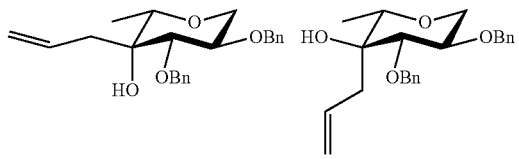

Fresh prepared allylmagnesium bromide solution (214 µM, 2.1 M in Et$_2$O) was used as nucleophile. Purification of the reaction mixture yielded 1-deoxy-2,3-di-O-benzyl-4(S)—C-(allyl) L-fucose (89 mg, 0.24 mmol, 81%) as colorless solid and 1-deoxy-2,3-di-O-benzyl-4(R)—C-(allyl)-6-deoxy-L-glucose (17 mg, 0.05 mmol, 15%) as colorless oil.

1-deoxy-2,3-di-O-benzyl-4(S)—C-(allyl) L-fucose $^1$H NMR (500 MHz, Chloroform-d) δ 7.39-7.27 (m, 10H, $CH_{benzyl}$), 5.59 (ddt, J=16.3, 10.8, 7.6 Hz, 1H, $CH_{allyl}$), 5.12-5.01 (m, 3H, $CH_2$ $_{allyl}$, $CH_2$ $_{benzyl}$), 4.74 (d, J=11.1 Hz, 1H, $CH_2$ $_{benzyl}$), 4.69-4.59 (m, 2H, $CH_2$ $_{benzyl}$), 4.03 (dd, J=11.1, 5.4 Hz, 1H, H-1$_{equatorial}$), 3.94 (ddd, J=10.7, 8.8, 5.4 Hz, 1H, H-2), 3.48 (d, J=8.8 Hz, 1H, H-3), 3.37 (q, J=6.3 Hz, 1H, H-5), 3.14 (t, J=10.9 Hz, 1H, H-1$_{axial}$), 2.65 (ddt, J=14.1, 7.6, 1.4 Hz, 1H, $CH_2$ $_{allyl}$), 2.17 (ddt, J=14.0, 7.5, 1.2 Hz, 1H, $CH_2$ $_{allyl}$), 1.25 (d, J=6.3 Hz, 3H, H-6). $^{13}$C NMR (126 MHz, Chloroform-d) δ 138.4 ($C_{benzyl}$), 138.3 ($C_{benzyl}$), 132.5 ($CH_{allyl}$), 128.6 ($CH_{benzyl}$), 128.6 ($CH_{benzyl}$), 128.1 ($CH_{benzyl}$), 128.0 ($CH_{benzyl}$), 128.0 ($CH_{benzyl}$), 119.0 ($CH_2$ $_{allyl}$), 81.1 (C-3), 77.8 (C-2), 76.5 (C-5), 75.8 (C-4), 75.3 ($CH_2$ $_{benzyl}$), 73.1 ($CH_2$ $_{benzyl}$), 68.0 (C-1), 39.9 ($CH_2$ $_{allyl}$), 13.8 (C-6). HR-MS calcd. $C_{22}H_{28}NaO_4^+$: 391,1880; found: 391.1869.

1-deoxy-2,3-di-O-benzyl-4(R)—C-(allyl)-6-deoxy-L-glucose $^1$H NMR (500 MHz, Chloroform-d) δ 7.39-7.27 (m, 10H, $CH_{benzyl}$), 6.03 (dddd, J=17.3, 10.3, 7.7, 7.1 Hz, 1H, $CH_{benzyl}$), 5.16-5.09 (m, 2H, $CH_2$ $_{allyl}$), 4.83 (d, J=11.7 Hz, 1H, $CH_2$ $_{benzyl}$), 4.69 (d, J=11.7 Hz, 1H, $CH_2$ $_{benzyl}$), 4.67-4.58 (m, 2H, $CH_2$ $_{benzyl}$), 4.00 (dd, J=11.7, 4.4 Hz, 1H, H-1$_{equatorial}$), 3.61 (td, J=7.6, 4.4 Hz, 1H, H-2), 3.53-3.46 (m, 2H, H-3, H-5), 3.41 (dd, J=11.8, 7.7 Hz, 1H, H-1$_{axial}$), 2.51 (ddt, J=14.2, 7.1, 1.3 Hz, 1H, $CH_2$ $_{allyl}$), 2.34 (ddt, J=14.1, 7.7, 1.1 Hz, 1H, $CH_2$ $_{allyl}$), 1.25 (d, J=6.7 Hz, 3H, H-6). $^{13}$C NMR (126 MHz, Chloroform-d) δ 138.8 ($C_{benzyl}$), 138.1 ($C_{benzyl}$), 134.5 ($CH_{allyl}$), 128.6 ($CH_{benzyl}$), 128.6 ($CH_{benzyl}$), 128.0 ($CH_{benzyl}$), 127.9 ($CH_{benzyl}$), 127.9 ($CH_{benzyl}$), 127.8 ($CH_{benzyl}$), 127.6 ($CH_{benzyl}$), 118.6 ($CH_2$ $_{allyl}$), 85.5 (C-3), 79.0 (C-5), 76.0 (C-4), 75.1 (C-2), 74.1 ($CH_2$ $_{benzyl}$), 72.8 ($CH_2$ $_{benzyl}$), 65.6 (C-1), 35.8 ($CH_2$ $_{allyl}$), 14.5 (C-6). HR-MS calcd. $C_{23}H_{28}NaO_4^+$: 391, 1879; found: 391.1878.

1.3.8 1-deoxy-2,3-di-O-benzyl-4(S)—C-(butyl) L-Fucose

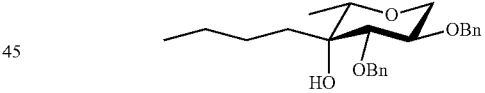

Butyllithium solution (180 µL 0.45 mmol, 2.5 M in hexane) was used as nucleophile. Purification of the reaction mixture yielded 1-deoxy-2,3-di-O-benzyl-4(S)—C-(butyl) L-fucose (47 mg, 0.12 mmol, 41%) as colorless oil. $^1$H NMR (500 MHz, Chloroform-d) δ 7.39-7.27 (m, 10H, $CH_{benzyl}$), 5.01 (d, J=11.1 Hz, 1H, $CH_2$ $_{benzyl}$), 4.74-4.67 (m, 2H, $CH_2$ $_{benzyl}$), 4.63 (d, J=11.5 Hz, 1H, $CH_2$ $_{benzyl}$), 4.04 (dd, J=11.1, 5.5 Hz, 1H, H-1$_{equatorial}$), 3.99-3.91 (m, 1H, H-2), 3.48 (d, J=8.8 Hz, 1H, H-3), 3.38 (q, J=6.4 Hz, 1H, H-5), 3.14 (t, J=10.9 Hz, 1H, H-1$_{axial}$), 1.82 (td, J=13.1, 4.6 Hz, 1H, $CH_2$ $_{butyl}$), 1.51-0.89 (m, 5H, $CH_2$ $_{butyl}$), 1.20 (d, J=6.5 Hz, 3H, H-6), 0.83 (t, J=7.3 Hz, 3H, $CH_3$ $_{butyl}$). $^{13}$C NMR (126 MHz, Chloroform-d) δ 138.4 ($C_{benzyl}$), 138.4 ($C_{benzyl}$), 128.6 ($CH_{benzyl}$), 128.5 ($CH_{benzyl}$), 128.4 ($CH_{benzyl}$), 128.0 (2×$CH_{benzyl}$), 127.9 ($CH_{benzyl}$), 80.9 (C-3), 77.8 (C-2), 76.5 (C-5), 75.8 (C-4), 75.4 ($CH_2$ $_{benzyl}$), 73.1 ($CH_2$ $_{benzyl}$), 68.1 (C-1), 34.9 ($CH_2$ $_{butyl}$), 26.1 ($CH_2$ $_{butyl}$), 23.4 ($CH_2$ $_{butyl}$), 14.0 ($CH_3$ $_{butyl}$), 13.7 (C-6). HR-MS calcd. $C_{24}H_{32}NaO_4^+$: 407.2193; found: 407.2182.

1.3.9 1-deoxy-2,3-di-O-benzyl-4(S)—C-(hexyl) L-Fucose

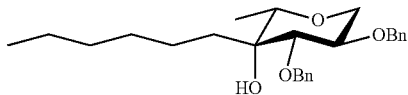

Hexyllithium solution (196 μL, 0.45 mmol, 2.3 M in hexane) was used as nucleophile. Purification of the reaction mixture yielded impure 1-deoxy-2,3-di-O-benzyl-4(S)—C-(hexyl) L-fucose (68 mg, 0.165 mmol, 55%) as colorless solid. $^1$H NMR (500 MHz, Chloroform-d) δ 7.39-7.29 (m, 10H, C$\underline{H}_{benzyl}$), 5.01 (d, J=11.1 Hz, 1H, C$\underline{H}_{2\ benzyl}$), 4.75-4.61 (m, 3H, C$\underline{H}_{2\ benzyl}$), 4.04 (dd, J=11.1, 5.5 Hz, 1H, H-1$_{equatorial}$), 3.95 (ddd, J=10.6, 8.9, 5.5 Hz, 1H, H-2), 3.48 (d, J=8.7 Hz, 1H, H-3), 3.38 (q, J=6.3 Hz, 1H, H-5), 3.16 (t, J=10.8 Hz, 1H, H-1$_{axial}$), 1.81 (td, J=13.0, 4.4 Hz, 1H, C$\underline{H}_{2\ hexyl}$), 1.48-0.96 (m, 9H, C$\underline{H}_{2\ hexyl}$), 1.20 (d, J=6.4 Hz, 3H, H-6), 0.88 (t, J=7.3 Hz, 3H, C$\underline{H}_{3\ hexyl}$). $^{13}$C NMR (126 MHz, Chloroform-d) δ 138.4 ($\underline{C}_{benzyl}$), 138.4 ($\underline{C}_{benzyl}$), 128.6 (C$\underline{H}_{benzyl}$), 128.5 (C$\underline{H}_{benzyl}$), 128.4 (C$\underline{H}_{benzyl}$), 128.0 (C$\underline{H}_{benzyl}$), 127.9 (C$\underline{H}_{benzyl}$), 81.0 (C-3), 76.5 (C-5), 75.8 (C-4), 75.4 (C$\underline{H}_{2\ benzyl}$), 73.1 (C$\underline{H}_{2\ benzyl}$), 68.1 (C-1), 35.2 (C$\underline{H}_{2\ hexyl}$), 31.7 (C$\underline{H}_{2\ hexyl}$), 30.0 (C$\underline{H}_{2\ hexyl}$), 23.9 (C$\underline{H}_{2\ hexyl}$), 22.7 (C$\underline{H}_{2\ hexyl}$), 14.2 (C$\underline{H}_{3\ hexyl}$), 13.8 (C-6). HR-MS calcd. $C_{26}H_{36}NaO_4^+$: 435.2506; found: 435.2491.

1.3.10 1-deoxy-2,3-di-O-benzyl-4(S)—C-(phenyl) L-Fucose

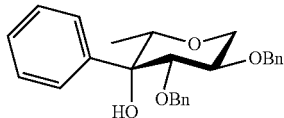

Phenylmagnesium chloride solution (450 μL 0.45 mmol, 1 M in THF) was used as nucleophile. Purification of the reaction mixture yielded 1-deoxy-2,3-di-O-benzyl-4(S)—C-(phenyl) L-fucose (61 mg, 0.15 mmol, 50%) as colorless solid. $^1$H NMR (500 MHz, Chloroform-d) δ 7.57-7.14 (m, 13H, C$\underline{H}_{benzyl}$, C$\underline{H}_{phenyl}$), 6.92-6.84 (m, 2H, C$\underline{H}_{phenyl}$), 4.76 (d, J=11.5 Hz, 1H, C$\underline{H}_{2\ benzyl}$), 4.69 (d, J=11.5 Hz, 1H, C$\underline{H}_{2\ benzyl}$), 4.51 (d, J=11.6 Hz, 1H, C$\underline{H}_{2\ benzyl}$), 4.17 (dd, J=11.3, 5.3 Hz, 1H, H-1$_{equatorial}$), 4.01 (d, J=11.6 Hz, 1H, C$\underline{H}_{2\ benzyl}$), 3.98 (ddd, J=10.5, 8.8, 5.3 Hz, 1H, H-2), 3.93 (d, J=8.8 Hz, 1H, H-3), 3.74 (q, J=6.4 Hz, 1H, H-5), 3.42 (t, J=10.8 Hz, 1H, H-1$_{axial}$), 0.96 (d, J=6.4 Hz, 3H, H-6). $^{13}$C NMR (126 MHz, Chloroform-d) δ 142.5 ($\underline{C}_{phenyl}$), 138.4 ($\underline{C}_{benzyl}$), 137.8 ($\underline{C}_{benzyl}$), 128.6 (C$\underline{H}_{benzyl}$), 128.5 (C$\underline{H}_{phenyl}$), 128.3 (C$\underline{H}_{benzyl}$), 128.2 (C$\underline{H}_{benzyl}$), 127.9 (2×C$\underline{H}_{benzyl}$), 127.8 (C$\underline{H}_{benzyl}$), 127.3 (C$\underline{H}_{phenyl}$), 125.5 (C$\underline{H}_{phenyl}$), 86.1 (C-3), 79.4 (C-5), 78.1 (C-4), 76.7 (C-2), 75.5 (C$\underline{H}_{2\ benzyl}$), 73.5 (C$\underline{H}_{2\ benzyl}$), 68.4 (C-1), 13.8 (C-6). HR-MS calcd. $C_{26}H_{28}NaO_4^+$: 427.1880; found: 427.1863.

1.3.11 1-deoxy-2,3-di-O-benzyl-4(S)—C-(benzyl) L-Fucose

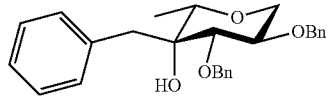

Benzylmagnesium chloride solution (340 μL, 0.45 mmol, 20% in THF) was used as nucleophile. Purification of the reaction mixture yielded 1-deoxy-2,3-di-O-benzyl-4(S)—C-(benzyl) L-fucose (50 mg, 0.12 mmol, 40%) as colorless solid. $^1$H NMR (500 MHz, Chloroform-d) δ 7.30-6.89 (m, 15H, C$\underline{H}_{benzyl}$), 5.04 (dd, J=11.7, 1.4 Hz, 1H, C$\underline{H}_{2\ O\text{-}benzyl}$), 4.66 (dd, J=11.7, 1.3 Hz, 1H, C$\underline{H}_{2\ O\text{-}benzyl}$), 4.42 (d, J=3.0 Hz, 2H, C$\underline{H}_{2\ O\text{-}benzyl}$), 3.92-3.76 (m, 2H, H-1$_{equatorial}$, H-2), 3.34 (d, J=8.2 Hz, 1H, H-3), 3.22 (q, J=6.3 Hz, 1H, H-5), 3.04 (d, J=13.7 Hz, 1H, C$\underline{H}_{2\ C\text{-}benzyl}$), 2.88-2.76 (m, 1H, H-1$_{axial}$), 2.67 (d, J=13.8 Hz, 1H, C$\underline{H}_{2\ C\text{-}benzyl}$), 1.27 (dd, J=6.3, 1.3 Hz, 3H). $^{13}$C NMR (126 MHz, Chloroform-d) δ 138.9 ($\underline{C}_{benzyl}$), 138.0 ($\underline{C}_{benzyl}$), 136.5 ($\underline{C}_{benzyl}$), 130.3 (C$\underline{H}_{benzyl}$), 128.6 (C$\underline{H}_{benzyl}$), 128.6 (C$\underline{H}_{benzyl}$), 128.6 (C$\underline{H}_{benzyl}$), 128.1 (C$\underline{H}_{benzyl}$), 128.0 (C$\underline{H}_{benzyl}$), 127.8 (C$\underline{H}_{benzyl}$), 127.5 (C$\underline{H}_{benzyl}$), 126.8 (C$\underline{H}_{benzyl}$), 80.1 (C-3), 78.4 (C-2), 76.5 (C-4), 76.1 (C-5), 74.2 (C$\underline{H}_{2\ O\text{-}benzyl}$), 72.7 (C$\underline{H}_{2\ O\text{-}benzyl}$), 67.2 (C-1), 41.8 (C$\underline{H}_{2\ C\text{-}benzyl}$), 14.7 (C-6). HR-MS calcd. $C_{27}H_{30}NaO_4^+$: 441.2036; found: 441.2022.

1.3.12 1-deoxy-2,3-di-O-benzyl-4(S)—C-(cyclohexyl) L-Fucose

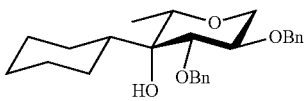

Cyclohexylmagnesium chloride solution (346 μL 0.45 mmol, 1.3 M in Et$_2$O) was used as nucleophile. Purification of the reaction mixture yielded 1-deoxy-2,3-di-O-benzyl-4(S)—C-(cyclohexyl) L-fucose (95 mg, 0.23 mmol, 77%) as colorless solid. $^1$H NMR (500 MHz, Chloroform-d) δ 7.40-7.26 (m, 10H, C$\underline{H}_{benzyl}$), 5.07 (d, J=11.0 Hz, 1H, C$\underline{H}_{2\ benzyl}$), 4.75 (d, J=11.0 Hz, 1H, C$\underline{H}_{2\ benzyl}$), 4.66 (d, J=11.7 Hz, 1H, C$\underline{H}_{2\ benzy}$), 4.61 (d, J=11.6 Hz, 1H, C$\underline{H}_{2\ benzy}$), 4.03 (dd, J=11.0, 5.5 Hz, 1H, H-1$_{equatorial}$), 3.95 (ddd, J=10.7, 8.6, 5.5 Hz, 1H, H-2), 3.56 (d, J=8.6 Hz, 1H, H-3), 3.45 (q, J=6.3 Hz, 1H, H-5), 3.16 (t, J=10.8 Hz, 1H, H-1$_{axial}$), 1.94-1.55 (m, 5H, C$\underline{H}_{2\ cyclohexyl}$, C$\underline{H}_{cyclohexyl}$), 1.26 (d, J=6.3 Hz, 3H, H-6), 1.44-0.95 (m, 4H, C$\underline{H}_{2\ cyclohexyl}$). $^{13}$C NMR (126 MHz, Chloroform-d) δ 138.4 ($\underline{C}_{benzyl}$), 138.3 ($\underline{C}_{benzyl}$), 128.5 (C$\underline{H}_{benzyl}$), 128.4 (C$\underline{H}_{benzyl}$), 128.2 (C$\underline{H}_{benzyl}$), 127.9 (C$\underline{H}_{benzyl}$), 127.9 (C$\underline{H}_{benzyl}$), 127.8 (C$\underline{H}_{benzyl}$), 81.4 (C-3), 78.3 (C-2), 77.2 (C-4), 76.7 (C-5), 75.1 (C$\underline{H}_{2\ benzyl}$), 73.1 (C$\underline{H}_{2\ benzyl}$), 67.9 (C-1), 43.5 (C$\underline{H}_{cyclohexyl}$), 28.2 (C$\underline{H}_{2\ cyclohexyl}$), 28.0 (C$\underline{H}_{2\ cyclohexyl}$), 27.5 (C$\underline{H}_{2\ cyclohexyl}$), 27.4 (C$\underline{H}_{2\ cyclohexyl}$), 26.8 (C$\underline{H}_{2\ cyclohexyl}$), 15.5 (C-6). HR-MS calcd. $C_{26}H_{34}NaO_4^+$: 433.2349; found: 433.2332.

1.3.13 1-deoxy-2,3-di-O-benzyl-4(S)—C-(isopentyl) L-Fucose

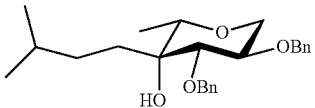

Fresh prepared isopentylmagnesium bromide solution (214 μL, 0.45 mmol, 2.1 M in Et$_2$O) was used as nucleophile. Purification of the reaction mixture yielded 1-deoxy-2,3-di-O-benzyl-4(S)—C-(isopentyl) L-fucose (107 mg, 0.27 mmol, 89%) as colorless solid. $^1$H NMR (500 MHz, Chloroform-d) δ 7.45-7.28 (m, 10H, C$\underline{H}_{benzyl}$), 5.03 (d, J=11.0 Hz, 1H, C$\underline{H}_{2\ benzyl}$), 4.73 (d, J=11.0 Hz, 1H, C$\underline{H}_{2\ benzyl}$), 4.69 (d, J=11.4 Hz, 1H, C$\underline{H}_{2\ benzyl}$), 4.63 (d, J=11.4 Hz, 1H, C$\underline{H}_{2\ benzyl}$), 4.05 (dd, J=11.1, 5.5 Hz, 1H, H-1$_{equatorial}$), 4.01-3.92 (m, 1H, H-2), 3.50 (d, J=8.8 Hz, 1H, H-3), 3.40 (q, J=6.3 Hz, 1H, H-5), 3.17 (t, J=10.9 Hz, 1H, H-1$_{axial}$), 1.93-1.77 (m, 1H, C$\underline{H}_{2\ isopentyl}$), 1.45-1.35 (m, 2H, C$\underline{H}_{isopentyl}$, C$\underline{H}_{2\ isopentyl}$), 1.22 (d, J=6.4 Hz, 3H, H-6), 1.06-0.97 (m, 2H, C$\underline{H}_{2\ isopentyl}$), 0.88 (d, J=6.6 Hz, 3H, C$\underline{H}_{3\ isopentyl}$), 0.86 (d, J=6.7 Hz, 3H, C$\underline{H}_{3\ isopentyl}$). $^{13}$C NMR (126 MHz, Chloroform-d) δ 138.4 ($\underline{C}_{benzyl}$), 138.4 ($\underline{C}_{benzyl}$), 128.6 ($\underline{C}H_{benzyl}$), 128.5 ($\underline{C}H_{benzyl}$), 128.3 ($\underline{C}H_{benzyl}$), 127.9 ($\underline{C}H_{benzyl}$), 127.9 ($\underline{C}H_{benzyl}$), 127.9 ($\underline{C}H_{benzyl}$), 81.0 (C-3), 77.8 (C-2), 76.4 (C-5), 75.8 (C-4), 75.4 ($\underline{C}H_{2\ benzyl}$), 73.1 ($\underline{C}H_{2\ benzyl}$), 68.1 (C-1), 33.0 ($\underline{C}H_{2\ isopentyl}$), 32.9 ($\underline{C}H_{2\ isopentyl}$), 28.7 ($\underline{C}H_{isopentyl}$), 22.8 ($\underline{C}H_{3\ isopentyl}$), 22.3 ($\underline{C}H_{3\ isopentyl}$), 13.7 (C-6). HR-MS calcd. C$_{25}$H$_{34}$NaO$_4^+$: 421.2349; found: 421.2332.

1.3.14 1-deoxy-2,3-di-O-benzyl-4(S)—C-(cyanomethyl) L-Fucose

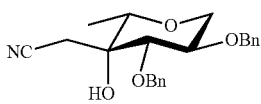

Fresh prepared cyanomethyllithium solution (450 μL, 0.45 mmol, 1 M in THF) was used as nucleophile. Purification of the reaction mixture yielded 1-deoxy-2,3-di-O-benzyl-4(S)—C-(cyanomethyl) L-fucose (85 mg, 0.23 mmol, 77%) as colorless oil. $^1$H NMR (500 MHz, Chloroform-d) δ 7.42-7.28 (m, 10H, C$\underline{H}_{benzyl}$), 5.08 (d, J=11.2 Hz, 1H, C$\underline{H}_{2\ benzyl}$), 4.77 (d, J=11.2 Hz, 1H, C$\underline{H}_{2\ benzyl}$), 4.67 (d, J=11.6 Hz, 1H, C$\underline{H}_{2\ benzyl}$), 4.64 (d, J=11.7 Hz, 1H, C$\underline{H}_{2\ benzyl}$), 4.05 (dd, J=11.4, 5.4 Hz, 1H, H-1$_{equatorial}$) 3.88 (ddd, J=10.6, 8.8, 5.4 Hz, 1H, H-2), 3.65 (d, J=9.0 Hz, 1H, H-3), 3.63 (q, J=6.2 Hz, 1H, H-5), 3.25 (dd, J=11.4, 10.5 Hz, 1H, H-1$_{axial}$), 2.77 (d, J=16.9 Hz, 1H, C$\underline{H}_2$CN), 2.33 (d, J=6.4 Hz, 3H, C$\underline{H}_2$CN), 1.27 (d, J=6.4 Hz, 3H, H-6). $^{13}$C NMR (126 MHz, Chloroform-d) δ 138.0 ($\underline{C}_{benzyl}$), 137.5 ($\underline{C}_{benzyl}$), 128.8 ($\underline{C}H_{benzyl}$), 128.7 ($\underline{C}H_{benzyl}$), 128.6 ($\underline{C}H_{benzyl}$), 128.4 ($\underline{C}H_{benzyl}$), 128.1 ($\underline{C}H_{benzyl}$), 128.0 ($\underline{C}H_{benzyl}$), 116.2 ($\underline{C}H_2$CN), 80.9 (C-3), 77.1 (C-2), 76.1 (C-5), 75.9 ($\underline{C}H_{2\ benzyl}$), 74.2 (C-4), 73.0 ($\underline{C}H_{2\ benzyl}$), 67.8 (C-1), 23.5 ($\underline{C}H_2$CN), 13.9 (C-6). HR-MS calcd. C$_{22}$H$_{25}$NaO$_4^+$: 390.1676; found: 390.1669.

1.4 General Procedure for Debenzylation

The corresponding benzylated L-fucose derivative was stirred in MeOH (0.02 M) under hydrogen atmosphere (1 bar) with 10% PdC (10 mol %) at r.t. for 10-16 h. The mixture was filtered through celite and the solvent was removed in vacuo. The residue was purified by MPLC (CH$_2$Cl$_2$ to CH$_2$Cl$_2$/MeOH=8:1)

1.4.1 1-deoxy-3(S)—C-(methyl)-L-fucose

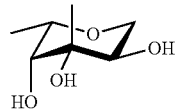

Purification of the reaction mixture yielded 1-deoxy-3(S)—C-(methyl)-L-fucose (13.4 mg, 0.082 mmol, 95%) as colorless oil. $^1$H NMR (500 MHz, DMSO-d$_6$) δ 4.58 (bs, 1H, OH), 4.37 (bs, 1H, OH), 4.14 (bs, 1H, OH), 3.66-3.45 (m, 3H), 3.08 (bs, 1H), 2.96 (t, J=10.9 Hz, 1H, H-1$_{axial}$), 1.22-0.86 (m, 6H, H-6, C$\underline{H}_3$). $^{13}$C NMR (126 MHz, DMSO-d$_6$) δ 76.2, 72.8 (C-3), 72.1, 68.9, 68.2 (C-1), 17.8 (CH$_3$), 17.3 (C-6). ESI-MS calcd. C$_7$H$_{14}$NaO$_4^+$: 185.1; found: 184.9.

1.4.2 1-deoxy-3(S)—C-(ethyl)-L-fucose

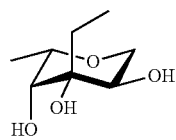

Purification of the reaction mixture yielded 1-deoxy-3(S)—C-(ethyl)-L-fucose (13 mg, 0.074 mmol, 53%) as colorless oil. $^1$H NMR (500 MHz, Methanol-d$_4$) δ 3.88 (dd, J=10.7, 5.5 Hz, 1H, H-2), 3.71 (dd, J=11.2, 5.5 Hz, 1H, H-1$_{equatorial}$), 3.68 (qd, J=6.4, 1.2 Hz, 1H, H-5), 3.50 (d, J=1.2 Hz, 1H, H-4), 3.31-3.22 (m, 1H, H-1$_{axial}$), 1.84 (dq, J=15.3, 7.7 Hz, 1H, C$\underline{H}_{2\ ethyl}$), 1.63 (dq, J=14.8, 7.4 Hz, 1H, C$\underline{H}_{2\ ethyl}$), 1.20 (d, J=6.4 Hz, 3H, H-6), 0.92 (t, J=7.5 Hz, 3H, C$\underline{H}_{3\ ethyl}$). $^{13}$C NMR (126 MHz, Methanol-d$_4$) δ 75.6 (C-3), 73.7 (C-5), 73.5 (C-4), 71.3 (C-2), 69.1 (C-1), 22.4 ($\underline{C}H_{2\ ethyl}$), 17.4 (C-6), 7.1 ($\underline{C}H_{3\ ethyl}$). ESI-MS calcd. C$_8$H$_{17}$O$_4^+$: 199.1; found: 198.2.

1.4.3 1-deoxy-3(S)—C-(trifluoromethyl)-L-fucose

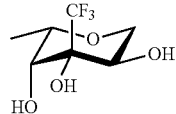

Purification of the reaction mixture yielded 1-deoxy-3(S)—C-(ethyl)-L-fucose (46.7 mg, 0.216 mmol, 86%) as colorless solid. $^1$H NMR (600 MHz, D$_2$O) δ 4.01-3.91 (m, 3H, H-2, H-4, H-5), 3.88 (dd, J=12.0, 5.0 Hz, 1H, H-1$_{equatorial}$) 3.58-3.51 (m, 1H, H-1$_{axial}$), 1.21 (d, J=6.4 Hz, 3H, H-6). $^{13}$C NMR (151 MHz, D$_2$O) δ 125.13 (q, J$_{CF}$=287.1 Hz, $\underline{C}$F$_3$), 75.28 (q, J$_{CF}$=25.0 Hz, C-3), 72.2 (C-5), 68.5 (C-2), 68.3 (C-4), 65.0 (C-1), 14.6 (C-6).

1.4.4 1-deoxy-3(S)—C-(aminomethyl)-L-fucose

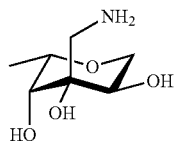

Purification of the reaction mixture yielded 1-deoxy-3(S)—C-(ethyl)-L-fucose (20 mg, 0.112 mmol, 64%) as colorless oil. $^1$H NMR (400 MHz, Methanol-$d_4$) δ 3.98 (dd, J=10.6, 5.6 Hz, 1H, H-2), 3.80 (dd, J=11.4, 5.5 Hz, 1H, H-1$_{equatorial}$) 3.70-3.64 (m, 1H, H-5), 3.42 (d, J=1.4 Hz, 1H, H-4), 3.35-3.26 (m, 2H, H-1$_{axial}$, C$\underline{H}_2$NH$_2$), 2.79 (d, J=13.5 Hz, 1H, C$\underline{H}_2$NH$_2$), 1.24 (d, J=6.4 Hz, 3H, H-6). $^{13}$C NMR (101 MHz, Methanol-$d_4$) δ 74.4 (C-4), 74.1 (C-5), 74.0 (C-3), 71.5 (C-2), 69.3 (C-1), 42.7 ($\underline{C}H_2$NH$_2$), 17.1 (C-6). ESI-MS calcd. $C_7H_{16}NO_4^+$: 178.1; found: 177.9.

1.4.5 1-deoxy-3(S)—C-(isobutyrylamidomethyl)-L-fucose

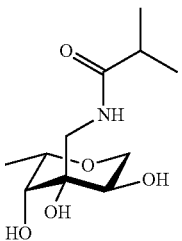

1-deoxy-2,4-di-O-benzyl-3-C—(S)-aminomethyl-L-fucose (0.03 mg, 0.08 mmol) and triethylamine (18 μL, 0.13 mmol) were dissolved in dry DMF (0.7 mL) and cooled to 0° C. Isobutyryl chloride (11 μL, 0.10 mmol) was added dropwise under nitrogen. The reaction was allowed to warm to r.t. and was stirred for further 4 h. Saturated aqueous NH$_4$Cl (3 mL) was added, and extracted with EtOAc (3×10 mL). The combined organic layers were dried over Na$_2$SO$_4$, filtered and concentrated in vacuo. The residue was purified by chromatography on silica (PE to PE/EtOAc=3:1). 1-deoxy-2,4-di-O-benzyl-3-C—(S)-isobutyrylamidomethyl-L-fucose (0.03 mg, 0.07 mmol) was obtained as light yellow oil and was subsequently debenzylated corresponding to general procedure for debenzylation. 1-deoxy-3(S)—C-(isobutyrylamidomethyl)-L-fucose (11 mg, 0.044 mmol, 54% 2 steps) as colorless oil. $^1$H NMR (500 MHz, Methanol-$d_4$) δ 3.94-3.87 (m, 2H, H-2, H-5), 3.85-3.75 (m, 2H, H-1$_{equatorial}$, C$\underline{H}_2$NHCO), 3.37-3.31 (m, 3H, H-1$_{axial}$, C$\underline{H}_2$NHCO, H-4), 2.52 (hept, J=6.9 Hz, 1H, C$\underline{H}_{isopropyl}$), 1.20 (d, J=6.4 Hz, 3H, H-6), 1.14 (d, J=6.4 Hz, 3H, C$\underline{H}_3$ $_{isopropyl}$), 1.13 (d, J=6.4 Hz, 3H, C$\underline{H}_3$ $_{isopropyl}$). $^{13}$C NMR (126 MHz, Methanol-$d_4$) δ 180.9 (CO), 75.9 (C-3), 74.1 (C-5), 73.0 (C-4), 70.9 (C-2), 68.9 (C-1), 40.4 ($\underline{C}H_2$NHCO), 36.3 ($\underline{C}H_{isopropyl}$), 20.1 (C$\underline{H}_3$ $_{isopropyl}$), 19.8 (C$\underline{H}_3$ $_{isopropyl}$), 17.1 (C-6). ESI-MS calcd. $C_{11}H_{22}NNaO_5^+$: 270.1; found: 270.0.

1.4.6 1-deoxy-3(S)—C-(isopropylsulfonamidomethyl)-L-fucose

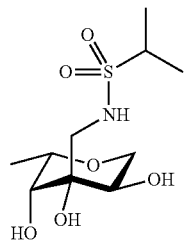

1-deoxy-2,4-di-O-benzyl-3-C—(S)-aminomethyl-L-fucose (0.03 mg, 0.08 mmol) and triethylamine (18 μL, 0.13 mmol) were dissolved in dry DMF (0.7 mL) and cooled to 0° C. Isopropanesulfonyl chloride (11 μL, 0.10 mmol) was added dropwise under nitrogen. The reaction was allowed to warm to r.t. and was stirred for further 4 h. Saturated aqueous NH$_4$Cl (3 mL) was added, and extracted with EtOAc (3×10 mL). The combined organic layers were dried over Na$_2$SO$_4$, filtered and concentrated in vacuo. The residue was purified by chromatography on silica (PE to PE/EtOAc=3:1). 1-deoxy-2,4-di-O-benzyl-3-C—(S)-isopropylsulfonamidomethyl-L-fucose (0.02 mg, 0.04 mmol) was obtained as light yellow oil and was subsequently debenzylated corresponding to general procedure for debenzylation. 1-deoxy-3(S)—C-(isopropylsulfonamidomethyl)-L-fucose (6 mg, 0.02 mmol, 31% 2 steps) as colorless oil. $^1$H NMR (500 MHz, Methanol-$d_4$) δ 3.90 (dd, J=10.7, 5.6 Hz, 1H, H-1$_{equatorial}$) 3.81 (qd, J=6.4, 1.4 Hz, 1H, H-5), 3.75 (dd, J=11.4, 5.6 Hz, 1H, H-2), 3.71 (d, J=1.3 Hz, 1H, H-4), 3.46 (d, J=14.2 Hz, 1H, C$\underline{H}_2$NHCO), 3.35-3.27 (m, 1H, C$\underline{H}_{isopropyl}$) 3.24 (dd, J=11.4, 10.7 Hz, 1H, H-1$_{axial}$), 1.34 (d, J=6.8 Hz, 3H, C$\underline{H}_3$ $_{isopropyl}$), 1.34 (d, J=6.8 Hz, 3H, C$\underline{H}_3$ $_{isopropyl}$), 1.21 (d, J=6.4 Hz, 3H, H-6). $^{13}$C NMR (126 MHz, Methanol-$d_4$) δ 75.3 (C-3), 73.8 (C-5), 72.5 (C-4), 70.9 (C-2), 69.1 (C-1), 53.8 ($\underline{C}H_2$NHCO), 44.1 ($\underline{C}H_{isopropyl}$) 17.2 (C-6), 17.1 (C$\underline{H}_3$ $_{isopropyl}$), 16.6 (C$\underline{H}_3$ $_{isopropyl}$). ESI-MS calcd. $C_{10}H_{22}NNaO_6^+$: 306.1; found: 306.0.

1.4.7 1-deoxy-4(S)—C-(methyl) L-Fucose

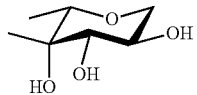

Purification of the reaction mixture yielded 1-deoxy-4(S)—C-(methyl) L-fucose (9.1 mg, 0.056 mmol, 97%) as colorless oil. $^1$H NMR (500 MHz, Methanol-$d_4$) δ 3.87 (dd, J=10.9, 5.6 Hz, 1H, H-1$_{equatorial}$), 3.70 (ddd, J=10.6, 9.2, 5.6 Hz, 1H, H-2), 3.29 (q, J=6.4 Hz, 1H, H-5), 3.16-3.06 (m, 2H, H-1$_{axial}$, H-3), 1.17 (d, J=6.4 Hz, 3H, H-6), 1.14 (s, 3H, C$\underline{H}_3$). $^{13}$C NMR (126 MHz, Methanol-$d_4$) δ 80.2 (C-5), 79.8 (C-3), 74.4 (C-4), 71.2 (C-1), 69.3 (C-2), 21.3 (C$\underline{H}_3$), 14.3 (C-6). HR-MS calcd. $C_7H_{14}NaO_4^+$: 185.0784; found: 185.0783.

1.4.8 1-deoxy-4(S)—C-(ethyl) L-Fucose

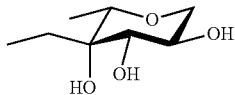

Purification of the reaction mixture yielded 1-deoxy-4 (S)—C-(ethyl) L-fucose (21.2 mg, 0.12 mmol, 56%) as colorless oil. $^1$H NMR (500 MHz, Methanol-$d_4$) δ 3.85 (dd, J=10.9, 5.6 Hz, 1H, H-1$_{equatorial}$), 3.76 (ddd, J=10.6, 9.1, 5.6 Hz, 1H, H-2), 3.45 (q, J=6.4 Hz, 1H, H-5), 3.34 (d, J=9.1 Hz, 1H, H-3), 3.09 (t, J=10.7 Hz, 1H, H-1$_{axial}$), 1.94 (dq, J=13.9, 7.8 Hz, 1H, C$\underline{H}_2$ $_{ethyl}$), 1.36 (dq, J=13.9, 7.6 Hz, 1H, C$\underline{H}_2$ $_{ethyl}$), 1.15 (d, J=6.4 Hz, 3H, H-6), 0.86 (t, J=7.7 Hz, 3H, C$\underline{H}_3$ $_{ethyl}$). $^{13}$C NMR (126 MHz Methanol-$d_4$) δ 77.4 (C-5), 76.5 (C-4), 75.5 (C-3), 71.1 (C-1), 69.5 (C-2), 27.5 ($\underline{C}H_2$ $_{ethyl}$), 14.0 (C-6), 8.4 ($\underline{C}H_3$ $_{ethyl}$). HR-MS calcd. $C_8H_{16}NaO_4^+$: 199.0941; found: 199.0939.

1.4.9 1-deoxy-4(S)—C-(propyl) L-Fucose

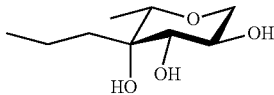

Purification of the reaction mixture yielded 1-deoxy-4 (S)—C-(propyl) L-fucose (33.8 mg, 0.177 mmol, 86%) as colorless oil. $^1$H NMR (500 MHz, Methanol-$d_4$) δ 3.85 (dd, J=10.9, 5.6 Hz, 1H, H-1$_{equatorial}$), 3.75 (ddd, J=10.6, 9.1, 5.6 Hz, 1H, H-2), 3.42 (q, J=6.4 Hz, 1H, H-5), 3.37-3.28 (m, 1H, H-3), 3.08 (t, J=10.7 Hz, 1H, H-1$_{axial}$), 1.94-1.81 (m, 1H, C$\underline{H}_2$ $_{propyl}$), 1.40-1.17 (m, 3H, C$\underline{H}_2$ $_{propyl}$), 1.15 (d, J=6.4 Hz, 3H, H-6), 0.93 (t, J=7.0 Hz, 3H, C$\underline{H}_3$ $_{propyl}$). $^{13}$C NMR (126 MHz, Methanol-$d_4$) δ 77.8 (C-5), 76.2 (C-3), 76.2 (C-4), 71.1 (C-1), 69.5 (C-2), 37.6 ($\underline{C}H_2$ $_{propyl}$), 18.0 ($\underline{C}H_2$ $_{propyl}$), 15.2 (C-6), 14.1 ($\underline{C}H_3$ $_{propyl}$). HR-MS calcd. $C_9H_{18}NaO_4^+$: 213.1097; found: 213.1093.

1.4.10 1-deoxy-4(S)—C-(butyl) L-Fucose

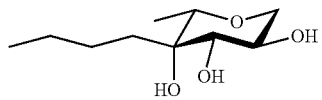

Purification of the reaction mixture yielded 1-deoxy-4 (S)—C-(butyl) L-fucose (18.4 mg, 0.09 mmol, 90%) as colorless oil. $^1$H NMR (500 MHz, Methanol-$d_4$) δ 3.85 (dd, J=10.9, 5.6 Hz, 1H, H-1$_{equatorial}$), 3.75 (ddd, J=10.6, 9.1, 5.6 Hz, 1H, H-2), 3.43 (q, J=6.4 Hz, 1H, H-5), 3.34-3.29 (m, 1H, H-2), 3.08 (t, J=10.7 Hz, 1H, H-1$_{axial}$), 1.94-1.85 (m, 1H, C$\underline{H}_2$ $_{butyl}$), 1.39-1.25 (m, 4H, C$\underline{H}_2$ $_{butyl}$), 1.24-1.16 (m, 1H, C$\underline{H}_2$ $_{butyl}$), 1.15 (d, J=6.4 Hz, 3H, H-6), 0.98-0.89 (m, 3H, C$\underline{H}_3$ $_{butyl}$). $^{13}$C NMR (126 MHz, Methanol-$d_4$) δ 77.8 (C-5), 76.3 (C-3), 76.2 (C-4), 71.1 (C-1), 69.5 (C-2), 34.9 ($\underline{C}H_2$ $_{butyl}$), 26.9 ($\underline{C}H_2$ $_{butyl}$), 24.5 ($\underline{C}H_2$ $_{butyl}$), 14.3 ($\underline{C}H_3$ $_{butyl}$), 14.1 (C-6). HR-MS calcd. $C_{10}H_{20}NaO_4^+$: 227.1254; found: 227.1251.

1.4.11 1-deoxy-4(S)—C-(hexyl) L-Fucose

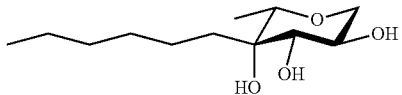

Purification of the reaction mixture yielded 1-deoxy-4 (S)—C-(hexyl) L-fucose (17.5 mg, 0.075 mmol, 72%) as colorless oil. $^1$H NMR (500 MHz, Methanol-$d_4$) δ 3.86 (dd, J=10.9, 5.7 Hz, 1H, H-1$_{equatorial}$), 3.76 (ddd, J=10.6, 9.1, 5.6 Hz, 1H, H-2), 3.44 (q, J=6.4 Hz, 1H, H-5), 3.34-3.32 (m, 1H, H-2), 3.09 (t, J=10.7 Hz, 1H, H-1$_{axial}$), 1.96-1.83 (m, 1H, C$\underline{H}_2$ $_{hexyl}$), 1.40-1.17 (m, 9H, C$\underline{H}_2$ $_{hexyl}$), 1.16 (d, J=6.4 Hz, 3H, H-6), 0.94-0.90 (m, 3H, C$\underline{H}_3$ $_{hexyl}$). $^{13}$C NMR (126 MHz, Methanol-$d_4$) δ 77.8 (C-5), 76.3 (C-3), 76.2 (C-4), 71.1 (C-1), 69.5 (C-2), 35.2 ($\underline{C}H_2$ $_{hexyl}$), 32.8 ($\underline{C}H_2$ $_{hexyl}$), 31.2 ($\underline{C}H_2$ $_{hexyl}$), 24.7 ($\underline{C}H_2$ $_{hexyl}$), 23.7 ($CH_2$ $_{hexyl}$), 14.4 ($\underline{C}H_3$ $_{hexyl}$), 14.1 (C-6). HR-MS calcd. $C_{12}H_{24}NaO_4^+$: 255.1567; found: 255.1567.

1.4.12 1-deoxy-4(S)—C-(phenyl) L-Fucose

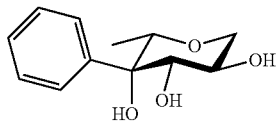

Purification of the reaction mixture yielded 1-deoxy-4 (S)—C-(phenyl) L-fucose (27.0 mg, 0.104 mmol, 86%) as colorless solid. $^1$H NMR (500 MHz, Methanol-$d_4$) δ 7.53-7.47 (m, 2H, C$\underline{H}_{phenyl}$), 7.38-7.33 (m, 2H, C$\underline{H}_{phenyl}$), 7.27-7.22 (m, 1H, C$\underline{H}_{phenyl}$), 3.98 (dd, J=11.0, 5.5 Hz, 1H, H-1$_{equatorial}$), 3.89 (ddd, J=10.6, 8.9, 5.5 Hz, 1H, H-2), 3.78 (d, J=8.9 Hz, 1H, H-3), 3.74 (q, J=6.4 Hz, 1H), H-5, 3.39-3.33 (m, 1H, H-1$_{axial}$), 0.84 (d, J=6.4 Hz, 3H, H-6). $^{13}$C NMR (126 MHz, Methanol-$d_4$) δ 143.5 ($\underline{C}_{phenyl}$), 129.1 ($\underline{C}H_{phenyl}$), 127.9 ($\underline{C}H_{phenyl}$), 126.8 ($\underline{C}H_{phenyl}$), 80.7 (C-5), 80.0 (C-3), 79.2 (C-4), 71.2 (C-1), 69.5 (C-2), 14.3 (C-6). HR-MS calcd. $C_{12}H_{16}NaO_4^+$: 247.0941; found: 247.0940.

1.4.13 1-deoxy-4(S)—C-(benzyl) L-Fucose

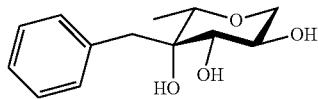

Purification of the reaction mixture yielded 1-deoxy-4 (S)—C-(benzyl) L-fucose (24.9 mg, 0.105 mmol, 95%) as colorless solid. $^1$H NMR (500 MHz, Methanol-$d_4$) δ 7.33-7.19 (m, 5H, C$\underline{H}_{benzyl}$), 3.79-3.69 (m, 2H, H-1$_{equatorial}$, H-2), 3.24-3.17 (m, 3H, H-3, H-5, C$\underline{H}_2$ $_{benzyl}$), 2.79 (t, J=12.4 Hz, 1H, H-1$_{axial}$), 2.66 (d, J=13.3 Hz, 1H, C$\underline{H}_2$ $_{benzyl}$), 1.36 (d, J=6.3 Hz, 3H, H-6). $^{13}$C NMR (126 MHz, Methanol-$d_4$) δ 137.9 ($\underline{C}_{benzyl}$), 131.4 ($\underline{C}H_{benzyl}$), 129.3 ($\underline{C}H_{benzyl}$), 127.6 ($\underline{C}H_{benzyl}$), 77.2 (C-5), 76.9 (C-3), 75.3 (C-4), 70.8 (C-1), 69.6 (C-2), 40.9 ($\underline{C}H_2$ $_{benzyl}$), 14.9 (C-6). HR-MS calcd. $C_{13}H_{18}NaO_4^+$: 261.1097; found: 261.1095.

1.4.14 1-deoxy-4(S)—C-(cyclohexyl) L-Fucose

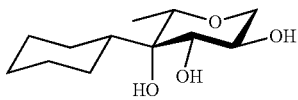

Purification of the reaction mixture yielded 1-deoxy-4 (S)—C-(cyclohexyl) L-fucose (40.8 mg, 0.177 mmol, 88%) as colorless solid. $^1$H NMR (500 MHz, Methanol-$d_4$) δ 3.83 (dd, J=10.9, 5.7 Hz, 1H, H-1$_{equatorial}$), 3.70 (ddd, J=10.7, 8.9, 5.7 Hz, 1H, H-2), 3.47 (q, J=6.4 Hz, 1H, H-5), 3.40 (d, J=8.9 Hz, 1H, H-3), 3.07 (t, J=10.8 Hz, 1H, H-1$_{axial}$), 1.92 (dq, J=14.2, 2.3 Hz, 1H, C$\underline{H}_{2\ cyclohexyl}$), 1.84-1.60 (m, 6H, C$\underline{H}_{cyclohexyl}$, C$\underline{H}_{2\ cyclohexyl}$), 1.49-1.36 (m, 1H, C$\underline{H}_{2\ cyclohexyl}$), 1.27-1.19 (m, 2H, C$\underline{H}_{2\ cyclohexyl}$), 1.17 (d, J=6.4 Hz, 3H, H-6). $^{13}$C NMR (126 MHz, Methanol-$d_4$) δ 78.1 (C-5), 77.6 (C-4), 76.7 (C-3), 71.1 (C-1), 70.1 (C-2), 45.0 (C$\underline{H}_{cyclohexyl}$), 29.5 (C$\underline{H}_{2\ cyclohexyl}$), 29.0 (C$\underline{H}_{2\ cyclohexyl}$), 28.8 (C$\underline{H}_{2\ cyclohexyl}$), 28.4 (C$\underline{H}_{2\ cyclohexyl}$), 27.9 (C$\underline{H}_{2\ cyclohexyl}$), 15.3 (C-6). HR-MS calcd. $C_{12}H_{22}NaO_4^+$: 253.1410; found: 253.1403.

1.4.15 1-deoxy-4(S)—C-(isopentyl) L-Fucose

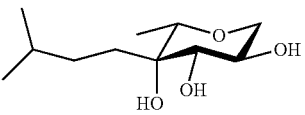

Purification of the reaction mixture yielded 1-deoxy-4 (S)—C-(isopentyl) L-fucose (43.7 mg, 0.200 mmol, 91%) as colorless oil. $^1$H NMR (500 MHz, Methanol-$d_4$) δ 3.85 (dd, J=10.9, 5.6 Hz, 1H, H-1$_{equatorial}$), 3.75 (ddd, J=10.6, 9.1, 5.6 Hz, 1H, H-2), 3.42 (q, J=6.3 Hz, 1H, H-5), 3.33-3.28 (m, 1H, H-3), 3.08 (t, J=10.8 Hz, 1H, H-1$_{axial}$), 1.91 (td, J=13.1, 3.8 Hz, 1H, C$\underline{H}_{2\ isopentyl}$), 1.50 (dp, J=13.2, 6.7 Hz, 1H, C$\underline{H}_{isopentyl}$), 1.32 (td, J=12.9, 3.9 Hz, 1H, C$\underline{H}_{2\ isopentyl}$), 1.24 (tdd, J=12.9, 5.8, 3.7 Hz, 1H, C$\underline{H}_{2\ isopentyl}$), 1.14 (d, J=6.4 Hz, 3H, H-6), 1.08-0.99 (m, 1H, C$\underline{H}_{2\ isopentyl}$), 0.92 (d, J=5.0 Hz, 3H, C$\underline{H}_{3\ isopentyl}$), 0.91 (d, J=5.0 Hz, 3H, C$\underline{H}_{3\ isopentyl}$). $^{13}$C NMR (126 MHz, Methanol-$d_4$) δ 77.7 (C-5), 76.3 (C-3), 76.1 (C-4), 71.1 (C-1), 69.6 (C-2), 33.6 (C$\underline{H}_{2\ isopentyl}$), 32.9 (C$\underline{H}_{2\ isopentyl}$), 29.9 (C$\underline{H}_{isopentyl}$), 23.1 (C$\underline{H}_{3\ isopentyl}$), 22.7 (C$\underline{H}_{3\ isopentyl}$), 14.0 (C-6). HR-MS calcd. $C_{11}H_{22}NaO_4^+$: 241.1410; found: 241.1410.

1.4.16 1-deoxy-4(S)—C-(cyanomethyl) L-Fucose

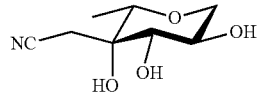

Purification of the reaction mixture yielded 1-deoxy-4 (S)—C-(cyanomethyl) L-fucose (24.8 mg, 0.132 mmol, 77%) as colorless solid. $^1$H NMR (500 MHz, Methanol-$d_4$) δ 3.89 (dd, J=11.0, 5.6 Hz, 1H, H-1$_{equatorial}$) 3.73 (ddd, J=10.7, 9.1, 5.6 Hz, 1H, H-2), 3.57 (q, J=6.4 Hz, 1H, H-5), 3.36 (d, J=9.1 Hz, 1H, H-3), 3.16 (t, J=10.8 Hz, 1H, H-1$_{axial}$), 2.92 (d, J=17.0 Hz, 1H, C$\underline{H}_2$CN), 2.57 (d, J=17.0 Hz, 1H, C$\underline{H}_2$CN), 1.25 (d, J=6.4 Hz, 3H, H-6). $^{13}$C NMR (126 MHz, Methanol-$d_4$) δ 118.2 (CH$_2$$\underline{C}$N), 78.0 (C-5), 77.0 (C-3), 74.6 (C-4), 71.2 (C-1), 69.0 (C-2), 23.2 ($\underline{C}H_2$CN), 14.3 (C-6). ESI-MS calcd. $C_8H_{23}NNaO_4^+$: 210.1; found: 209.9.

1.5 General Procedure for Sulfonamide Couplings

β-L-fucopyranosyl methylamine (1 eq.) and triethylamine (1.5 eq.) were dissolved in dry DMF (1.5 mL) and cooled to 0° C. The sulfonyl chloride (1.2 eq.) dissolved in DMF (0.08 M) was added dropwise under nitrogen. The reaction was allowed to warm to r.t. and was stirred for further 1-3 h. Saturated aqueous NH$_4$Cl was added, and extracted with EtOAc. The combined organic layers were dried over Na$_2$SO$_4$, filtered and concentrated in vacuo. The residue was purified by chromatography on silica (CH$_2$Cl$_2$ to CH$_2$Cl$_2$/EtOH=10:1 or CH$_2$Cl$_2$/MeOH=10:1).

1.5.1 2,4,6-Trimethylphenylsulfonamide-N-((β-L-fucopyranosyl methyl)

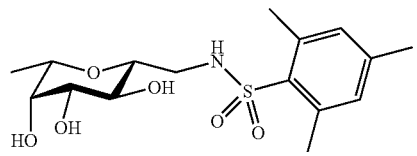

2,4,6-Trimethylphenylsulfonamide-N-((β-L-fucopyranosyl methyl) (79.3 mg, 0.22 mmol, 72%) was obtained from 2,4,6-Trimethylphenylsulfonchloride as colorless solid. $^1$H NMR (400 MHz, Methanol-$d_4$) δ 7.01 (s, 2H, C$\underline{H}_{phenyl}$), 3.56 (d, J=3.1 Hz, 1H, H-4), 3.41-3.21 (m, 3H, C$\underline{H}_2$NH, H-3, H-2), 3.03-2.91 (m, 2H, C$\underline{H}_2$NH, H-1), 2.62 (s, 6H, 2×CH$_3$), 2.29 (s, 3H, CH$_3$), 1.17 (d, J=6.5 Hz, 3H, H-6). $^{13}$C NMR (101 MHz, Methanol-$d_4$) δ 143.4 (C$_{phenyl}$), 140.3 (C$_{phenyl}$), 135.6 (C$_{phenyl}$), 132.9 (CH$_{phenyl}$), 79.2 (C-2), 76.3 (C-3), 75.5 (C-5), 73.5(C-4), 69.8 (C-1), 44.9 ($\underline{C}H_2$NH), 23.1 (2×$\underline{C}H_3$), 20.9 ($\underline{C}H_3$), 17.0 (C-6). ESI-MS calcd. $C_{16}H_{26}NO_6S^+$: 360.1; found: 360.1.

1.5.2 2-Thiophenesulfonamide, N-((β-L-fucopyranosyl methyl)

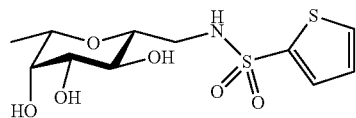

2-Thiophenesulfonamide, N-((β-L-fucopyranosyl methyl) (37.1 mg, 0.11 mmol, 68%) was obtained from 2-Thiophenesulfonchloride as colorless oil. $^1$H NMR (500 MHz, Methanol-$d_4$) δ 7.76 (d, J=5.0, 1.3 Hz, 1H, C$\underline{H}_{thiophene}$), 7.62 (dd, J=3.7, 1.4 Hz, 1H, C$\underline{H}_{thiophene}$), 7.14 (dd, J=5.0, 3.7 Hz, 1H, C$\underline{H}_{thiophene}$), 3.60 (dd, J=3.0, 1.1 Hz, 1H, H-4), 3.50 (qd, J=6.5, 1.1 Hz, 1H, H-5), 3.46-3.35 (m, 3H, H-1, H-3, C$\underline{H}_2$NH), 3.20-3.14 (m, 1H, H-2), 3.07 (dd, J=12.9, 7.2 Hz, 1H, C$\underline{H}_2$NH), 1.20 (d, J=6.5 Hz, 3H). $^{13}$C NMR (126 MHz, Methanol-$d_4$) δ 142.8 (C$_{thiophene}$), 132.9 ($\underline{C}H_{thiophene}$), 132.9 ($\underline{C}H_{thiophene}$), 128.4 ($\underline{C}H_{thiophene}$), 79.5

(C-2), 76.3 (C-3), 75.5 (C-5), 73.6 (C-4), 69.7 (C-1), 45.8 (CH$_2$NH), 17.0 (C-6). ESI-MS calcd. C$_{11}$H$_{16}$NO$_6$S$_2^+$: 324.1; found: 324.1.

1.5.3 3-Thiophenesulfonamide, N-((β-L-fucopyranosyl methyl)

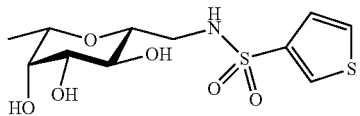

3-Thiophenesulfonamide, N-((β-L-fucopyranosyl methyl) (41.6 mg, 0.13 mmol, 76%) was obtained from 3-Thiophenesulfonchloride as colorless oil. $^1$H NMR (500 MHz, Methanol-d$_4$) δ 8.07 (dd, J=3.0, 1.3 Hz, 1H, CH$_{thiophene}$), 7.59 (dd, J=5.2, 3.0 Hz, 1H, CH$_{thiophene}$), 7.38 (dd, J=5.2, 1.3 Hz, 1H, CH$_{thiophene}$), 3.60 (dd, J=2.9, 1.1 Hz, 1H, H-4), 3.48 (qd, J=6.4, 1.1 Hz, 1H, H-5), 3.44-3.33 (m, 3H, H-1, H-3, CH$_2$NH), 3.17-3.11 (m, 1H, H-2), 3.04 (dd, J=13.0, 7.2 Hz, 1H, CH$_2$NH), 1.20 (d, J=6.4 Hz, 3H, H-6). $^{13}$C NMR (126 MHz, Methanol-d$_4$) δ 142.0 (C$_{thiophene}$), 131.2 (CH$_{thiophene}$), 129.2 (CH$_{thiophene}$), 126.6 (CH$_{thiophene}$), 79.5 (C-2), 76.3 (C-3), 75.5 (C-5), 73.6 (C-4), 69.7 (C-1), 45.6 (CH$_2$NH), 17.1 (C-6). ESI-MS calcd. C$_{11}$H$_{16}$NO$_6$S$_2^+$: 324.1; found: 324.0.

1.5.4 2-Thiophenesulfonamide, 5-methyl-N-((β-L-fucopyranosyl methyl)

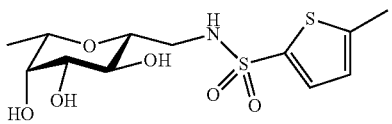

2-Thiophenesulfonamide, 5-methyl-N-(β-L-fucopyranosyl methyl) (40.3 mg, 0.12 mmol, 71%) was obtained from 5-Methyl-2-thiophensulfonylchloride as colorless oil. $^1$H NMR (500 MHz, Methanol-d$_4$) δ 7.40 (d, J=3.7 Hz, 1H, CH$_{thiophene}$), 6.88-6.79 (m, 1H, CH$_{thiophene}$), 3.61 (dd, J=3.0, 1.1 Hz, 1H, H-4), 3.51 (qd, J=6.5, 1.1 Hz, 1H, H-5), 3.46-3.33 (m, 3H, H-1, H-3, CH$_2$NH), 3.21-3.15 (m, 1H, H-2), 3.06 (dd, J=12.9, 7.1 Hz, 1H, CH$_2$NH), 2.53 (d, J=1.0 Hz, 3H, CH$_3$), 1.20 (d, J=6.4 Hz, 3H, H-6). $^{13}$C NMR (126 MHz, Methanol-d$_4$) δ 148.6 (C$_{thiophene}$), 139.6 (C$_{thiophene}$), 133.3 (CH$_{thiophene}$), 126.9 (CH$_{thiophene}$), 79.5 (C-2), 76.3 (C-3), 75.5 (C-5), 73.6 (C-4), 69.7 (C-1), 45.7 (CH$_2$NH), 17.0 (C-6), 15.3 (CH$_3$). ESI-MS calcd. C$_{12}$H$_{20}$NO$_6$S$_2^+$: 338.1; found: 338.1.

1.5.5 3-Thiophenesulfonamide, 2,5-dimethyl N-((β-L-fucopyranosyl methyl)

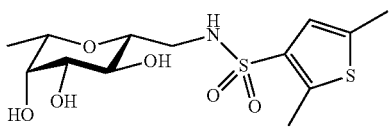

3-thiophenesulfonamide, 2,5-dimethyl-N-(β-L-fucopyranosyl methyl) (39.8 mg, 0.11 mmol, 67%) was obtained from 2,5-Dimethyl-2-thiophensulfonylchloride as colorless oil. $^1$H NMR (500 MHz, Methanol-d$_4$) δ 6.92 (q, J=1.2 Hz, 1H, CH$_{thiophene}$), 3.60 (dd, J=3.1, 1.1 Hz, 1H, H-4), 3.46 (qd, J=6.5, 1.1 Hz, 1H, H-5), 3.44-3.29 (m, 3H, H-1, H-3, CH$_2$NH), 3.14-3.07 (m, 1H, H-2), 3.02 (dd, J=13.0, 7.3 Hz, 1H, CH$_2$NH), 2.60 (s, 3H, CH$_3$), 2.39 (s, 3H, CH$_3$), 1.20 (d, J=6.5 Hz, 3H, H-6). $^{13}$C NMR (126 MHz, Methanol-d$_4$) δ 143.5 (C$_{thiophene}$), 137.7 (C$_{thiophene}$), 135.9 (C$_{thiophene}$), 126.6 (CH$_{thiophene}$), 79.4 (C-2), 76.3 (C-3), 75.6 (C-5), 73.6 (C-4), 69.8 (C-1), 45.3 (CH$_2$NH), 17.1 (C-6), 14.8 (CH$_3$), 14.2 (CH$_3$). ESI-MS calcd. C$_{13}$H$_{22}$NO$_6$S$_2^+$: 352.1; found: 352.1.

1.5.6 2-Thiophenesulfonamide, 5-bromo-N-((β-L-fucopyranosyl methyl)

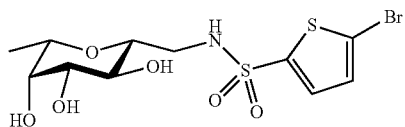

2-Thiophenesulfonamide, 5-bromo-N-(β-L-fucopyranosyl methyl) (43.6 mg, 0.11 mmol, 64%) was obtained from 5-Bromo-2-thiophensulfonylchloride as colorless oil. $^1$H NMR (500 MHz, Methanol-d$_4$) δ 7.40 (d, J=3.9 Hz, 1H, CH$_{thiophene}$), 7.18 (d, J=4.0 Hz, 1H, CH$_{thiophene}$), 3.64-3.58 (m, 1H, H-4), 3.51 (qd, J=6.5, 1.1 Hz, 1H, H-5), 3.43-3.36 (m, 3H, H-1, H-3, CH$_2$NH), 3.22-3.15 (m, 1H, H-2), 3.08 (dd, J=12.9, 7.2 Hz, 1H, CH$_2$NH), 1.20 (d, J=6.5 Hz, 3H, H-6). $^{13}$C NMR (126 MHz, Methanol-d$_4$) δ 144.2 (C$_{thiophene}$), 133.2 (CH$_{thiophene}$), 131.9 (CH$_{thiophene}$), 119.8 (C$_{thiophene}$), 79.5 (C-2), 76.3 (C-3), 75.5 (C-5), 73.6 (C-4), 69.7 (C-1), 45.7 (CH$_2$NH), 17.1 (C-6). ESI-MS calcd. C$_{11}$H$_{17}$BrNO$_6$S$_2^+$: 401.9; found: 401.9.

1.5.7 2-Thiophenesulfonamide, 4,5-dichloro-N-((β-L-fucopyranosyl methyl)

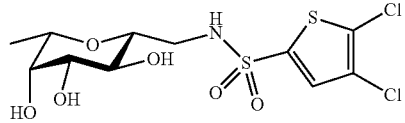

2-Thiophenesulfonamide, 4,5-dichloro-N-((β-L-fucopyranosyl methyl) (42.0 mg, 0.11 mmol, 63%) was obtained from 4,5-Dichloro-2-thiophensulfonylchloride as colorless oil. $^1$H NMR (500 MHz, Methanol-d$_4$) δ 7.51 (s, 1H, CH$_{thiophene}$), 3.63-3.60 (m, 1H, H-4), 3.51 (qd, J=6.5, 1.1 Hz, 1H. H-5), 3.45-3.36 (m, 3H, H-1, H-3, CH$_2$NH), 3.22-3.16 (m, 1H, H-2), 3.12 (dd, J=12.9, 7.2 Hz, 1H, CH$_2$NH), 1.19 (d, J=6.5 Hz, 3H, H-6). $^{13}$C NMR (126 MHz, Methanol-d$_4$) δ 140.5 (C$_{thiophene}$), 131.5 (CH$_{thiophene}$), 131.1 (C$_{thiophene}$), 125.6 (C$_{thiophene}$), 79.4 (C-2), 76.3 (C-3), 75.5 (C-5), 73.5 (C-4), 69.7 (C-1), 45.8 (CH$_2$NH), 17.1 (C-6). ESI-MS calcd. C$_{11}$H$_{16}$Cl$_2$NO$_6$S$_2^+$: 391.9; found: 391.9.

1.5.8 4-Isoxazolesulfonamide, 5-methyl-N-((β-L-fucopyranosyl methyl)

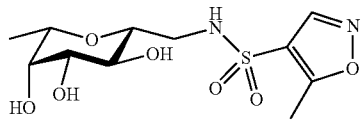

4-Isoxazolesulfonamide, 5-methyl-N-((β-L-fucopyranosyl methyl) (17.0 mg, 0.05 mmol, 19%) was obtained from 5-Methyl-4-isoxazolesulfonylchloride as colorless oil. $^1$H NMR (500 MHz, Methanol-$d_4$) δ 8.56 (d, J=0.8 Hz, 1H, C$\underline{H}_{isoxazole}$), 3.63-3.59 (m, 1H, H-4), 3.50 (qd, J=6.5, 1.1 Hz, 1H, H-5), 3.42-3.35 (m, 3H, H-1, H-3, C$\underline{H}_2$NH), 3.19-3.14 (m, 1H, H-2), 3.11 (dd, J=12.9, 7.1 Hz, 1H, C$\underline{H}_2$NH), 2.66 (d, J=0.7 Hz, 3H, C$\underline{H}_3$), 1.18 (d, J=6.5 Hz, 3H, H-6). $^{13}$C NMR (126 MHz, Methanol-$d_4$) δ 172.5 ($\underline{C}_{isoxazole}$), 150.2 (CH$_{isoxazole}$), 119.5 ($\underline{C}_{isoxazole}$), 79.5 (C-2), 76.3 (C-3), 75.5 (C-5), 73.5 (C-4), 69.6 (C-1), 45.3 ($\underline{C}H_2$NH), 17.0 (C-6), 11.8 ($\underline{C}H_3$). ESI-MS calcd. $C_{11}H_{19}N_2O_7S^+$: 323.1; found: 323.1.

1.5.9 1H-Pyrazole-4-sulfonamide, 1,3-dimethyl-N-(β-L-fucopyranosyl methyl)

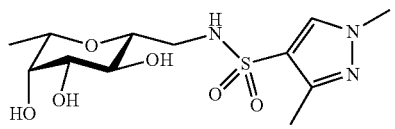

1H-Pyrazole-4-sulfonamide, 1,3-dimethyl-N-((β-L-fucopyranosyl methyl) (10.0 mg, 0.03 mmol, 11%) was obtained from 1,3-dimethyl-1H-Pyrazole-4-sulfonylchloride as colorless oil. $^1$H NMR (500 MHz, Methanol-$d_4$) δ 7.97 (s, 1H, C$\underline{H}_{pyrazole}$), 3.84 (s, 3H, NC$\underline{H}_3$), 3.61 (dd, J=3.0, 1.1 Hz, 1H, H-4), 3.51 (qd, J=6.4, 1.1 Hz, 1H, H-5), 3.45-3.36 (m, 2H, H-2, H-3), 3.31-3.27 (m, 1H, C$\underline{H}_2$NH), 3.15 (ddd, J=9.2, 7.0, 2.6 Hz, 1H), 3.03 (dd, J=13.0, 7.0 Hz, 1H), 2.36 (s, 3H), 1.20 (d, J=6.5 Hz, 3H). $^{13}$C NMR (126 MHz, Methanol-$d_4$) δ 148.6 ($\underline{C}_{pyrazole}$), 135.7 ($\underline{C}H_{pyrazole}$), 120.8 ($\underline{C}_{pyrazole}$), 79.4 (C-2), 76.4 (C-3), 75.6 (C-5), 73.6 (C-4), 69.7 (C-1), 45.3 ($\underline{C}H_2$NH), 39.1 (N$\underline{C}H_3$), 17.1 (C-6), 12.3 ($\underline{C}H_3$). ESI-MS calcd. $C_{12}H_{22}N_3O_6S^+$: 336.1; found: 336.1.

1.5.10 2-Furansulfonamide, N-((β-L-fucopyranosyl methyl) (SN03)

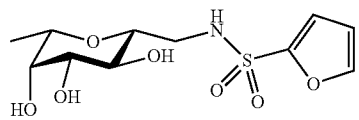

2-Furansulfonamide, N-((β-L-fucopyranosyl methyl) (SN03) (45 mg, 0.273 mmol, 52%) was obtained from furan-2-sulfonylchloride as colorless oil. $^1$H NMR (500 MHz, Methanol-$d_4$) δ 7.74-7.73 (m, 1H, C$\underline{H}_{furan}$), 7.04 (dd, J=3.47 Hz, J=0.95 Hz, 1H, C$\underline{H}_{furan}$) 6.60-6.57 (m, 1H, C$\underline{H}_{furan}$) 3.62-3.60 (m, 1H, H-4), 3.54-3.49 (m, 1H, C$\underline{H}_2$NH, H-1, H-5), 3.43-3.38 (m, 3H, H-3), 3.35 (s, 1H), 3.18-3.13 (m, 1H, H-2), 3.12-3.07 (m, 1H, C$\underline{H}_2$NH), 1.21 (d, J=6.62 Hz, 3H, C$\underline{H}_3$). $^{13}$C NMR (126 MHz, Methanol-$d_4$) δ 150.8 ($\underline{C}_{furan}$), 147.7 ($\underline{C}H_{furan}$), 116.7 ($\underline{C}H_{furan}$), 112.3 ($\underline{C}H_{furan}$), 79.8 (C-2), 76.5 (C-3), 75.7 (C-5), 73.7 (C-4), 69.8 (C-1), 45.6 ($\underline{C}H_2$), 17.2 (C-6). HR-MS calcd. $C_{11}H_{18}NO_7S^+$: 308.0798; found: 308.0800.

1.5.11 5-Methyl-2-trifluoromethyl-3-furansulfonamide, N-((β-L-fucopyranosyl methyl) (SN04)

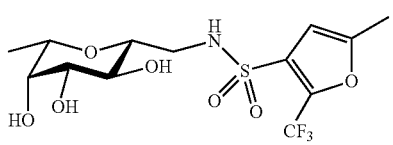

5-Methyl-2-trifluoromethyl-3-furansulfonamide, N-((β-L-fucopyranosyl methyl) (SN04) (45 mg, 0.273 mmol, 52%) was obtained from 5-methyl-2-trifluoromethyl-3-furansulfonylchloride as colorless oil. $^1$H NMR (500 MHz, Methanol-$d_4$) δ 7.19-7.17 (m, 1H, C$\underline{H}_{furan}$), 3.62-3.60 (m, 1H, H-4), 3.52-3.47 (m, 1H, H-5), 3.41-3.35 (m, 3H, C$\underline{H}_2$NH, H-1, H-3), 3.20-3.13 (m, 1H, H-2), 3.10-3.05 (m, 1H, C$\underline{H}_2$NH), 2.59 (s, 3H, furan-C$\underline{H}_3$), 1.19 (d, J=6.45 Hz, 3H, C$\underline{H}_3$). $^{13}$C NMR (126 MHz, Methanol-$d_4$) δ 159.5 ($\underline{C}_{furan}$), 140.08 (q, $^2J_{CF}$=43.6 Hz, $\underline{C}_{furan}$), 124.6 ($\underline{C}_{furan}$), 120.0 (q, $^1J_{CF}$=266.4 Hz, $\underline{C}F_3$), 113.4 (q, $^3J_{CF}$=2.9 Hz, $\underline{C}H_{furan}$), 79.5 (C-2), 76.3 (C-3), 75.5 (C-5), 73.5 (C-4), 69.6 (C-1), 45.3 ($\underline{C}H_2$), 17.0 (C-6), 13.0 (furan-$\underline{C}H_3$). $^{19}$F NMR (400 MHz, Methanol-$d_4$) δ 66.5 (C$\underline{F}_3$). HR-MS calcd. $C_{13}H_{19}F_3NO_7S^+$: 390.0829; found: 390.0844.

1.5.12 1-Methyl-1-H-pyrazole-3-sulfonamide, N-((β-L-fucopyranosyl methyl) (SN10f)

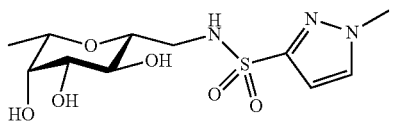

1-Methyl-1-H-pyrazole-3-sulfonamide, N-((β-L-fucopyranosyl methyl) (SN10f) (30 mg, 0.093 mmol, 33%) was obtained from 1-methyl-1H-pyrazole-3-sulfonylchloride as colorless oil. $^1$H NMR (400 MHz, Methanol-$d_4$) δ 7.72 (d, J=2.21 Hz, 1H, C$\underline{H}_{pyrazole}$), 6.66 (d, J=2.21 Hz, 1H, C$\underline{H}_{pyrazole}$), 3.96 (s, 3H, pyrazole-C$\underline{H}_3$), 3.63-3.61 (m, 1H, H-4), 3.56-3.50 (m, 1H, H-5), 3.47-3.39 (m, 3H, C$\underline{H}_2$NH, H-1, H-3), 3.23-3.18 (m, 1H, H-2), 3.16-3.10 (m, 1H, C$\underline{H}_2$NH), 1.21 (d, J=6.62 Hz, 3H, C$\underline{H}_3$). $^{13}$C NMR (101 MHz, Methanol-$d_4$) δ 152.06 ($\underline{C}_{pyrazole}$), 134.0 ($\underline{C}H_{pyrazole}$), 107.7 ($\underline{C}H_{pyrazole}$), 79.9 (C-2), 76.5 (C-3), 75.7 (C-5), 73.8 (C-4), 69.8 (C-1), 45.8 ($\underline{C}H_2$), 39.9 (pyrazole-$\underline{C}H_3$), 17.2 (C-6). HR-MS calcd. $C_{11}H_{20}N_3O_6S^+$: 322.1067; found: 322.1070.

1.5.13 2-Thiophenesulfonamide, 5-ethyl-N-((β-L-fucopyranosyl methyl) (SN11)

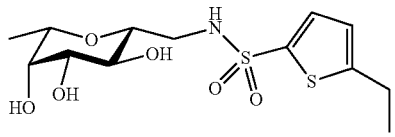

2-Thiophenesulfonamide, 5-ethyl-N-((β-L-fucopyranosyl methyl) (SN11) (32 mg, 0.091 mmol, 32%) was obtained from 5-ethyl-2-thiophensulfonylchloride as colorless oil. $^1$H NMR (400 MHz, Methanol-$d_4$) δ 7.43 (d, J=3.78 Hz, 1H, C$\underline{H}_{thiophen}$), 6.87 (d, J=3.78 Hz, 1H, C$\underline{H}_{thiophen}$), 3.62-3.60 (m, 1H, H-4), 3.54-3.48 (m, 1H, H-5), 3.45-3.34 (m, 3H, C$\underline{H}_2$NH, H-1, H-3), 3.20-3.15 (m, 1H, H-2), 3.08-3.03 (m, 1H, C$\underline{H}_2$NH), 2.91 (q, J=7.57 Hz, 2H, thiophen-C$\underline{H}_2$CH$_3$), 1.32 (t, J=7.57 Hz, 3H, thiophen-CH$_2$C$\underline{H}_3$), 1.19 (d, J=6.31 Hz, 3H, CH$_3$). $^{13}$C NMR (101 MHz, Methanol-$d_4$) δ 156.2 ($\underline{C}_{thiophen}$), 139.4 ($\underline{C}_{thiophen}$), 133.3 ($\underline{C}H_{thiophen}$), 125.3 ($\underline{C}H_{thiophen}$), 79.7 (C-2), 76.5 (C-3), 75.7 (C-5), 73.7 (C-4), 69.9 (C-1), 45.9 ($\underline{C}H_2$), 24.6 (thiophen-$\underline{C}H_2$CH$_3$), 17.2 (C-6), 16.3 (thiophen-CH$_2\underline{C}H_3$). HR-MS calcd. $C_{13}H_{22}NO_6S_2^+$: 352.0883; found: 352.0899.

1.5.14 2-Thiophenesulfonamide-4-methyl, N-((β-L-fucopyranosyl methyl) (SN13)

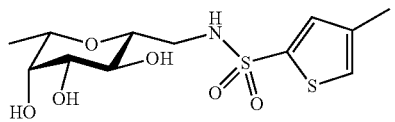

2-Thiophenesulfonamide-4-methyl, N-((β-L-fucopyranosyl methyl) (SN13) (26 mg, 0.078 mmol, 27%) was obtained from 4-methyl-2-thiophensulfonylchloride as colorless oil. $^1$H NMR (400 MHz, Methanol-$d_4$) δ 7.44-7.42 (m, 1H, C$\underline{H}_{thiophen}$), 7.35-7.33 (m, 1H, C$\underline{H}_{thiophen}$), 3.63-3.60 (m, 1H, H-4), 3.54-3.48 (m, 1H, H-5), 3.44-3.35 (m, 3H, C$\underline{H}_2$NH, H-1, H-3), 3.21-3.16 (m, 1H, H-2), 3.10-3.04 (m, 1H, C$\underline{H}_2$NH), 2.28 (s, 3H, thiophen-C$\underline{H}_3$), 1.21 (d, J=6.31 Hz, 3H, CH$_3$). $^{13}$C NMR (101 MHz, Methanol-$d_4$) δ 142.5 ($\underline{C}_{thiophen}$), 139.9 ($\underline{C}_{thiophen}$), 134.9 ($\underline{C}H_{thiophen}$), 128.6 ($\underline{C}H_{thiophen}$), 79.9 (C-2), 76.7 (C-3), 75.9 (C-5), 73.9 (C-4), 70.1 (C-1), 46.1 ($\underline{C}H_2$), 17.4 (C-6), 15.8 (thiophen-$\underline{C}H_3$) ppm. HR-MS calcd. $C_{12}H_{20}NO_6S_2^+$: 338.0727; found: 338.0720.

1.5.15 1-Methyl-1-H-imidazol-4-sulfonamide, N-((β-L-fucopyranosyl methyl) (SN15)

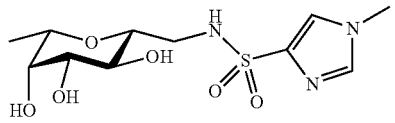

1-Methyl-1-H-imidazol-4-sulfonamide, N-((β-L-fucopyranosyl methyl) (SN15) (30.3 mg, 0.093 mmol, 33%) was obtained from 1-methyl-1-H-imidazol-4-sulfonylchloride as colorless oil. $^1$H NMR (400 MHz, Methanol-$d_4$) δ 7.76-7.75 (m, 1H, C$\underline{H}_{imidazole}$), 7.68-7.66 (m, 1H, C$\underline{H}_{imidazole}$), 3.79 (s, 3H, imidazole-C$\underline{H}_3$) 3.63-3.60 (m, 1H, H-4), 3.57-3.51 (m, 1H, H-5), 3.44-3.34 (m, 3H, C$\underline{H}_2$NH, H-1, H-3), 3.19-3.15 (m, 1H, H-2), 3.14-3.08 (m, 1H, C$\underline{H}_2$NH), 1.21 (d, J=6.31 Hz, 3H, CH$_3$). $^{13}$C NMR (101 MHz, Methanol-$d_4$) δ 141.2 ($\underline{C}H_{imidazole}$), 141.0 ($\underline{C}_{imidazole}$), 125.8 ($\underline{C}H_{imidazole}$), 79.9 (C-2), 76.4 (C-3), 75.7 (C-5), 73.7 (C-4), 69.7 (C-1), 45.7 ($\underline{C}H_2$), 34.5 (imidazole-$\underline{C}H_3$), 17.2 (C-6). HR-MS calcd. $C_{11}H_{20}N_3O_6S^+$: 322.1067; found: 322.1070.

1.5.16 3-Furansulfonamide-2,5-dimethyl, N-((β-L-fucopyranosyl methyl) (SH7)

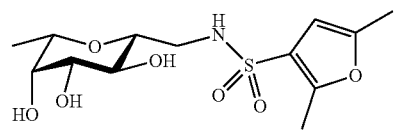

3-Furansulfonamide-2,5-dimethyl, N-((β-L-fucopyranosyl methyl) (SH7) (10 mg, 0.03 mmol, 17%) was obtained from 2,5-dimethyl-3-furansulfonylchloride as colorless solid. $^1$H NMR (400 MHz, Methanol-$d_4$) δ 6.19 (s, 1H, C$\underline{H}_{furan}$) 3.63-3.60 (m, 1H, H-4), 3.55-3.49 (m, 1H, H-5), 3.44-3.35 (m, 2H, H-1, H-3), 3.29-3.25 (m, 1H, C$\underline{H}_2$NH), 3.20-3.14 (m, 1H, H-2), 3.05-2.99 (m, 1H, C$\underline{H}_2$NH), 2.46 (s, 3H, furan-C$\underline{H}_3$), 2.25 (s, 3H, furan-C$\underline{H}_3$), 1.20 (d, 3H, J=6.31, C$\underline{H}_3$). $^{13}$C NMR (101 MHz, Methanol-$d_4$) δ 155.2 ($\underline{C}_{furan}$), 152.3 ($\underline{C}_{furan}$), 122.8 ($\underline{C}_{furan}$), 106.5 ($\underline{C}H_{furan}$), 79.8 (C-2), 76.5 (C-3), 75.7 (C-5), 73.8 (C-4), 69.9 (C-1), 45.5 (C$\underline{H}_2$NH), 17.2 ($\underline{C}H_3$), 13.2 (furan-$\underline{C}H_3$), 13.0 (furan-$\underline{C}H_3$). HR-MS calcd. $C_{13}H_{22}NO_7S^+$: 336.1111; found: 336.1101.

1.5.17 2-Thiophenesulfonamide-3-methyl, N-((β-L-fucopyranosyl methyl) (SH8)

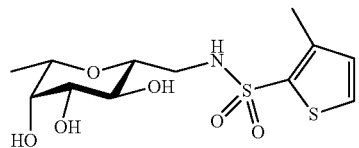

2-Thiophenesulfonamide-3-methyl, N-((β-L-fucopyranosyl methyl) (SH8) (24 mg, 0.07 mmol, 42%) was obtained from 3-methyl-2-thiophensulfonylchloride as colorless oil. $^1$H NMR (400 MHz, Methanol-$d_4$) δ 7.58 (d, J=5.04 Hz, 1H, C$\underline{H}_{thiophen}$), 7.00 (d, J=5.04 Hz, 1H, C$\underline{H}_{thiophen}$), 3.61-3.58 (m, 1H, H-4), 3.50-3.44 (m, 1H, H-5), 3.43-3.32 (m, 3H, C$\underline{H}_2$NH, H-1, H-3), 3.13-3.03 (m, 2H, C$\underline{H}_2$NH, H-2), 2.47 (s, 3H, thiophen-C$\underline{H}_3$), 1.20 (d, J=6.31 Hz, 3H, C$\underline{H}_3$). $^{13}$C NMR (101 MHz, Methanol-$d_4$) δ 143.2 ($\underline{C}_{thiophen}$), 136.0 ($\underline{C}_{thiophen}$), 133.0 ($\underline{C}H_{thiophen}$), 130.7 ($\underline{C}H_{thiophen}$), 79.5 (C-2), 76.5 (C-3), 75.7 (C-5), 73.7 (C-4), 69.8 (C-1), 45.6 ($\underline{C}H_2$), 17.2 ($\underline{C}H_3$), 14.9 (thiophen-$\underline{C}H_3$). HR-MS calcd. $C_{12}H_{20}NO_6S_2^+$: 338.0727; found: 338.0732.

1.5.18 1-Methyl-1-H-pyrazole-4-sulfonamide, N-((β-L-fucopyranosyl methyl) (SH11)

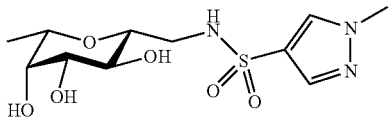

1-Methyl-1-H-pyrazole-4-sulfonamide, N-((β-L-fucopyranosyl methyl) (SH11) (26 g, 0.08 mmol, 47%) was obtained from 1-methyl-1-H-pyrazole-4-sulfonylchloride as colorless solid. $^1$H NMR (400 MHz, Methanol-$d_4$) δ 8.08 (s, 1H, C$\underline{H}_{pyrazole}$), 7.76 (s, 1H, C$\underline{H}_{pyrazole}$), 3.93 (s, 3H, pyrazole-C$\underline{H}_3$), 3.63-3.60 (m, 1H, H-4), 3.55-3.50 (m, 1H, H-5), 3.45-3.38 (m, 2H, H-1, H-3), 3.34-3.32 (m, 1H, C$\underline{H}_2$NH), 3.22-3.17 (m, 1H, H-2), 3.06-3.01 (m, 1H, C$\underline{H}_2$NH), 1.19 (d, J=6.31 Hz, 3H, C$\underline{H}_3$). $^{13}$C NMR (101 MHz, Methanol-$d_4$) δ 139.5 ($\underline{C}H_{pyrazole}$), 133.8 ($\underline{C}H_{pyrazole}$), 124.0 ($C_{pyrazole}$), 79.7 (C-2), 76.5 (C-3), 75.7 (C-5), 73.7 (C-4), 69.8 (C-1), 45.7 ($\underline{C}H_2$), 39.6 (pyrazole-$\underline{C}H_3$), 17.2 ($\underline{C}H_3$). HR-MS calcd. $C_{11}H_{20}N_3O_6S^+$: 322.1067; found: 322.1064.

1.5.19 2-Thiophenesulfonamide, 5-(2-phenylethynyl)-N-((β-L-fucopyranosyl methyl) (RS424)

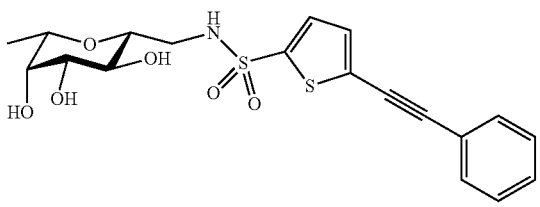

2-Thiophenesulfonamide, 5-(2-phenylethynyl)-N-((β-L-fucopyranosyl methyl) (RS424). The solution of 2-Thiophenesulfonamide-5-bromo, N-((β-L-fucopyranosyl methyl) (DH181e) (30 mg, 0.07 mmol), CuI (0.7 mg, 0.004 mmol), Pd(PPh$_3$)$_2$Cl$_2$ (1.3 mg, 0.002 mmol), phenyl acetylene (0.1 mL, 0.09 mmol) and Et$_3$N (20 μL 0.15 mmol) in DMF (2.5 mL) was degassed (100 mbar) at 0° C. The reaction mixture was stirred under argon atmosphere at 50° C. for 3 h and monitored by LCMS. Phenyl acetylene (0.1 mL, 0.09 mmol) was added and the reaction mixture was stirred at 50° C. for 14 h and poured into H$_2$O (4 mL). The organic organic phase was separated and the aqueous phase was extracted with EtOAc (7×3 mL). The combined organic layers were dried over Na$_2$SO$_4$ and the solvent was removed in vacuo. The residue was purified by HPLC (VP250/10 Nucleodur C-18 Gravity SB, 5 μm from Macherey Nagel, 8 mL/min, Eluent A: H$_2$O, Eluent B: MeCN, 0 min 30% B, 0-40 min 30%-50% B). After lyophilisation (RS424) was obtained as white solid (18.4 mg, 0.043 mmol, 59%). $^1$H NMR (500 MHz, Methanol-$d_4$) δ 7.57-7.50 (m, 3H, C$\underline{H}_{thiophen}$, C$\underline{H}_{phenyl}$), 7.41 (dd, J=5.2, 2.0 Hz, 3H, C$\underline{H}_{phenyl}$), 7.29 (d, J=3.8 Hz, 1H, C$\underline{H}_{thiophenl}$), 3.64-3.59 (m, 1H, H-4), 3.52 (qd, J=6.5, 1.1 Hz, 1H, H-5), 3.45-3.38 (m, 3H, H-2, H-3, C$\underline{H}_2$NH), 3.20 (ddd, J=9.3, 7.2, 2.2 Hz, 1H, H-1), 3.11 (dd, J=12.9, 7.2 Hz, 1H, C$\underline{H}_2$NH), 1.21 (d, J=6.4 Hz, 3H, H-6). $^{13}$C NMR (126 MHz, Methanol-$d_4$) δ 143.5 (ArC), 133.0 (ArC), 132.7 (ArC), 132.6 (ArC), 130.4 (ArC), 130.1 (ArC), 129.7 (ArC), 123.2 (ArC), 96.7 ($C_{ethynyl}$), 81.7 ($C_{ethynyl}$), 79.6 (C-1), 76.3 (C-2/C-3), 75.6 (C-5), 73.6 (C-4), 69.7 (C-2/C-3), 45.8 ($\underline{C}H_2$NH), 17.1 (C-6). ESI-MS calcd. $C_{19}H_{22}NO_6S_2^+$: 424.1; found: 424.1.

1.6 Compounds Obtained by Carboxamide Couplings

1.6.1 Benzamide, N-((β-L-fucopyranosyl methyl) (SH1)

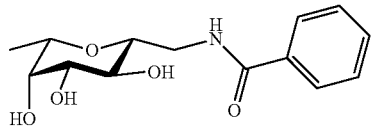

Benzamide, N-((β-L-fucopyranosyl methyl) (SH1) (37 mg, 0.132 mmol, 23%) was obtained from benzoylchloride as colorless solid. $^1$H NMR (400 MHz, Methanol-$d_4$) δ 7.82-7.81 (m, 2H, C$\underline{H}_{phenyl}$), 7.56-7.51 (m, 1H, C$\underline{H}_{phenyl}$), 7.78-7.44 (m, 2H, C$\underline{H}_{phenyl}$), 3.71 (m, 2H, C$\underline{H}_2$NH), 3.67-3.64 (m, 1H, H-4), 3.64-3.60 (m, 1H, H-5), 3.50-3.48 (m, 2H, H-1, H-3), 3.35-3.32 (m, 1H, H-2), 1.25 (d, J=3.61 Hz, CH$_3$). $^{13}$C NMR (101 MHz, Methanol-$d_4$) δ 170.9 (C=O), 135.9 ($C_{phenyl}$), 132.7 ($\underline{C}H_{phenyl}$), 129.6 ($\underline{C}H_{phenyl}$), 128.5 ($\underline{C}H_{phenyl}$), 80.0 (C-2), 76.3 (C-3), 75.8 (C-5), 73.7 (C-4), 69.9 (C-1), 42.6 ($\underline{C}H_2$), 17.2 (C-6) ppm. HR-MS calcd. $C_{14}H_{20}NO_5^+$: 282.1336; found: 282.1345.

1.6.2 2-Benzo[b]thiophene amide, N-((β-L-fucopyranosyl methyl) (SH2)

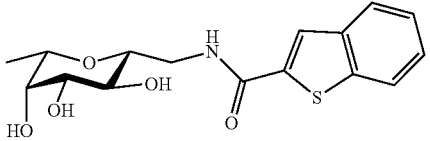

2-Benzo[b]thiophene amide, N-((β-L-fucopyranosyl methyl) (SH2) (12 mg, 0.036 mmol, 21%) was obtained from benzo[b]thiophene-2-carbonylchloride as yellowish solid. $^1$H NMR (400 MHz, Methanol-$d_4$) δ 7.99 (s, 1H, C$\underline{H}_{benzothiophen}$), 7.93-7.88 (m, 2H, C$\underline{H}_{benzothiophen}$), 7.46-7.39 (m, 2H, C$\underline{H}_{benzothiophen}$), 3.77-3.72 (m, 1H, C$\underline{H}_2$NH), 3.70-3.61 (m, 3H, C$\underline{H}_2$NH, H-4, H-5), 3.54-3.46 (m, 2H, H-1, H-3), 3.38-3.33 (m, 1H, H-2), 1.28 (d, J=6.31 Hz, 3H, CH$_3$). $^{13}$C NMR (101 MHz, Methanol-$d_4$) δ 165.4 (C=O), 142.6 ($C_{benzothiophen}$), 140.9 ($C_{benzothiophen}$), 140.0 ($C_{benzothiophen}$), 127.6 ($\underline{C}H_{benzothiophen}$), 126.8 ($\underline{C}H_{benzothiophen}$), 126.4 ($\underline{C}H_{benzothiophen}$), 126.1 ($\underline{C}H_{benzothiophen}$), 123.3 ($\underline{C}H_{benzothiophen}$), 80.0 (C-2), 76.4 (C-3), 76.0 (C-5), 73.8 (C-4), 70.0 (C-1), 42.8 ($\underline{C}H_2$), 17.3 ($\underline{C}H_3$). HR-MS calcd. $C_{16}H_{19}NO_5S^+$: 338.1057; found: 338.1045.

1.6.3 2-phenyl-1,3-thiazol amide, N-((β-L-fucopyranosyl methyl) (SH3)

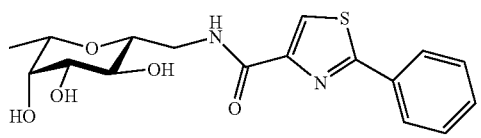

2-phenyl-1,3-thiazol amide, N-((β-L-fucopyranosyl methyl) (SH3) (30 mg, 0.08 mmol, 49%) was obtained from 2-phenyl-1,3-thiazol-4-carbonylchloride as yellowish solid. $^1$H NMR (400 MHz, Methanol-d$_4$) δ 8.20 (s, 1H, C$\underline{H}_{thiazol}$), 8.05-8.02 (m, 2H, C$\underline{H}_{phenyl}$), 7.52-7.49 (m, 3H, C$\underline{H}_{phenyl}$), 3.90-3.85 (m, 1H, C$\underline{H}_2$NH), 3.68-3.63 (m, 2H, H-4, H-5), 3.62-3.56 (m, 1H, C$\underline{H}_2$NH), 3.52-3.49 (m, 2H, H-1, H-3), 3.38-3.32 (m, 1H, H-2), 1.29 (d, J=6.62 Hz, CH$_3$). $^{13}$C NMR (101 MHz, Methanol-d$_4$) δ 170.0 (C=O), 163.8 (C$_{thiazol}$), 151.7 (C$_{thiazol}$), 134.3 (C$_{phenyl}$), 132.1 (CH$_{phenyl}$), 130.4 (2×C, $\underline{C}$H$_{phenyl}$), 127.9 (2×C, $\underline{C}$H$_{phenyl}$), 124.9 ($\underline{C}$H$_{thiazol}$), 80.1 (C-2), 76.4 (C-3), 76.0 (C-5), 73.7 (C-4), 70.6 (C-1), 42.4 ($\underline{C}$H$_2$), 17.4 ($\underline{C}$H$_3$). HR-MS calcd. C$_{17}$H$_{21}$N$_2$O$_5$S$^+$: 365.1166; found: 365.1185.

1.6.4 5-phenyl-2-thiophene amide, N-((β-L-fucopyranosyl methyl) (SH4)

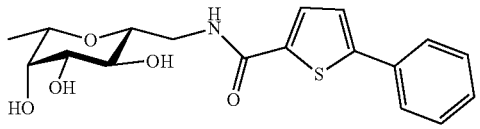

5-phenyl-2-thiophene amide, N-((β-L-fucopyranosyl methyl) (SH4) (26 mg, 0.07 mmol, 42%) was obtained from 5-phenyl-2-thiophene carbonylchloride as colorless solid. $^1$H NMR (400 MHz, Methanol-d$_4$) δ 8.53 (t, J=5.36 Hz, 1H, —NH), 7.83 (d, J=3.78 Hz, 1H, C$\underline{H}_{thiophen}$), 7.70 (d, J=7.25 Hz, 2H, C$\underline{H}_{phenyl}$), 7.53 (d, J=4.10 Hz, 1H, C$\underline{H}_{thiophen}$), 7.44 (t, J=7.57 Hz, 2H, C$\underline{H}_{phenyl}$), 7.36 (t, J=7.25 Hz, 1H, C$\underline{H}_{phenyl}$), 4.89 (d, J=4.73 Hz, 1H, OH), 4.68 (d, J=5.36 Hz, 1H, OH), 4.37 (d, J=4.73 Hz, 1H, OH), 3.71-3.65 (m, 1H, C$\underline{H}_2$NH), 3.51-3.43 (m, 2H, H-4, H-5), 3.34-3.15 (m, 4H, C$\underline{H}_2$NH, H-1, H-2, H-3), 1.12 (d, J=6.62 Hz, 3H, C$\underline{H}_3$). $^{13}$C NMR (101 MHz, DMSO-d$_6$) δ 161.4 (C=O), 147.4 ($\underline{C}_{thiophen}$), 138.9 ($\underline{C}_{thiophen}$), 133.2 ($\underline{C}_{phenyl}$), 129.4 ($\underline{C}$H$_{thiophen}$), 129.3 (2×C, $\underline{C}$H$_{phenyl}$), 128.6 ($\underline{C}$H$_{phenyl}$), 125.7 (2×C, $\underline{C}$H$_{phenyl}$), 124.4 ($\underline{C}$H$_{thiophen}$), 78.5 (C-2), 74.5 (C-3), 73.8 (C-5), 71.6 (C-4), 68.7 (C-1), 41.5 ($\underline{C}$H$_2$), 17.2 ($\underline{C}$H$_3$). HR-MS calcd. C$_{18}$H$_{22}$NO$_5$S$^+$: 364.1213; found: 364.1207.

1.6.5 2-Benzo[b]furan amide, N-((β-L-fucopyranosyl methyl) (SH5)

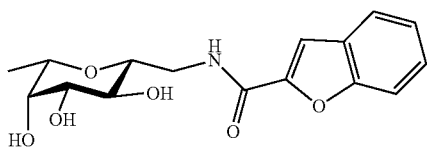

2-Benzo[b]furan amide, N-((β-L-fucopyranosyl methyl) (SH5) (32 mg, 0.10 mmol, 58%) was obtained from benzo[b]furan-2-carbonylchloride as colorless solid. $^1$H NMR (400 MHz, Methanol-d$_4$) δ 7.74-7.71 (m, 1H, C$\underline{H}_{benzofuran}$), 7.61-7.59 (m, 1H, C$\underline{H}_{benzofuran}$), 7.50 (d, J=0.80 Hz, olefin-H), 7.48-7.44 (m, 1H, C$\underline{H}_{benzofuran}$), 7.34-7.30 (m, 1H, C$\underline{H}_{benzofuran}$), 3.83-3.79 (m, 1H, C$\underline{H}_2$NH), 3.67-3.61 (m, 3H, C$\underline{H}_2$NH, H-4, H-5), 3.50-3.48 (m, 2H, H-1, H-3), 3.37-3.33 (m, 1H, H-2), 1.28 (d, J=6.31 Hz, 3H, C$\underline{H}_3$). $^{13}$C NMR (101 MHz, Methanol-d$_4$) δ 161.7 (C=O), 156.6 (C$_{benzofuran}$), 150.0 (C$_{benzofuran}$), 129.0 (C$_{benzofuran}$), 128.4 ($\underline{C}$H$_{benzofuran}$), 125.0 ($\underline{C}$H$_{benzofuran}$), 123.9 ($\underline{C}$H$_{benzofuran}$), 113.0 ($\underline{C}$H$_{benzofuran}$), 111.6 (olefin-$\underline{C}$H), 80.0 (C-2), 76.4 (C-3), 76.0 (C-5), 73.8 (C-4), 70.3 (C-1), 42.2 ($\underline{C}$H$_2$) 17.3 ($\underline{C}$H$_3$). HR-MS calcd. C$_{16}$H$_{20}$NO$_6$$^+$: 322.1285; found: 322.1300.

1.6.6 cinnamide, N-((β-L-fucopyranosyl methyl) (DH74)

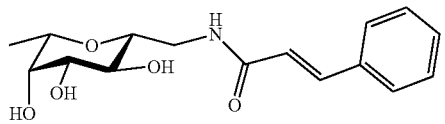

cinnamide, N-((β-L-fucopyranosyl methyl) (DH74) (48.8 mg, 0.16 mmol, 33%) was obtained from cinnamic acid and EDC*HCl as colorless solid. $^1$H NMR (400 MHz, Methanol-d$_4$) 7.60-7.50 (m, 3H, 2×ArH, olefin-H), 7.42-7.32 (m, 3H, ArH), 6.69 (d, J=15.8 Hz, 1H, olefin-H), 3.70-3.59 (m, 4H, H-4, H-5, CH$_2$), 3.50-3.44 (m, 2H, H-3, -4), 3.30-3.24 (m, 1H, H-2), 1.26 (d, J=6.4 Hz, 3H, CH$_3$). $^{13}$C NMR (101 MHz, Methanol-d$_4$) 169.1 (C=O), 141.8 (olefin-CH), 136.3 (ArC), 130.8 (ArCH), 129.9 (2C, ArCH), 128.8 (2×C, ArCH), 121.7 (olefin-CH), 79.8 (C-2), 76.2 (C-3 or -4), 75.7 (C-6), 73.6 (C-5), 69.5 (C-3 or -4), 41.9 (CH$_2$), 17.2 (CH$_3$). HRMS-MS calcd. C$_{16}$H$_{22}$NO$_5$$^+$: 308.14925; found: 308.14885.

1.6.7 3,4-Dimethoxycinnamide, N-((β-L-fucopyranosyl methyl) (DH255a)

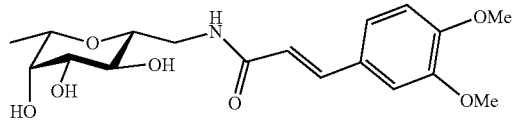

3,4-Dimethoxycinnamide, N-((β-L-fucopyranosyl methyl) (DH255a) (10 mg, 0.03 mmol, 10%) was obtained from 3,4-dimethoxycinnamic acid and EDC*HCl as colorless solid. $^1$H NMR (400 MHz, Methanol-d$_4$) δ 7.48 (d, J=15.7 Hz, 1H, olefin-H), 7.17 (d, J=2.0 Hz, 1H, ArH), 7.15-7.10 (m, 1H, ArH), 6.97 (d, J=8.3 Hz, 1H, ArH), 6.56 (d, J=15.7 Hz, 1H, olefin-H), 3.87 (s, 3H, OC$\underline{H}_3$), 3.86 (s, 3H, OC$\underline{H}_3$), 3.67-3.65 (m, 1H, H-4), 3.69-3.58 (m, 3H, H-5, C$\underline{H}_2$NH), 3.51-3.43 (m, 2H, H-2, H-3), 3.30-3.25 (m, 1H, H-1), 1.26 (d, J=6.4 Hz, 3H, C$\underline{H}_3$). $^{13}$C NMR (101 MHz, Methanol-d$_4$) δ 169.5 (C=O), 152.3 (ArC), 150.7 (ArC), 141.8 (olefin-CH), 129.4 (ArC), 123.3 (ArCH), 119.5 (olefin-CH), 112.7 (ArCH), 111.2 (ArCH), 79.9 (C-1), 76.2 (C-2 or -3), 75.7 (C-5), 73.6 (C-4), 69.5 (C-2 or -3), 56.4 (OC$\underline{H}_3$), 56.4 (OC$\underline{H}_3$), 41.9 ($\underline{C}$H$_2$NH), 17.2 ($\underline{C}$H$_3$). HRMS-MS calcd. C$_{18}$H$_{26}$NO$_7$$^+$: 368.1740; found: 368.1707.

1.7 Synthesis of 1-deoxy-4(R)—C-(ethylacetamide) L-fucose and 1-deoxy-4(R)—C-(ethyl methylsulfonamide) L-Fucose

1.7.1 1-deoxy-2,3-di-O-benzyl-4(R)—C-(ethylamine) L-fucose (RS405)

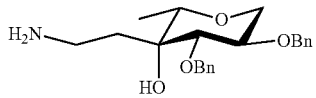

1-deoxy-2,3-di-O-benzyl-4(R)—C-(acetonitrile) L-fucose (RS404) (238 mg, 0.647 mmol) in dry $Et_2O$ (4 mL) was added to a suspension of $LiAlH_4$ (110 mg, 2.9 mmol) in dry $Et_2O$ (8 mL) and stirred for 30 min. The reaction mixture was quenched with sat. $NaHCO_3$ solution (20 mL) and the aqueous layer was extracted with EtOAc (5×40 mL). The combined organic layers were dried over $Na_2SO_4$ and the solvent was removed in vacuo. The crude colourless oil (240 mg) was used without further purification. $^1$H NMR (500 MHz, Chloroform-d) δ 7.48-7.26 (m, 10H, C$\underline{H}_{benzyl}$), 5.07 (d, J=11.5 Hz, 1H, C$\underline{H}_{2\ benzyl}$), 4.80-4.55 (m, 3H, C$\underline{H}_{2\ benzyl}$), 4.08-3.94 (m, 2H, H-1$_{equatorial}$, H-2), 3.32 (d, J=8.7 Hz, 1H, H-3), 3.22 (q, J=6.3 Hz, 1H, H-5), 3.15 (t, J=10.5 Hz, 1H, H-1$_{axial}$), 2.62 (ddd, J=7.9, 6.7, 2.3 Hz, 2H), 1.68 (ddd, J=14.3, 8.0, 6.5 Hz, 1H, C$\underline{H}_2$CH$_2$NH), 1.49 (m, 1H, ddd, J=14.1, 14.1, 7.4 Hz, 1H, C$\underline{H}_2$CH$_2$NH), 1.22 (d, J=6.3 Hz, 3H, H-6). ESI-MS: calcd. $C_{22}H_{30}NO_4^+$: 372.2; found: 371.8.

1.7.2 1-deoxy-2,3-di-O-benzyl-4(R)—C-(ethylacetamide) L-fucose (RS407)

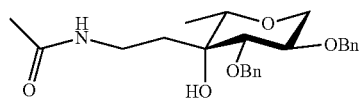

1-deoxy-2,3-di-O-benzyl-4(R)—C-(ethylamine) L-fucose (RS405) (65.9 mg, 0.177 mmol) and triethylamine (37 µL, 0.266 mmol) were dissolved in dry DMF (2 mL) and cooled to 0° C. Acetylchloride (15 µL, 0.212 mmol) was added under nitrogen. The reaction was allowed to warm to r.t. and was stirred for further 4 h. Saturated aqueous $NH_4Cl$ (3 mL) was added, and extracted with EtOAc (3×10 mL). The combined organic layers were dried over $Na_2SO_4$, filtered and concentrated in vacuo. The residue was purified by HPLC (VP250/10 Nucleodur C-18 Gravity SB, 5 µm from Macherey Nagel, 9 mL/min, Eluent A: $H_2O$, Eluent B: MeCN, 0-5 min 25% B, 5-40 min 25%-85% B). 1-deoxy-2,3-di-O-benzyl-4(R)—C-(ethylacetamide) L-fucose (36.6 mg, 0.088 mmol, 50%) was observed as colorless solid. $^1$H NMR (500 MHz, Methanol-d$_4$) δ 7.45-7.21 (m, 10H, C$\underline{H}_{benzyl}$), 4.99 (d, J=10.9 Hz, 1H, C$\underline{H}_{2\ benzyl}$), 4.80 (d, J=11.0 Hz, 1H, C$\underline{H}_{2\ benzyl}$), 4.64 (s, 2H, C$\underline{H}_{2\ benzyl}$), 4.00 (dd, J=10.8, 5.4 Hz, 1H H-1$_{equatorial}$), 3.94 (ddd, J=10.4, 8.9, 5.4 Hz, 1H, H-2), 3.43 (d, J=9.0 Hz, 1H, H-3), 3.39 (q, J=6.3 Hz, 1H, H-5), 3.16 (t, J=10.8 Hz, 1H, H-1$_{axial}$), 3.13-3.01 (m, 2H, CH$_2$C$\underline{H}_2$NH), 2.05 (ddd, J=13.7, 10.2, 6.0 Hz, 1H, C$\underline{H}_2$CH$_2$NH), 1.89 (s, 3H, COCH$_3$), 1.57 (ddd, J=13.7, 10.2, 6.7 Hz, 1H, C$\underline{H}_2$CH$_2$NH), 1.18 (d, J=6.3 Hz, 3H, H-6). $^{13}$C NMR (126 MHz, Methanol-d$_4$) δ 172.9 (CO), 140.1 (C$_{benzyl}$), 139.9 (C$_{benzyl}$), 129.4 (CH$_{benzyl}$), 129.3 (CH$_{benzyl}$), 129.3 (C$\underline{H}_{benzyl}$), 129.0 (C$\underline{H}_{benzyl}$), 128.7 (C$\underline{H}_{benzyl}$), 128.6 (C$\underline{H}_{benzyl}$), 83.4 (C-3), 78.4 (C-2), 78.1 (C-5), 76.4 (C$\underline{H}_{2\ benzyl}$), 76.0 (C-4), 73.8 (C$\underline{H}_{2\ benzyl}$), 69.0 (C-1), 35.8 (C$\underline{H}_2$CH$_2$NH), 35.1 (C$\underline{H}_2$CH$_2$NH), 22.5 (COC$\underline{H}_3$), 14.1 (C-6). HR-MS calcd. $C_{24}H_{32}NO_5^+$: 414.2275; found: 414.2284.

1.7.3 1-deoxy-4(R)—C-(ethylacetamide) L-fucose (RS411)

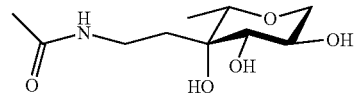

Purification of the reaction mixture yielded 1-deoxy-4(R)—C-(ethylacetamide) L-fucose (RS411) (20.6 mg, 0.09 mmol, 99%) as colorless oil. $^1$H NMR (500 MHz, Methanol-d$_4$) δ 3.85 (dd, J=10.9, 5.6 Hz, 1H, H-1$_{equatorial}$), 3.75 (ddd, J=10.6, 9.1, 5.6 Hz, 1H, H-2), 3.41 (q, J=6.4 Hz, 1H, H-5), 3.28 (d, J=9.1 Hz, 1H, H-3), 3.23-3.17 (m, 2H, CH$_2$C$\underline{H}_2$NH), 3.11 (t, J=10.8 Hz, 1H, H-1$_{axial}$), 1.98 (ddd, J=13.7, 9.1, 7.0 Hz, 1H, C$\underline{H}_2$CH$_2$NH), 1.92 (s, 3H, NHAc), 1.59 (ddd, J=13.7, 9.0, 7.3 Hz, 1H, C$\underline{H}_2$CH$_2$NH), 1.20 (d, J=6.3 Hz, 3H, H-6). $^{13}$C NMR (126 MHz, Methanol-d$_4$) δ 173.1 NH$\underline{C}$O), 78.2 (C-5), 77.0 (C-3), 75.5 (C-4), 71.1 (C-1), 69.4 (C-2), 35.9 (CH$_2$C$\underline{H}_2$NH), 35.0 (C$\underline{H}_2$CH$_2$NH), 22.6 (NHAc), 14.3 (C-6). HR-MS calcd. $C_{10}H_{20}NO_5^+$: 234.1336.1945; found: 234.1339.

1.7.4 1-deoxy-2,3-di-O-benzyl-4(R)—C-(ethyl methylsulfonamide) L-fucose (RS408)

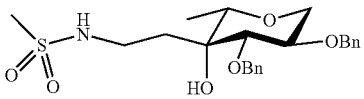

1-deoxy-2,3-di-O-benzyl-4(R)—C-(ethylamine) L-fucose (RS405) (55 mg, 0.148 mmol) and triethylamine (30 µL 0.220 mmol) were dissolved in dry DMF (2 mL) and cooled to 0° C. Methylsulfonchloride (14 µL 0.177 mmol) was added under nitrogen. The reaction was allowed to warm to r.t. and was stirred for further 4 h. Saturated aqueous $NH_4Cl$ (3 mL) was added, and extracted with EtOAc (3×10 mL). The combined organic layers were dried over $Na_2SO_4$, filtered and concentrated in vacuo. The residue was purified by HPLC (VP250/10 Nucleodur C-18 Gravity SB, 5 µm from Macherey Nagel, 9 mL/min, Eluent A: $H_2O$, Eluent B: MeCN, 0-5 min 25% B, 5-40 min 25%-85% B). 1-deoxy-2,3-di-O-benzyl-4(R)—C-(ethyl methylsulfonamide) L-fucose (31.7 mg, 0.07 mmol, 48%) was observed as colorless solid. $^1$H NMR (500 MHz, Methanol-d$_4$) δ 7.46-7.22 (m, 10H, C$\underline{H}_{benzyl}$), 5.01 (d, J=11.0 Hz, 1H, C$\underline{H}_{2\ benzyl}$), 4.77 (d, J=11.1 Hz, 1H, C$\underline{H}_{2\ benzyl}$), 4.64 (s, 2H, C$\underline{H}_{2\ benzyl}$), 4.00 (dd, J=10.8, 5.4 Hz, 1H, H-1$_{equatorial}$), 3.94 (ddd, J=10.4, 8.8, 5.4 Hz, 1H, H-2), 3.49-3.40 (m, 2H, H-3, H-5), 3.17 (t, J=10.6 Hz, 1H, H-1$_{axial}$), 3.00 (ddd, J=9.3, 6.3, 3.9 Hz, 2H, CH$_2$C$\underline{H}_2$NH), 2.84 (s, 3H, SO$_2$CH$_3$), 2.11 (ddd, J=13.8, 9.4, 6.2 Hz, 1H, C$\underline{H}_2$CH$_2$NH), 1.65 (ddd, J=13.8, 9.7, 6.9 Hz, 1H, CH$_2$C$\underline{H}_2$NH), 1.18 (d, J=6.3 Hz, 3H, H-6). $^{13}$C NMR (126 MHz, Methanol-d$_4$) δ 140.1 (C$_{benzyl}$), 139.9 (C$_{benzyl}$), 129.4 (CH$_{benzyl}$), 129.3 (CH$_{benzyl}$), 129.0 (CH$_{benzyl}$), 128.7 ( CH$_{benzyl}$), 128.7 (CH$_{benzyl}$), 83.5 (C-3), 78.5 (C-2), 78.1 (C-5), 76.3 (C-4), 76.0 (CH$_{2\ benzyl}$), 73.8 (CH$_{2\ benzyl}$), 68.9 (C-1), 39.7 (SO$_2$CH$_3$), 39.5 (CH$_2$CH$_2$NH), 36.2 (CH$_2$CH$_2$NH), 14.2 (C-6). HR-MS calcd. C$_{23}$H$_{32}$NO$_6$S$^+$: 450.1945; found: 450.1916.

1.7.5 1-deoxy-4(R)—C-(ethyl methylsulfonamide) L-fucose (RS412)

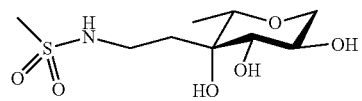

Purification of the reaction mixture yielded 1-deoxy-4 (R)—C-(ethyl methylsulfonamide) L-fucose (RS412) (16.5 mg, 0.06 mmol, 95%) as colorless oil. $^1$H NMR (500 MHz, Methanol-d$_4$) δ 3.85 (dd, J=10.9, 5.6 Hz, 1H, H-1$_{equatorial}$), 3.74 (ddd, J=10.6, 9.0, 5.6 Hz, 1H, H-2), 3.44 (q, J=6.4 Hz, 1H, H-5), 3.29 (d, J=9.1 Hz, 1H, H-3), 3.16-3.08 (m, 3H, H-1$_{axial}$, CH$_2$CH$_2$NH), 2.94 (s, 3H, SO$_2$CH$_3$), 2.04 (ddd, J=13.7, 8.5, 6.8 Hz, 1H, CH$_2$CH$_2$NH), 1.66 (ddd, J=13.9, 8.8, 7.3 Hz, 1H, CH$_2$CH$_2$NH), 1.19 (d, J=6.4 Hz, 3H, H-6). $^{13}$C NMR (126 MHz, Methanol-d$_4$) δ 78.4 (C-5), 77.3 (C-3), 75.5 (C-4), 71.1 (C-1), 69.4 (C-2), 39.7 (CH$_2$CH$_2$NH), 39.6 (SO$_2$CH$_3$), 36.0 (CH$_2$CH$_2$NH), 14.3 (C-6). HR-MS calcd. C$_9$H$_{20}$NO$_6^+$: 270.1006; found: 270.1004.

2. Expression and Purification of LecB$_{PAO1}$ and LecB$_{PA14}$

2.1 Bacterial Strains and Growth Conditions

E. coli XL1-blue strain was used for amplification of plasmid pRS01.4 carrying the sequence of LecB$_{PA14}$, that was transformed into E. coli BL21(DE3). Lysogeny broth (LB) media supplemented with ampicillin (100 μg/mL) was used for growing.

2.2 Molecular Cloning and Expression of LecB$_{PA14}$ as Well as Expression and Purification of LecB$_{PAO1}$ Genomic DNA from P. aeruginosa UCBPP-PA14 was isolated using Gen Elute Bacterial Genomic DNA Kit (Sigma Aldrich). PCR amplification was performed by using Phusion polymerase (NEB New England Biolabs) and primers introducing NdeI (5'-GGAATTCCATATG-GCAACAAGGAGTG-3'; SEQ ID NO: 1) and HindIII (5'-CCCAAGCTTCTAGCCGAGCGGCCAG-3'; SEQ ID NO: 2) restriction sites. After digestion with NdeI and HindIII restriction enzymes (NEB New England Biolabs) the DNA fragment was ligated into the multiple cloning site of digested (NdeI and HindIII restriction enzymes (NEB New England Biolabs)) pET22b(+) (Novagen) using T4 DNA ligase (MO202) (NEB New England Biolabs) which resulted in plasmid pRS01.4. The correct sequence was confirmed by sequencing (GATC biotech) with Primer T7 promoter (5'-TAATACGACTCACTATATAGG-3'; SEQ ID NO: 3) and T7 terminator (5'-GCTAGTTATTGCTCA-GCGG-3'; SEQ ID NO: 4). Expression and purification of the protein was performed in analogy to LecB$_{PO1A}$ described by Mitchell et al. (E. P. Mitchell, C. Sabin, L. Snajdrova, M. Pokorna, S. Perret, C. Gautier, C. Hofr, N. Gilboa-Garber, J. Koca, M. Wimmerova, A. Imberty, Proteins 2005, 58, 735- 746) and dialyzed against TBS/Ca (20 mM Tris, 137 mM NaCl, 2.6 mM KCl at pH 7.4 supplemented with 1 M CaCl$_2$).

3. Competitive Binding Assay

The competitive binding assay based on fluorescence polarization was performed as described previously described by Hauck et al. (D. Hauck, I. Joachim, B. Frommeyer, A. Varrot, B. Philipp, H. M. Moller, A. Imberty, T. E. Exner, A. Titz, ACS Chem Biol 2013, 8, 1775-1784). Briefly, 20 μL of a stock solution of LecB$_{PA14}$ or LecB$_{PAO1}$ (150 nM) and fluorescent reporter ligand N-(fluorescein-5-yl)-N'-(α-L-fucopyranosyl ethylen)-thiocarbamide (15 nM) in TBS/Ca (20 mM Tris, 137 mM NaCl, 2.6 mM KCl at pH 7.4 supplemented with 1 M CaCl$_2$) were mixed with 10 μL serial dilutions (1 mM to 12.8 nM) of testing compounds in TBS/Ca in triplicates. After addition of the reagents, the black 384-well microtiter plates (Greiner Bio-One, Germany, cat. no. 781900) were incubated for 8-22 h at r.t. in a humidity chamber. Fluorescence emission parallel and perpendicular to the excitation plane was measured on a PheraStar FS (BMG Labtech, Germany) plate reader with excitation filters at 485 nm and emission filters at 535 nm. The measured intensities were reduced by buffer values and fluorescence polarization was calculated. The data were analyzed using BMG Labtech MARS software and/or with Graphpad Prism and fitted according to the four parameter variable slope model. Bottom and top plateaus were defined by the standard compounds L-fucose and methyl α-D-mannoside respectively and the data was reanalyzed with these values fixed. A minimum of three independent measurements of triplicates each was performed for every ligand.

Results are shown in Tables 1, 2, 3 and 4.

TABLE 1

Competitive binding of different C-3 derivatives to two LecB variants (IC$_{50}$ values)

| structure | IC$_{50}$ [μM] LecB$_{PAO1}$ | IC$_{50}$ [μM] LecB$_{PA14}$ |
|---|---|---|
| 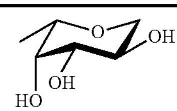 | 1.55 ± 0.50 | 0.60 ± 0.14 |
| 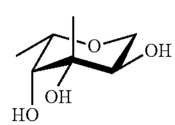 | 49.6 ± 7.80 | 6.54 ± 1.34 |
| 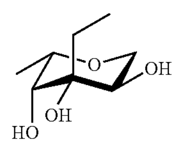 | 471 ± 104 | 41.5 ± 9.94 |
| 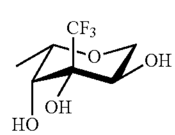 | >600 | >300 |

TABLE 1-continued

Competitive binding of different C-3 derivatives to two LecB variants (IC$_{50}$ values)

| structure | IC$_{50}$ [µM] LecB$_{PA01}$ | IC$_{50}$ [µM] LecB$_{PA14}$ |
|---|---|---|
| (structure with NH$_2$) | >600 | >300 |
| (isobutyramide structure) | 348 ± 65.0 | 62.6 ± 12.4 |
| (isopropylsulfonamide structure) | >600 | 286 ± 77 |

TABLE 2

Competitive binding of different C-4 derivatives to two LecB variants (IC$_{50}$ values)

| structure | IC$_{50}$ [µM] LecB$_{PA01}$ | IC$_{50}$ [µM] LecB$_{PA14}$ |
|---|---|---|
| (methyl C-4 derivative) | 0.46 ± 0.07 | 0.17 ± 0.03 |
| (ethyl C-4 derivative) | 0.39 ± 0.06 | 0.14 ± 0.03 |
| (propyl C-4 derivative) | 0.66 ± 0.09 | 0.23 ± 0.05 |
| (butyl C-4 derivative) | 0.65 ± 0.01 | 0.23 ± 0.03 |
| (hexyl C-4 derivative) | 0.61 ± 0.09 | 0.33 ± 0.16 |

TABLE 2-continued

Competitive binding of different C-4 derivatives to two LecB variants (IC$_{50}$ values)

| structure | IC$_{50}$ [µM] LecB$_{PA01}$ | IC$_{50}$ [µM] LecB$_{PA14}$ |
|---|---|---|
| (phenyl C-4 derivative) | 4.97 ± 0.36 | 1.48 ± 0.08 |
| (benzyl C-4 derivative) | 2.61 ± 0.02 | 0.62 ± 0.08 |
| (cyclohexyl C-4 derivative) | 2.59 ± 0.09 | 0.75 ± 0.13 |
| (isobutyl C-4 derivative) | 0.78 ± 0.09 | 0.45 ± 0.12 |
| (cyanomethyl C-4 derivative) | 1.69 ± 0.15 | 0.58 ± 0.11 |
| (acetamidoethyl C-4 derivative) | 0.52 ± 0.03 | 0.18 ± 0.02 |
| (methanesulfonamidoethyl C-4 derivative) | 0.44 ± 0.07 | 0.15 ± 0.02 |

TABLE 3

Competitive binding of different C-1 derivatives to two LecB variants (IC$_{50}$ values), first part

| structure | IC$_{50}$ [µM] LecB$_{PA01}$ | IC$_{50}$ [µM] LecB$_{PA14}$ |
|---|---|---|
| (mesitylsulfonamide C-1 derivative) | 0.98 ± 0.06 | 0.42 ± 0.20 |
| (thiophene-2-sulfonamide C-1 derivative) | 1.80 ± 0.15 | 0.44 ± 0.04 |
| (thiophene-3-sulfonamide C-1 derivative) | 1.85 ± 0.13 | 0.64 ± 0.27 |

TABLE 3-continued

Competitive binding of different C-1 derivatives to two LecB variants (IC$_{50}$ values), first part

| structure | IC$_{50}$ [μM] LecB$_{PA01}$ | IC$_{50}$ [μM] LecB$_{PA14}$ |
|---|---|---|
| (fucose-CH$_2$-NHSO$_2$-5-methylthiophen-2-yl) | 3.49 ± 0.21 | 0.65 ± 0.35 |
| (fucose-CH$_2$-NHSO$_2$-2,5-dimethylthiophen-3-yl) | 1.82 ± 0.19 | 0.36 ± 0.18 |
| (fucose-CH$_2$-NHSO$_2$-5-bromothiophen-2-yl) | 3.20 ± 0.37 | 0.62 ± 0.39 |
| (fucose-CH$_2$-NHSO$_2$-4,5-dichlorothiophen-2-yl) | 4.57 ± 0.59 | 1.04 ± 0.78 |
| (fucose-CH$_2$-NHSO$_2$-5-methylisoxazol-4-yl) | 2.06 ± 0.20 | 0.38 ± 0.05 |
| (fucose-CH$_2$-NHSO$_2$-1,3-dimethylpyrazol-4-yl) | 2.42 ± 0.14 | 0.68 ± 0.07 |

TABLE 4

Competitive binding of different C-1 derivatives to two LecB variants (IC$_{50}$ values), second part

| structure | IC$_{50}$ [μM] LecB$_{PA01}$ | IC$_{50}$ [μM] LecB$_{PA14}$ |
|---|---|---|
| (fucose-CH$_2$-NHSO$_2$-furan-2-yl) | 3.48 ± 0.75 | 0.48 ± 0.01 |
| (fucose-CH$_2$-NHSO$_2$-2,5-dimethylfuran-3-yl) | 3.10 ± 0.33 | 0.33 ± 0.05 |
| (fucose-CH$_2$-NHSO$_2$-5-trifluoromethylfuran-2-yl) | 3.88 ± 0.70 | 0.49 ± 0.11 |
| (fucose-CH$_2$-NHSO$_2$-1-methylimidazol-5-yl) | 14.2 ± 3.57 | 1.86 ± 0.23 |
| (fucose-CH$_2$-NHSO$_2$-1-methylpyrazol-3-yl) | 6.79 ± 1.81 | 0.70 ± 0.03 |
| (fucose-CH$_2$-NHSO$_2$-1-methylpyrazol-4-yl) | 5.88 ± 0.26 | 0.96 ± 0.06 |
| (fucose-CH$_2$-NHSO$_2$-4-methylthiophen-2-yl) | 2.51 ± 0.54 | 0.31 ± 0.04 |
| (fucose-CH$_2$-NHSO$_2$-5-ethylthiophen-2-yl) | 4.22 ± 1.13 | 0.44 ± 0.04 |
| (fucose-CH$_2$-NHCO-phenyl) | 8.73 ± 0.60 | 3.54 ± 0.24 |
| (fucose-CH$_2$-NHCO-CH=CH-phenyl) | 4.21 ± 0.94 | 2.49 ± 0.20 |
| (fucose-CH$_2$-NHCO-benzothiophen-2-yl) | 4.27 ± 0.16 | 2.34 ± 0.03 |
| (fucose-CH$_2$-NHCO-benzofuran-2-yl) | 10.2 ± 0.86 | 2.56 ± 0.33 |
| (fucose-CH$_2$-NHCO-2-phenylthiazol-4-yl) | 12.3 ± 0.34 | 2.81 ± 0.21 |

4. Microcalorimetric Assay

The binding of 1-deoxy fucose, 4-C substituted 1-deoxy fucoses and 1-C substituted 1-deoxy fucoses to two lectins was determined in a microcalorimetric assay:

The concentration of the monomer of LecB (dissolved in TBS/Ca (20 mM Tris, 137 mM NaCl, 2.6 mM KCl at pH 7.3 supplemented with 1 M $CaCl_2$)) was determined by UV spectroscopy at 280 nm using a molar extinction coefficient of 6990 $M^{-1}$ $cm^{-1}$ for both LecB variants (see: M. R. Wilkins, E. Gasteiger, A. Bairoch, J. C. Sanchez, K. L. Williams, R. D. Appel, D. F. Hochstrasser, *Methods Mol Biol* 1999, 112, 531-552). The temperature of the sample cell was 25° C. The titration was performed with a solution of ligands in the same buffer. ITC was performed on a Microcal ITC200 (General Electric) and the data was analyzed according to the one site binding model using the Microcal Origin software. A minimum of three independent titrations was performed for each ligand, if not indicated otherwise.

Results are shown in Tables 5 and 6.

TABLE 5

Microcalorimetric Assay for Direct Binding of C-4 derivatives to two LecB variants

|  | $LecB_{PAO1}$ | $LecB_{PA14}$ |
|---|---|---|
| $K_d$ [nM] | 773 ± 110 | 453 ± 120 |
| ΔG [kJ/mol] | −34.9 ± 0.35 | −36.3 ± 0.64 |
| ΔH [kJ/mol] | −36.3 ± 0.91 | −31.7 ± 1.09 |
| −TΔS [kJ/mol] | 1.37 ± 1.14 | −4.61 ± 1.67 |
| N | 1.07 ± 0.03 | 0.94 ± 0.04 |

|  | $LecB_{PAO1}$ | $LecB_{PA14}$ |
|---|---|---|
| $K_d$ [nM] | 201 ± 42 | 130 ± 49 |
| ΔG [kJ/mol] | −38.2 ± 0.54 | −39.4 ± 0.87 |
| ΔH [kJ/mol] | −51.7 ± 4.54 | −42.0 ± 1.16 |
| −TΔS [kJ/mol] | 13.4 ± 4.69 | 2.59 ± 1.10 |
| N | 1.03 ± 0.13 | 0.96 ± 0.04 |

|  | $LecB_{PAO1}$ | $LecB_{PA14}$ |
|---|---|---|
| $K_d$ [nM] | 401 ± 84 | 246 ± 47 |
| ΔG [kJ/mol] | −36.6 ± 0.40 | −37.7 ± 0.48 |
| ΔH [kJ/mol] | −47.1 ± 0.50 | −39.4 ± 0.04 |
| −TΔS [kJ/mol] | 10.5 ± 0.78 | 1.65 ± 0.49 |
| N | 1.02 ± 0.09 | 1.03 ± 0.08 |

TABLE 6

Microcalorimetric Assay for Direct Binding of C-1 derivatives to two LecB variants

|  | $LecB_{PAO1}$ | $LecB_{PA14}$ |
|---|---|---|
| $K_d$ [μM] | 3.09 ± 0.84 | 2.59 ± 0.39 |
| ΔG [kJ/mol] | −31.5 ± 0.69 | −30.5 ± 2.19 |
| ΔH [kJ/mol] | −32.9 ± 1.65 | −31.4 ± 1.44 |
| −TΔS [kJ/mol] | 1.37 ± 1.34 | 0.88 ± 1.0 |
| N | 0.93 ± 0.01 | 1.07 ± 0.05 |

|  | $LecB_{PAO1}$ | $LecB_{PA14}$ |
|---|---|---|
| $K_d$ [μM] | 1.27 ± 0.12 | 0.31 ± 0.05 |
| ΔG [kJ/mol] | −33.6 ± 0.24 | −37.1 ± 0.44 |
| ΔH [kJ/mol] | −35.2 ± 0.04 | −37.8 ± 3.68 |
| −TΔS [kJ/mol] | 1.52 ± 0.21 | 0.65 ± 3.24 |
| N | 0.99 ± 0.04 | 0.98 ± 0.05 |

|  | $LecB_{PAO1}$ | $LecB_{PA14}$ |
|---|---|---|
| $K_d$ [μM] | 0.83 ± 0.10 | 0.29 ± 0.03 |
| ΔG [kJ/mol] | −34.7 ± 0.26 | −37.3 ± 0.29 |
| ΔH [kJ/mol] | −48.1 ± 0.40 | −50.0 ± 2.58 |
| −TΔS [kJ/mol] | 13.4 ± 0.14 | 12.7 ± 2.70 |
| N | 0.92 ± 0.05 | 0.87 ± 0.08 |

|  | $LecB_{PAO1}$ | $LecB_{PA14}$ |
|---|---|---|
| $K_d$ [μM] | 1.20 ± 0.18 | 0.32 ± 0.07 |
| ΔG [kJ/mol] | −33.8 ± 0.34 | −37.2 ± 0.60 |
| ΔH [kJ/mol] | −47.3 ± 1.20 | −40.4 ± 1.11 |
| −TΔS [kJ/mol] | 13.5 ± 1.38 | 3.29 ± 1.68 |
| N | 0.98 ± 0.03 | 0.98 ± 0.06 |

The invention claimed is:

1. A compound of the general formula (I):

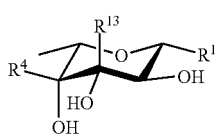

(I)

wherein
$R^4$ is selected from the group consisting of
(a) hydrogen;
(b) a $C_1$-$C_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(c) a $C_3$ to $C_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with R$^{13}$ being a C$_1$-C$_4$ alkyl group, and —SO$_3$H, and a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, (d) an aryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(f) a heteroaryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

R$^1$ is selected from the group consisting of hydrogen,

—(CH$_2$)$_n$—NR$^2$—X—R$^3$, wherein n is 1, 2 or 3;
—(CH$_2$)$_n$—NH$_2$, wherein n is 2 or 3; and
—(CH$_2$)$_n$—O—R$^5$, wherein R$^5$ is a hydrogen atom and n is 2 or 3, or R$^5$ is a C$_1$-C$_4$ alkyl group and n is 1, 2 or 3;

wherein
R$^2$ is hydrogen or a C$_1$ to C$_3$ alkyl group;
X is SO$_2$ or CO;
R$^3$ is selected from the group consisting of:

(i) an aralkyl group, the alkyl moiety having 1 to 6 carbon atoms, and the aryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl moiety may be connected to form a methylenedioxy group or an ethylenedioxy group;

(ii) an aralkenyl group, the alkenyl moiety having 2 to 6 carbon atoms, and the aryl moiety being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl moiety may be connected to form a methylenedioxy group or an ethylenedioxy group;

(iii) an aryl group, optionally being substituted by one or more substituents selected from the group consisting of a halogen atom, —NH$_2$, —NO$_2$, —CN, —OH, a C$_1$-C$_4$ alkoxy group and —COOR$^5$, wherein R$^5$ is a hydrogen atom or a C$_1$-C$_4$ alkyl group, and wherein two adjacent substituents of the aryl group may be connected to form a methylenedioxy group or an ethylenedioxy group;

(iv) a heteroaryl group, optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the heteroaryl group may be connected to form a methylenedioxy group or an ethylenedioxy group;

(v) a heteroaralkyl group, the alkyl moiety having 1 to 6 carbon atoms and the heteroaryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group; and (vi) a heteroaralkenyl group, the alkenyl moiety having 2 to 6 carbon atoms, and the heteroaryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$ wherein R$^5$ is a hydrogen atom or a C$_1$-C$_4$ alkyl group;

and

R$^{13}$ is selected from the group consisting of
(a) hydrogen;
(b) a C$_1$-C$_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;

wherein R$^{12}$ is a C$_1$-C$_4$ alkyl group; and
wherein R$^{11}$ is selected from the group consisting of
hydrogen,
a C$_1$-C$_4$ alkyl group,
an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and
a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;

(c) a C$_3$ to C$_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;

wherein R$^{12}$ is a C$_1$-C$_4$ alkyl group; and
wherein R$^{11}$ is selected from the group consisting of
hydrogen,
a C$_1$-C$_4$ alkyl group,
an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and
a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, (d) an aryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(f) a heteroaryl group, optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

with the proviso that at least one of R$^4$ or R$^{13}$ is not hydrogen;
or a salt thereof or a solvate thereof.

2. The compound according to claim 1, wherein the compound has a structure according to general formula (II), general formula (III), or general formula (IV):

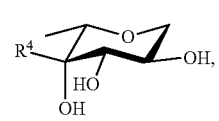

(II)

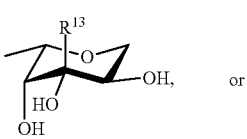

(III)

or

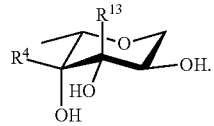

(IV)

3. The compound according to claim 1, wherein $R^4$ is selected from the group consisting of
(b) a $C_1$-$C_6$ alkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(c) a $C_3$ to $C_7$ cycloalkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
wherein $R^{12}$ is a $C_1$-$C_4$ alkyl group; and
wherein $R^{11}$ is selected from the group consisting of
hydrogen,
a $C_1$-$C_4$ alkyl group,
an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H, and
a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H;
(d) an aryl group, optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(e) an aralkyl group, the alkyl moiety having 1 to 6 carbon atoms, and the aryl moiety optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group;
(f) a heteroaryl group, optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group; and
(g) a heteroaralkyl group, the alkyl moiety having 1 to 6 carbon atoms, and the heteroaryl moiety optionally being substituted by one, two or three substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with $R^{13}$ being a $C_1$-$C_4$ alkyl group, —NR$^{13}$R$^{14}$ with $R^{13}$ and $R^{14}$ each being independently from each other a $C_1$-$C_4$ alkyl group, —NO$_2$, —CN, —COOH, —COOR$^{13}$ with $R^{13}$ being a $C_1$-$C_4$ alkyl group, and —SO$_3$H; and wherein two adjacent substituents of the aryl group may be connected to form a methylenedioxy group or an ethylenedioxy group.

4. The compound according to claim 1,
wherein the aryl moiety or the aryl group of $R^4$ is a phenyl group or a naphthyl group; or
wherein the heteroaryl moiety or the heteroaryl group of $R^4$ is selected from the group consisting of
(i) a five-membered aromatic monocyclic ring, wherein 1, 2, 3, or 4 of the ring atoms are the same or different heteroatoms, said heteroatoms being selected from O, N, or S;
(ii) a six-membered aromatic monocyclic ring, wherein 1, 2, 3, 4, or 5 of the ring atoms are the same or different heteroatoms, said heteroatoms being selected from O, N, or S; and
(iii) an aromatic bicyclic ring system with 8 to 12 members, wherein 1, 2, 3, 4, 5, or 6 of the ring atoms are the same or different heteroatoms, said heteroatoms being selected from O, N, or S.

5. The compound according to claim 1, wherein $R^4$ is selected from the group consisting of methyl, ethyl, propyl, butyl, 2-isopentyl, hexyl, phenyl, benzyl, cyclohexyl, —CH$_2$—CN, —CH$_2$—CH$_2$—NH$_2$, —CH$_2$—CH$_2$—N(CH$_3$)$_2$, —CH$_2$—CH$_2$—NH—CO—CH$_3$, —CH$_2$—CH$_2$—NH—SO$_2$—CH$_3$, and —CH$_2$—CH$_2$—O—CH$_3$.

6. The compound according to claim 1, wherein $R^{13}$ is a $C_1$-$C_6$ alkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, and —NO$_2$;
  wherein R$^{11}$ is selected from the group consisting of hydrogen and a C$_1$-C$_4$ alkyl group, and
  wherein R$^{12}$ is a C$_1$-C$_4$ alkyl group.

7. The compound according to claim 1, wherein R$^1$ is selected from the group consisting of
  hydrogen,
  —(CH$_2$)$_n$—NR$^2$—X—R$^3$, wherein n is 1; and
  —(CH$_2$)$_n$—O—R$^5$, wherein R$^5$ is a C$_1$-C$_4$ alkyl group and n is 1; and/or wherein R$^2$ is a hydrogen atom.

8. The compound according to claim 1, wherein the aryl moiety, the heteroaryl moiety, the aryl group or the heteroaryl group of R$^3$ have one or more substituents selected from the group consisting of a halogen atom, —NH$_2$, —NO$_2$ and a methoxy group, or two adjacent substituents of the aryl moiety or the aryl group are connected to form a methylenedioxy group or an ethylenedioxy group.

9. The compound according to claim 1, wherein the aryl moiety or the aryl group of R$^3$ is a phenyl group or a naphthyl group.

10. The compound according to claim 1, wherein X is SO$_2$ and R$^3$ is an aryl or heteroaryl group, optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl group or the heteroaryl group may be connected to form a methylenedioxy group or an ethylenedioxy group.

11. The compound according to claim 1, wherein X is C=O and R$^3$ is
  an aralkenyl group, the alkenyl moiety having 2 carbon atoms, the aryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the aryl moiety may be connected to form a methylenedioxy group or an ethylenedioxy group, or
  a heteroaralkenyl group, the alkenyl moiety having 2 carbon atoms, the heteroaryl moiety optionally being substituted by one or more substituents selected from the group consisting of a halogen atom, —NH$_2$, —NO$_2$, —CN, —OH, a C$_1$-C$_4$ alkyl group, a C$_1$-C$_4$ alkoxy group and —COOR$^5$, wherein R$^5$ is a hydrogen atom or a C$_1$-C$_4$ alkyl group, and wherein two adjacent substituents of the heteroaryl moiety may be connected to form a methylenedioxy group or an ethylenedioxy group.

12. A pharmaceutical composition comprising the compound according to claim 1, and optionally comprising one or more constituents selected from the group consisting of a pharmaceutically acceptable carrier, a diluent, an excipient and an anti-bacterial therapeutic agent.

13. Method for the prophylaxis or treatment of *Pseudomonas aeruginosa* infections in a patient, comprising the step:
  administering an effective amount of the compound according to claim 1, optionally in combination with one or more anti-bacterial therapeutic agent(s) to a subject in need thereof.

14. Method for the prophylaxis or treatment of *Pseudomonas aeruginosa*-associated respiratory tract infections in a patient suffering from cystic fibrosis, comprising the step:
  administering an effective amount of the compound according to claim 1, optionally in combination with one or more anti-bacterial therapeutic agent(s) to a subject in need thereof.

15. A compound having a structure according to general formula (V) or general formula (VI)

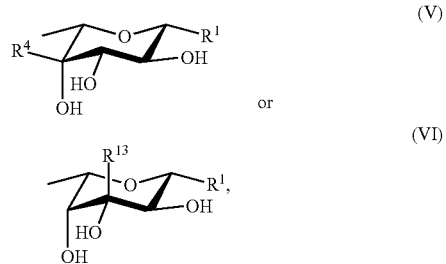

wherein
R$^4$ is selected from the group consisting of
  (b) a C$_1$-C$_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
  wherein R$^{12}$ is a C$_1$-C$_4$ alkyl group; and
  wherein R$^{11}$ is selected from the group consisting of
    hydrogen,
    a C$_1$-C$_4$ alkyl group,
    an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and
    a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;
  (c) a C$_3$ to C$_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
    wherein R$^{12}$ is a C$_1$-C$_4$ alkyl group; and
    wherein R$^{11}$ is selected from the group consisting of
      hydrogen, a $C_1$-$C_4$ alkyl group,
- an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H, and
- a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H, (d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;

(f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;

R$^1$ is selected from the group consisting of hydrogen, —(CH$_2$)$_n$—NR$^2$—X—R$^3$, —(CH$_2$)$_n$—NH$_2$, and —(CH$_2$)$_n$—O—R$^5$, wherein R$^5$ is a hydrogen atom or a $C_1$-$C_4$ alkyl group;

n is 1, 2 or 3;

R$^2$ is hydrogen or a $C_1$ to $C_3$ alkyl group;

X is SO$_2$ or CO;

R$^3$ is selected from the group consisting of:

(i) an aralkyl group, the alkyl moiety having 1 to 6 carbon atoms, and the aryl moiety optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$, wherein R$^5$ is a hydrogen atom or a $C_1$-$C_4$ alkyl group, and wherein two adjacent substituents of the aryl moiety may be connected to form a methylenedioxy group or an ethylenedioxy group;

(ii) an aralkenyl group, the alkenyl moiety having 2 to 6 carbon atoms, and the aryl moiety optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$, wherein R$^5$ is a hydrogen atom or a $C_1$-$C_4$ alkyl group, and wherein two adjacent substituents of the aryl moiety may be connected to form a methylenedioxy group or an ethylenedioxy group;

(iii) an aryl group, optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$, wherein R$^5$ is a hydrogen atom or a $C_1$-$C_4$ alkyl group, and wherein two adjacent substituents of the aryl group may be connected to form a methylenedioxy group or an ethylenedioxy group;

(iv) a heteroaryl group, optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$, wherein R$^5$ is a hydrogen atom or a $C_1$-$C_4$ alkyl group, and wherein two adjacent substituents of the heteroaryl group may be connected to form a methylenedioxy group or an ethylenedioxy group;

(v) a heteroaralkyl group, the alkyl moiety having 1 to 6 carbon atoms and the heteroaryl moiety optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$ wherein R$^5$ is a hydrogen atom or a $C_1$-$C_4$ alkyl group; and (vi) a heteroaralkenyl group, the alkenyl moiety having 2 to 6 carbon atoms, and the heteroaryl moiety optionally being substituted by one or more substituents selected from the group consisting of a halogen atom, —NH$_2$, —NO$_2$, —CN, —OH, a $C_1$-$C_4$ alkyl group, a $C_1$-$C_4$ alkoxy group and —COOR$^5$ wherein R$^5$ is a hydrogen atom or a $C_1$-$C_4$ alkyl group;

and $R^{13}$ is selected from the group consisting of
- (b) a $C_1$-$C_6$ alkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
  wherein $R^{12}$ is a $C_1$-$C_4$ alkyl group; and
  wherein $R^{11}$ is selected from the group consisting of
    hydrogen,
    a $C_1$-$C_4$ alkyl group,
    an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H, and
    a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H;
- (c) a $C_3$ to $C_7$ cycloalkyl group, optionally substituted by one or more substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
  wherein $R^{12}$ is a $C_1$-$C_4$ alkyl group; and
  wherein $R^{11}$ is selected from the group consisting of
    hydrogen,
    a $C_1$-$C_4$ alkyl group,
    an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H, and
    a heteroaryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H,
- (d) an aryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;
- (e) an aralkyl group, the alkyl moiety having 1 to 6 carbon atoms, and the aryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;
- (f) a heteroaryl group, optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group; and
- (g) a heteroaralkyl group, the alkyl moiety having 1 to 6 carbon atoms, and the heteroaryl moiety optionally being substituted by one or more substituents selected from the group consisting of a $C_1$-$C_4$ alkyl group, a halogen atom, a $C_1$-$C_4$ haloalkyl group, —OH, a $C_1$-$C_4$ alkoxy group, —NH$_2$, —NHR$^{13}$ with R$^{13}$ being a $C_1$-$C_4$ alkyl group, —NR$^{13}$R$^{14}$ with R$^{13}$ and R$^{14}$ each being independently from each other a $C_1$-$C_4$ alkyl group, —NO$_2$, —CN, —COOH, —COOR$^{13}$ with R$^{13}$ being a $C_1$-$C_4$ alkyl group, and —SO$_3$H; and wherein two adjacent substituents of the aryl group may be connected to form a methylenedioxy group or an ethylenedioxy group;
or a salt thereof.

16. The compound according to claim 15, wherein $R^4$ is selected from the group consisting of
- (b) a $C_1$-$C_6$ alkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;
  wherein $R^{12}$ is a $C_1$-$C_4$ alkyl group; and
  wherein $R^{11}$ is selected from the group consisting of
    hydrogen,
    a $C_1$-$C_4$ alkyl group,
    an aryl group that is optionally substituted by one, two or three substituents that are independently from each other selected from the group consisting of a $C_1$-$C_4$ alkyl group, halogen, a $C_1$-$C_4$ haloalkyl group, —OH, a $C_1$-$C_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;

(c) a C$_3$ to C$_7$ cycloalkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, —NO$_2$, -triazole-R$^{11}$, and —CH$_2$—R$^{11}$;

wherein R$^{12}$ is a C$_1$-C$_4$ alkyl group; and
wherein R$^{11}$ is selected from the group consisting of hydrogen,
a C$_1$-C$_4$ alkyl group,
an aryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H, and a heteroaryl group that is optionally substituted by one, two or three substituents that are independently from each other selected from the group consisting of a C$_1$-C$_4$ alkyl group, halogen, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H;

(d) an aryl group, optionally being substituted by one, two or three substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(e) an aralkyl group, the alkyl moiety having 1 to 6 carbon atoms, and the aryl moiety optionally being substituted by one, two or three substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group;

(f) a heteroaryl group, optionally being substituted by one, two or three substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group; and (g) a heteroaralkyl group, the alkyl moiety having 1 to 6 carbon atoms, and the heteroaryl moiety optionally being substituted by one, two or three substituents selected from the group consisting of a C$_1$-C$_4$ alkyl group, a halogen atom, a C$_1$-C$_4$ haloalkyl group, —OH, a C$_1$-C$_4$ alkoxy group, —NH$_2$, —NHR$^{13}$ with R$^{13}$ being a C$_1$-C$_4$ alkyl group, —NR$^{13}$R$^{14}$ with R$^{13}$ and R$^{14}$ each being independently from each other a C$_1$-C$_4$ alkyl group, —NO$_2$, —CN, —COOH, —COOR$^{13}$ with R$^{13}$ being a C$_1$-C$_4$ alkyl group, and —SO$_3$H; and wherein two adjacent substituents of the aryl group may be connected to form a methylenedioxy group or an ethylenedioxy group.

17. The compound according to claim 15,
wherein the aryl moiety or the aryl group of R$^4$ is a phenyl group or a naphthyl group; or
wherein the heteroaryl moiety or the heteroaryl group of R$^4$ is selected from the group consisting of
(i) a five-membered aromatic monocyclic ring, wherein 1, 2, 3, or 4 of the ring atoms are the same or different heteroatoms, said heteroatoms being selected from O, N, or S;
(ii) a six-membered aromatic monocyclic ring, wherein 1, 2, 3, 4, or 5 of the ring atoms are the same or different heteroatoms, said heteroatoms being selected from O, N, or S; and
(iii) an aromatic bicyclic ring system with 8 to 12 members, wherein 1, 2, 3, 4, 5, or 6 of the ring atoms are the same or different heteroatoms, said heteroatoms being selected from O, N, or S.

18. The compound according to claim 15, wherein R$^4$ is selected from the group consisting of methyl, ethyl, propyl, butyl, 2-isopentyl, hexyl, phenyl, benzyl, cyclohexyl, —CH$_2$—CN, —CH$_2$—CH$_2$—NH$_2$, —CH$_2$—CH$_2$—N(CH$_3$)$_2$, —CH$_2$—CH$_2$—NH—CO—CH$_3$, —CH$_2$—CH$_2$—NH—SO$_2$—CH$_3$, and —CH$_2$—CH$_2$—O—CH$_3$.

19. The compound according to claim 15, wherein R$^{13}$ is a C$_1$-C$_6$ alkyl group, optionally substituted by one, two or three substituents selected from the group consisting of halogen, —CN, —NH$_2$, —NR$^{11}$R$^{12}$, —NH—CO—R$^{11}$, —NH—SO$_2$—R$^{11}$, —OR$^{11}$, —SR$^{11}$, —SO$_2$R$^{11}$, —COOR$^{11}$, and —NO$_2$;
wherein R$^{11}$ is selected from the group consisting of hydrogen and a C$_1$-C$_4$ alkyl group, and
wherein R$^{12}$ is a C$_1$-C$_4$ alkyl group.

20. The compound according to claim 15, wherein n is 1 and/or R$^2$ is a hydrogen atom.

21. The compound according to claim 15, wherein the aryl moiety, the heteroaryl moiety, the aryl group or the heteroaryl group of R$^3$ have one or more substituents selected from the group consisting of a halogen atom, —NH$_2$, —NO$_2$ and a methoxy group, or two adjacent substituents of the aryl moiety or the aryl group are connected to form a methylenedioxy group or an ethylenedioxy group.

22. The compound according to claim 15, wherein the aryl moiety or the aryl group of $R^3$ is a phenyl group or a naphthyl group.

23. The compound according to claim 15, wherein X is $SO_2$ and $R^3$ is an aryl or heteroaryl group, optionally being substituted by one or more substituents selected from the group consisting of a halogen atom, $-NH_2$, $-NO_2$, $-CN$, $-OH$, a $C_1$-$C_4$ alkyl group, a $C_1$-$C_4$ alkoxy group and $-COOR^5$, wherein $R^5$ is a hydrogen atom or a $C_1$-$C_4$ alkyl group, and wherein two adjacent substituents of the aryl group or the heteroaryl group may be connected to form a methylenedioxy group or an ethylenedioxy group.

24. The compound according to claim 15, wherein X is C=O and $R^3$ is
   an aralkenyl group, the alkenyl moiety having 2 carbon atoms, the aryl moiety optionally being substituted by one or more substituents selected from the group consisting of a halogen atom, $-NH_2$, $-NO_2$, $-CN$, $-OH$, a $C_1$-$C_4$ alkyl group, a $C_1$-$C_4$ alkoxy group and $-COOR^5$, wherein $R^5$ is a hydrogen atom or a $C_1$-$C_4$ alkyl group, and wherein two adjacent substituents of the aryl moiety may be connected to form a methylenedioxy group or an ethylenedioxy group, or
   a heteroaralkenyl group, the alkenyl moiety having 2 carbon atoms, the heteroaryl moiety optionally being substituted by one or more substituents selected from the group consisting of a halogen atom, $-NH_2$, $-NO_2$, $-CN$, $-OH$, a $C_1$-$C_4$ alkyl group, a $C_1$-$C_4$ alkoxy group and $-COOR^5$, wherein $R^5$ is a hydrogen atom or a $C_1$-$C_4$ alkyl group, and wherein two adjacent substituents of the heteroaryl moiety may be connected to form a methylenedioxy group or an ethylenedioxy group.

25. A pharmaceutical composition comprising the compound according to claim 15, and optionally comprising one or more constituents selected from the group consisting of a pharmaceutically acceptable carrier, a diluent, an excipient and an anti-bacterial therapeutic agent.

26. Method for the prophylaxis or treatment of *Pseudomonas aeruginosa* infections in a patient, comprising the step:
   administering an effective amount of the compound according to claim 15, optionally in combination with one or more anti-bacterial therapeutic agent(s) to a subject in need thereof.

27. Method for the prophylaxis or treatment of *Pseudomonas aeruginosa*-associated respiratory tract infections in a patient suffering from cystic fibrosis, comprising the step:
   administering an effective amount of the compound according to claim 15, optionally in combination with one or more anti-bacterial therapeutic agent(s) to a subject in need thereof.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: PCR primer with NdeI site

<400> SEQUENCE: 1

```
ggaattccat atggcaacaa ggagtg                                              26

<210> SEQ ID NO 2
<211> LENGTH: 25
<212> TYPE: DNA
<213> ORGANISM: Artificial Sequence
<220> FEATURE:
<223> OTHER INFORMATION: PCR primer with HindIII site

<400> SEQUENCE: 2
cccaagcttc tagccgagcg gccag                                               25

<210> SEQ ID NO 3
<211> LENGTH: 21
<212> TYPE: DNA
<213> ORGANISM: Artificial Sequence
<220> FEATURE:
<223> OTHER INFORMATION: Sequencing primer T7 promoter

<400> SEQUENCE: 3
taatacgact cactatatag g                                                   21

<210> SEQ ID NO 4
<211> LENGTH: 19
<212> TYPE: DNA
<213> ORGANISM: Artificial Sequence
<220> FEATURE:
<223> OTHER INFORMATION: Sequencing primer T7 terminator

<400> SEQUENCE: 4
gctagttatt gctcagcgg                                                      19
```